(12) United States Patent
Kawaue et al.

(10) Patent No.: US 9,023,581 B2
(45) Date of Patent: May 5, 2015

(54) RESIST COMPOSITION, METHOD OF FORMING RESIST PATTERN, POLYMERIC COMPOUND, AND COMPOUND

(75) Inventors: Akiya Kawaue, Kawasaki (JP); Kazushige Dohtani, Kawasaki (JP); Yoshiyuki Utsumi, Kawasaki (JP); Jun Iwashita, Kawasaki (JP); Kenri Konno, Kawasaki (JP); Daiju Shiono, Kawasaki (JP); Daichi Takaki, Kawasaki (JP)

(73) Assignee: Tokyo Ohka Kogyo Co., Ltd, Kawasaki-shi (JP)

( * ) Notice: Subject to any disclaimer, the term of this patent is extended or adjusted under 35 U.S.C. 154(b) by 114 days.

(21) Appl. No.: 13/703,865

(22) PCT Filed: Jun. 14, 2011

(86) PCT No.: PCT/JP2011/063560
§ 371 (c)(1),
(2), (4) Date: Dec. 12, 2012

(87) PCT Pub. No.: WO2011/158817
PCT Pub. Date: Dec. 22, 2011

(65) Prior Publication Data
US 2013/0089819 A1 Apr. 11, 2013

(30) Foreign Application Priority Data
Jun. 15, 2010 (JP) ................................. 2010-136313

(51) Int. Cl.
| | | |
|---|---|---|
| *G03F 7/004* | (2006.01) | |
| *G03F 7/30* | (2006.01) | |
| *C07C 69/54* | (2006.01) | |
| *C08F 220/38* | (2006.01) | |
| *G03F 7/027* | (2006.01) | |
| *C07C 309/04* | (2006.01) | |
| *C07C 309/09* | (2006.01) | |
| *C07C 309/10* | (2006.01) | |
| *C07C 309/12* | (2006.01) | |

(Continued)

(52) U.S. Cl.
CPC .............. *G03F 7/027* (2013.01); *C07C 69/54* (2013.01); *C08F 2220/382* (2013.01); *C07C 309/04* (2013.01); *C07C 309/09* (2013.01); *C07C 309/10* (2013.01); *C07C 309/12* (2013.01); *C07C 311/48* (2013.01); *C07C 311/51* (2013.01); *C07C 381/12* (2013.01); *C07C 2101/14* (2013.01); *C07C 2103/74* (2013.01); *C08F 20/38* (2013.01); *G03F 7/0045* (2013.01); *G03F 7/0046* (2013.01); *G03F 7/0397* (2013.01); *G03F 7/2041* (2013.01); *Y10S 430/111* (2013.01); *Y10S 430/121* (2013.01)

(58) Field of Classification Search
CPC ... G03F 7/0045; G03F 7/0397; C07C 303/32; C07C 309/04; C07C 309/06; C07C 309/12; C07C 309/14; C07C 309/19; C07C 69/54; C08F 220/24; C08F 220/38; C08F 2220/382; C08F 2220/387
USPC ............... 430/270.1, 326, 910, 921; 526/243, 526/245, 256, 257, 281, 282, 286, 287, 526/288; 562/109, 113; 560/219, 220, 221, 560/222
See application file for complete search history.

(56) References Cited

U.S. PATENT DOCUMENTS

| | | |
|---|---|---|
| 5,945,517 A | 8/1999 | Nitta et al. |
| 6,153,733 A | 11/2000 | Yukawa et al. |

(Continued)

FOREIGN PATENT DOCUMENTS

| | | |
|---|---|---|
| EP | 1961739 A1 | 8/2008 |
| EP | 2372456 A2 | 10/2011 |

(Continued)

OTHER PUBLICATIONS

International Search Report mailed on Jul. 19, 2011 in corresponding International Application No. PCT/JP2011/063560.

(Continued)

*Primary Examiner* — John Chu
(74) *Attorney, Agent, or Firm* — Knobbe Martens Olsen & Bear LLP

(57) ABSTRACT

A resist composition which can form a very fine resist pattern with excellent lithography properties, a new polymeric compound useful for the resist composition, and a compound useful as a monomer for the polymeric compound. The resist composition contains a polymeric compound containing a structural unit (a0) represented by general formula (a0) shown below. In the formula (a0), A is an anion represented by the general formula (1) or (2).

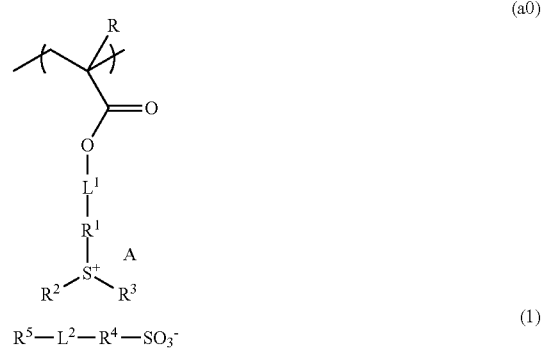

14 Claims, No Drawings

(51) Int. Cl.
*C07C 311/48* (2006.01)
*C07C 311/51* (2006.01)
*C07C 381/12* (2006.01)
*C08F 20/38* (2006.01)
*G03F 7/039* (2006.01)
*G03F 7/20* (2006.01)

(56) References Cited

U.S. PATENT DOCUMENTS

| | | |
|---|---|---|
| 6,949,325 B2 | 9/2005 | Li et al. |
| 7,767,379 B2 * | 8/2010 | Dazai et al. ............ 430/270.1 |
| 8,039,198 B2 * | 10/2011 | Tachibana et al. ...... 430/270.1 |
| 2001/0049073 A1 | 12/2001 | Hada et al. |
| 2004/0110085 A1 | 6/2004 | Iwai et al. |
| 2007/0111140 A1 | 5/2007 | Hatakeyama et al. |
| 2007/0231708 A1 | 10/2007 | Matsumaru et al. |
| 2008/0020290 A1 | 1/2008 | Hatakeyama et al. |
| 2009/0233223 A1 * | 9/2009 | Tachibana et al. ...... 430/270.1 |
| 2010/0136478 A1 | 6/2010 | Kawaue et al. |
| 2010/0143843 A1 | 6/2010 | Oh et al. |
| 2011/0014569 A1 | 1/2011 | Kasahara et al. |
| 2011/0117497 A1 | 5/2011 | Sato et al. |
| 2011/0129777 A1 | 6/2011 | Hatakeyama et al. |
| 2011/0269074 A1 * | 11/2011 | Aqad et al. ................ 430/311 |

FOREIGN PATENT DOCUMENTS

| | | |
|---|---|---|
| JP | A-09-208554 | 8/1997 |
| JP | A-11-035551 | 2/1999 |
| JP | A-11-035552 | 2/1999 |
| JP | A-11-035573 | 2/1999 |
| JP | A-11-322707 | 11/1999 |
| JP | A-2000-206694 | 7/2000 |
| JP | A-2003-241385 | 8/2003 |
| JP | A-2005-336452 | 12/2005 |
| JP | A-2006-045311 | 2/2006 |
| JP | A-2006-259508 | 9/2006 |
| JP | A-2006-259582 | 9/2006 |
| JP | A-2006-317803 | 11/2006 |
| JP | A-2007-316600 | 12/2007 |
| JP | A-2008-052254 | 3/2008 |
| JP | A-2009-080160 | 4/2009 |
| JP | A-2009-080161 | 4/2009 |
| JP | A-2009-242789 | 10/2009 |
| JP | A-2011-022348 | 2/2011 |
| JP | A-2011-037836 | 2/2011 |
| JP | A-2011-038091 | 2/2011 |
| JP | A-2011-138111 | 7/2011 |
| WO | WO 2004/074242 A2 | 9/2004 |
| WO | WO 2005/109102 | 11/2005 |
| WO | WO 2009/150074 | 12/2009 |
| WO | WO 2010/001913 A1 | 1/2010 |

OTHER PUBLICATIONS

European Search Report mailed Feb. 10, 2014 in European Application No. 11795722.5.

Office Action mailed Mar. 25, 2014 in Japanese Application No. 2010-136313.

* cited by examiner

RESIST COMPOSITION, METHOD OF FORMING RESIST PATTERN, POLYMERIC COMPOUND, AND COMPOUND

TECHNICAL FIELD

The present invention relates to a resist composition containing a polymeric compound containing an acid-generating group which generates an acid upon exposure, a method of forming a resist pattern using the resist composition, a new polymeric compound and a compound useful as a monomer for the polymeric compound.

RELATED APPLICATIONS

This application is the U.S. National Phase filing under 35 U.S.C. §371 of PCT/JP2011/063560, filed Jun. 14, 2011, which designated the United States and was published in a language other than English, which claims priority under 35 U.S.C. §119(a)-(d) to Japanese Patent Application No. 2010-136313, filed Jun. 15, 2010, the entire content of which is incorporated herein by reference.

DESCRIPTION OF RELATED ART

In lithography techniques, for example, a resist film composed of a resist material is formed on a substrate, and the resist film is subjected to selective exposure of radial rays such as light or electron beam, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, advances in lithography techniques have lead to rapid progress in the field of pattern miniaturization. Typically, these miniaturization techniques involve increasing the energy (shortening the wavelength) of the exposure light source.

Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source exhibiting energy higher than these excimer lasers, such as electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources. As a resist material that satisfies these conditions, a chemically amplified composition is used which includes an acid generator that generates acid upon exposure.

A chemically amplified composition generally used includes an acid generator and a base component for forming a film. As the base component, a base component which exhibits changed solubility in an alkali developing solution under action of acid generated from the acid generator may be used. For example, as the base component for a chemically amplified positive resist, a composition which exhibits changed solubility in an alkali developing solution under action of acid may be used.

In addition, a resin is typically used as the base component of a chemically amplified resist composition. For example, in the case of a positive resist, a resin containing a structural unit having an acid dissociable, dissolution inhibiting group that is dissociated by the action of acid generated from the acid generator to form an alkali soluble group is typically used. When a resist film formed using the resist composition containing the resin and acid generator is subjected to a selective exposure, acid is generated at exposed portions, the action of generated acid causes the acid-dissociable, dissolution-inhibiting groups to dissociate to form an alkali soluble group, resulting in an increase in the solubility of the entire resin within an alkali developing solution. As a result, the solubility of the exposed portions in an alkali developing solution is changed, whereas the solubility of the unexposed portions in an alkali developing solution remains unchanged. Therefore, the exposed portions are dissolved and removed by alkali developing, and hence, a resist pattern can be formed.

Recently, resins that contain structural units derived from (meth)acrylate esters within the main chain (acrylic resins) are now widely used as base resins for resists that use ArF excimer laser lithography, as they exhibit excellent transparency in the vicinity of 193 nm. (see for example, Patent Document 1)

Here, the term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position. The term "(meth)acrylic acid" is a generic term that includes either or both of acrylic acid having a hydrogen atom bonded to the α-position and methacrylic acid having a methyl group bonded to the α-position.

As acid generators, various types have been proposed including, for example, onium salt acid generators; oxime sulfonate acid generators; diazomethane acid generators; nitrobenzylsulfonate acid generators; iminosulfonate acid generators; and disulfone acid generators. Among these, as the onium salt acid generators, iodonium salts having an iodonium ion as the cation or sulfonium salts having a sulfonium ion as the cation have been conventionally used. In addition, as the anion (acid) which forms a salt with the cation, a perfluoroalkylsulfonate ion can be typically mentioned. A perfluoroalkyl chain having 6 or more carbon atoms is hardly decomposable, and hence, in consideration of improvement in handling in terms of bioaccumulation, currently, a perfluoroalkylsulfonic acid ion having 4 or less carbon atoms such as a nonafluorobutanesulfonate ion or the like is mainly used.

There have been proposed chemically amplified resist compositions containing a resin component which has a structural unit containing in the structure thereof an acid-generator group and a structural unit containing in the structure thereof an acid dissociable, dissolution inhibiting group (for example, Patent Document 2). The resin component having in the structure thereof an acid-generator group has both functions as an acid generator and a base component. For example. the resin having both an acid-generator group and an acid dissociable, dissolution inhibiting group as recited in Patent Document 2, generates acid from the acid-generator group included in the structure thereof upon exposure, and the generated acid dissociates the acid dissociable, dissolution inhibiting group. Therefore, the resin can compose a chemically amplified positive resist alone.

DOCUMENTS OF RELATED ART

Patent Document

[Patent Document 1] Japanese Unexamined Patent Application, First Publication No. 2003-241385

[Patent Document 2] Japanese Unexamined Patent Application, First Publication No. 2006-045311

SUMMARY OF THE INVENTION

As further progress is made in lithography techniques and the application field for lithography techniques expands, improvement is required in the chemically amplified resist composition. For example, improvement will be demanded with respect to various lithography properties such as roughness exposure margin (EL) and the like, as well as resolution. In particular, the roughness becomes the cause of defects in the shape of the resist pattern, and therefore, improvement thereof is important as the pattern size becomes smaller. For example, roughness on the side wall of a pattern (line edge roughness (LER)) can cause various defects such as non-uniformity of the line width of line and space patterns, or distortions around the holes in hole patterns. Such defects of the resist pattern adversely affect the formation of very fine semiconductor elements, and improvement in these characteristics becomes more important as the pattern becomes smaller. For example, in Patent Document 2, in order to improve resolution and LER, a combination of a structural unit having a specific structure and an acid-generator group and a structural unit having an acid dissociable, dissolution inhibiting group, and a structural unit containing a polar group-containing aliphatic polycyclic group, is used, and further improvement has been required.

The present invention takes the above circumstances into consideration, with an object of providing a resist and a method of forming a resist pattern composition which can form a very fine resist pattern with excellent lithography properties, a new polymeric compound useful for the resist composition, and a compound useful as a monomer for the polymeric compound.

A first aspect of the present invention for solving the aforementioned problems is a resist composition which exhibits changed solubility in an alkali developing solution upon exposure, and which contains the polymeric compound (A) having a structural unit (a0) represented by general formula (a0) shown below.

A second aspect of the present invention is a method of forming a resist pattern that includes using the resist composition of the first aspect to form a resist film on a substrate, conducting exposure of the resist film, and alkali-developing the resist film to form a resist pattern.

A third aspect of the present invention is a polymeric compound including a structural unit (a0) represented by general formula (a0) shown below.

A fourth aspect of the present invention is a compound represented by general formula (I) shown below.

[Chemical Formula 1]

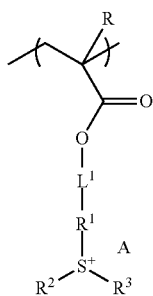

(a0)

In the formula, R represents a hydrogen atom, an alkyl group of 1 to 5 carbon atoms or a halogenated alkyl group of 1 to 5 carbon atoms; $R^1$ represents a divalent aromatic cyclic group; each of $R^2$ and $R^3$ independently represents an aryl group which may have a substituent, an alkyl group which may have a substituent or an alkenyl group which may have a substituent, wherein $R^2$ and $R^3$ may be mutually bonded to form a ring with the sulfur atom; $L^1$ represents a single bond or a divalent linking group; and A represents an anion represented by general formula (1) or (2) shown below.

[Chemical Formula 2]

$$R^5\text{-}L^2\text{-}R^4\text{—}SO_3^-  \quad (1)$$

$$R^7\text{-}L^3\text{-}Y^{10}\text{—}N^-\text{—}SO_2\text{—}R^6 \quad (2)$$

In the formulas, $R^4$ represents an alkylene group of 1 to 4 carbon atom which may have a substituent or a fluorinated alkylene group of 1 to 4 carbon atom which may have a substituent; $L^2$ represents a single bond or a divalent linking group; $R^5$ represents a hydrocarbon group of 3 to 30 carbon atoms which may have a substituent; $R^6$ represents an alkyl group which may have a substituent or a fluorinated alkyl group which may have a substituent; $L^3$ represents a single bond or a divalent linking group; $Y^{10}$ represents a —$SO_2$— or a —CO—; and $R^7$ represents a hydrocarbon group which may have a substituent.

[Chemical Formula 3]

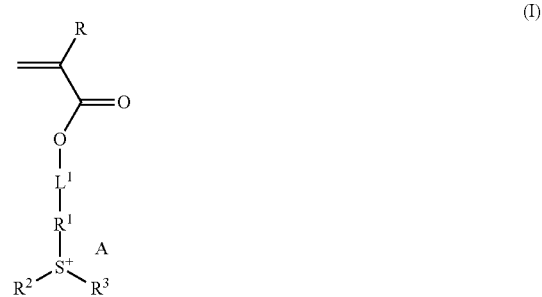

(I)

In the formula, R represents a hydrogen atom, an alkyl group of 1 to 5 carbon atoms or a halogenated alkyl group of 1 to 5 carbon atoms; $R^1$ represents a divalent aromatic cyclic group; each of $R^2$ and $R^3$ independently represents an aryl group which may have a substituent, an alkyl group which may have a substituent or an alkenyl group which may have a substituent, wherein $R^2$ and $R^3$ may be mutually bonded to form a ring with the sulfur atom; $L^1$ represents a single bond or a divalent linking group; and A represents an anion represented by general formula (1) or (2) shown below.

[Chemical Formula 4]

$$R^5\text{-}L^2\text{-}R^4\text{—}SO_3^- \quad (1)$$

$$R^7\text{-}L^3\text{-}Y^{10}\text{—}N^-\text{—}SO_2\text{—}R^6 \quad (2)$$

In the formulas, $R^4$ represents an alkylene group of 1 to 4 carbon atom which may have a substituent or a fluorinated alkylene group of 1 to 4 carbon atom which may have a substituent; $L^2$ represents a single bond or a divalent linking group; $R^5$ represents a hydrocarbon group of 3 to 30 carbon atoms which may have a substituent; $R^6$ represents an alkyl group which may have a substituent or a fluorinated alkyl group which may have a substituent; $L^3$ represents a single bond or a divalent linking group; $Y^{10}$ represents a —$SO_2$— or a —CO—; and $R^7$ represents a hydrocarbon group which may have a substituent.

In the present description and claims, the term "exposure" is used as a general concept that includes irradiation with any form of radiation.

The term "structural unit" refers to a monomer unit that contributes to the formation of a resin component (polymer, copolymer).

The term "alkyl group" includes linear, branched or cyclic, monovalent saturated hydrocarbon, unless otherwise specified.

The term "alkylene group" includes linear, branched or cyclic divalent saturated hydrocarbon, unless otherwise specified.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

The term "aliphatic" is a relative concept used in relation to the term "aromatic", and defines a group or compound that has no aromaticity.

ADVANTAGEOUS EFFECT OF THE INVENTION

According to the present invention, there are provided a resist composition and a method of forming a resist pattern which can form a very fine resist pattern with excellent lithography properties, a new polymeric compound useful for the resist composition, and a compound useful as a monomer for the polymeric compound.

DETAILED DESCRIPTION OF THE INVENTION

<<Resist Composition>>

The resist composition of the present invention is a resist composition which exhibits changed solubility in an alkali developing solution upon exposure, and which includes a polymeric compound (A) which contains a structural unit (a0) represented by general formula (a0) shown below (hereafter, referred to as "component (A)").

[Chemical Formula 5]

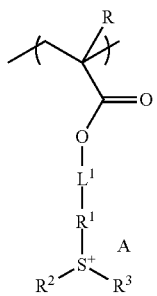

(a0)

In the formula, R represents a hydrogen atom, an alkyl group of 1 to 5 carbon atoms or a halogenated alkyl group of 1 to 5 carbon atoms; R' represents a divalent aromatic cyclic group; each of $R^2$ and $R^3$ independently represents an aryl group which may have a substituent, an alkyl group which may have a substituent or an alkenyl group which may have a substituent, wherein $R^2$ and $R^3$ may be mutually bonded to form a ring with the sulfur atom; $L^1$ represents a single bond or a divalent linking group; and A represents an anion represented by general formula (1) or (2) shown below.

[Chemical Formula 6]

$$R^5\text{-}L^2\text{-}R^4\text{—}SO_3^- \quad (1)$$

$$R^7\text{-}L^3\text{-}Y^{10}\text{—}N^-\text{—}SO_2\text{—}R^6 \quad (2)$$

In the formulas, $R^4$ represents an alkylene group of 1 to 4 carbon atom which may have a substituent or a fluorinated alkylene group of 1 to 4 carbon atom which may have a substituent; $L^2$ represents a single bond or a divalent linking group; $R^5$ represents a hydrocarbon group of 3 to 30 carbon atoms which may have a substituent; $R^6$ represents an alkyl group which may have a substituent or a fluorinated alkyl group which may have a substituent; $L^3$ represents a single bond or a divalent linking group; $Y^{10}$ represents a —$SO_2$— or a —CO—; and $R^7$ represents a hydrocarbon group which may have a substituent.

By including the structural unit (a0), the component (A) has functions as an acid generator and a base component. Therefore, the component (A) can form a film (resist film) alone. In addition, when a resist film formed using the resist composition containing the component (A) is subjected to a selective exposure, acid (represented for A in the formula (1)) is generated from the component (A) at exposed portions and diffused, and hence, the generated acid acts on the component (A) to change the solubility of the component (A) in an alkali developing solution at exposed portions. On the other hand, at unexposed portions, the solubility of the component (A) in a developing solution remains unchanged, so that there is a difference (dissolution contrast) between the exposed portions and the unexposed portions in terms of solubility in a developing solution. Therefore, by alkali developing of the resist film, the exposed portions are dissolved and removed in the case of a positive resist pattern, whereas the unexposed portions are dissolved and removed in the case of a negative resist pattern, thereby forming a resist pattern.

Here, in the present description, the term "base component" refers to an organic compound capable of forming a film. As the base component of a resist composition, an organic compound having a molecular weight of 500 or more is used. When the organic compound has a molecular weight of 500 or more, the organic compound exhibits a satisfactory film-forming ability, and a resist pattern of nano level can be easily formed.

The "organic compound having a molecular weight of 500 or more" is broadly classified into non-polymers and polymers. In general, as a non-polymer, any of those which have a molecular weight in the range of no less than 500 to less than 4,000 is used. Hereafter, a "low molecular weight compound" refers to a non-polymer having a molecular weight in the range of 500 to less than 4,000. As a polymer, any of those which have a molecular weight of 2,000 or more is used. In the present description, the term "polymeric compound" or the term "resin" refers to a polymer having a molecular weight of 2,000 or more. With respect to a polymeric compound, the "molecular weight" is the weight average molecular weight in terms of the polystyrene equivalent value determined by gel permeation chromatography (GPC).

The resist composition of the present invention may be either a positive resist composition that exhibits increased solubility in an alkali developing solution upon exposure or a negative resist composition that exhibits decreased solubility in an alkali developing solution upon exposure.

<Component (A)>

[Structural Unit (a0)]

In formula (a0), R represents a hydrogen atom, an alkyl group of 1 to 5 carbon atoms or a halogenated alkyl group of 1 to 5 carbon atoms.

As the alkyl group for R, a linear or branched alkyl group is preferable, and specific examples include a methyl group, an ethyl group, a propyl group, an isopropyl group, an n-butyl group, an isobutyl group, a tert-butyl group, a pentyl group, an isopentyl group and a neopentyl group.

Examples of the halogenated alkyl group for R include groups in which part or all of the hydrogen atoms within the aforementioned alkyl groups of 1 to 5 carbon atoms has been substituted with a halogen atom. The alkyl group is the same as defined for the alkyl group for the aforementioned R. Examples of the halogen atom which substitutes the hydrogen atom within the alkyl group include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In general formula (a0), $R^1$ represents a divalent aromatic cyclic group.

The divalent aromatic cyclic group is a group in which two hydrogen carbon atoms have been removed from the ring skeleton within an aromatic compound. The ring skeleton within an aromatic compound may be either a hydrocarbon ring constituted of only carbon atoms, or a heterocycle in which the ring skeleton thereof contains a hetero atom, and the hydrocarbon ring is preferable.

As the divalent aromatic cyclic group, an arylene group which may have a substituent is preferable. Here, an arylene group "has a substituent" means that part or all of the hydrogen atoms within the arylene group is substituted with a substituent (a group or an atom other than hydrogen).

The arylene group is not particularly limited, and includes, for example, an arylene group of 6 to 20 carbon atoms. The arylene group is preferably an arylene group of 6 to 10 carbon atoms because it can be synthesized at a low cost. Specific examples thereof include a phenylene group and a naphthylene group.

Examples of substituents which the arylene group may have include an alkyl group, an alkoxy group, a halogen atom, a hydroxyl group, an alkoxyalkyloxy group, $-O-R^{50}-C(=O)-(O)_n-R^{51}-$ [in the formula, $R^{50}$ represents an alkylene group or a single bond; $R^{51}$ represents an acid dissociable group or an acid non-dissociable group; and n represents 0 or 1].

The alkyl group as a substituent is preferably an alkyl group having 1 to 5 carbon atoms, more preferably a methyl group, an ethyl group, a propyl group, an n-butyl group, or a tert-butyl group, and particularly preferably a methyl group and an ethyl group.

The alkoxy group as a substituent is preferably an alkoxy group having 1 to 5 carbon atoms, more preferably a methoxy group, an ethoxy group, an n-propoxy group, an iso-propoxy group, an n-butoxy group or a tert-butoxy group, and particularly preferably a methoxy group or an ethoxy group.

Examples of the halogen atom as a substituent include a fluorine atom, a chlorine atom, a bromine atom and an iodine atom, and a fluorine atom is particularly preferred.

Examples of the alkoxyalkyloxy group as a substituent include $-O-C(R^{47})(R^{48})-O-R^{49}$ [in the formula, each of $R^{47}$ and $R^{48}$ independently represents a hydrogen atom or a linear or branched alkyl group; $R^{49}$ represents an alkyl group, wherein $R^{48}$ and $R^{49}$ may be mutually bonded to form a ring structure, provided that at least one of $R^{47}$ and $R^{48}$ represents a hydrogen atom].

The alkyl group for $R^{47}$ and $R^{48}$ preferably has 1 to 5 carbon atoms. As the alkyl group, an ethyl group or a methyl group is preferable, and a methyl group is most preferable.

It is preferable that at least one of $R^{47}$ and $R^{48}$ represents a hydrogen atom, and the other represents a hydrogen atom or a methyl group. It is particularly preferable that both of $R^{47}$ and $R^{48}$ represent a hydrogen atom.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, an ethyl group, a propyl group, an n-butyl group and a tert-butyl group.

The cyclic alkyl group for $R^{49}$ preferably has 4 to 15 carbon atoms, more preferably 4 to 12, and most preferably 5 to 10. Specific examples thereof include groups in which one or more hydrogen atoms have been removed from a monocycloalkane or a polycycloalkane such as a bicycloalkane, tricycloalkane or tetracycloalkane, and which may or may not be substituted with an alkyl group of 1 to 5 carbon atoms, a fluorine atom or a fluorinated alkyl group. Examples of the monocycloalkane include cyclopentane and cyclohexane. Examples of polycycloalkanes include adamantane, norbornane, isobornane, tricyclodecane and tetracyclododecane. Among these, a group in which one or more hydrogen atoms have been removed from adamantane is preferable.

$R^{48}$ and $R^{49}$ may be mutually bonded to form a ring structure. In such a case, a cyclic group is formed by $R^{48}$, $R^{49}$, the oxygen atom having $R^{49}$ bonded thereto, and the carbon atom having the oxygen atom and $R^{48}$ bonded thereto. Such a cyclic group is preferably a 4 to 7-membered ring, and more preferably a 4 to 6-membered ring.

In the $-O-R^{50}-C(=O)-(O)_n-R^{51}$, the alkylene group for $R^{50}$ is preferably a linear or branched alkylene group of 1 to 5 carbon atoms. Examples of the alkylene group include a methylene group, an ethylene group, a trimethylene group, a tetramethylene group and a 1,1-dimethylethylene group.

The acid dissociable group for $R^{51}$ is not particularly limited as long as it is an organic group that is dissociable by the action of an acid (for example, an anion (1) or (2) generated from the structural unit (a0) upon exposure), and examples thereof include the same acid dissociable, dissolution inhibiting groups as those described above in the explanation of the structural unit (a1) described later. However, unlike the aforementioned acid dissociable, dissolution inhibiting group within the structural unit (a1), the acid dissociable group within the structural unit (a0) is not necessarily required to exhibit the dissolution inhibiting effect in an alkali developing solution.

Specific examples of the acid dissociable group for $R^{51}$ include a tertiary alkyl ester-type acid dissociable group such as a cyclic or chain-like tertiary alkyl group; and an acetal-type acid dissociable group such as an alkoxyalkyl group. Among these, a tertiary alkyl ester-type acid dissociable group is preferable.

Specific examples of the tertiary alkyl ester-type acid dissociable group include a 2-methyl-2-adamantyl group, a 2-ethyl-2-adamantyl group, a 1-methyl-1-cyclopentyl group, a 1-ethyl-1-cyclopentyl group, a 1-methyl-1-cyclohexyl group, a 1-ethyl-1-cyclohexyl group, a 1-(1-adamantyl)-1-methylethyl group, a 1-(1-adamantyl)-1-methylpropyl group, a 1-(1-adamantyl)-1-methylbutyl group, a 1-(1-adamantyl)-1-methylpentyl group, a 1-(1-cyclopentyl)-1-methylethyl group, a 1-(1-cyclopentyl)-1-methylpropyl group, a 1-(1-cyclopentyl)-1-methylbutyl group, a 1-(1-cyclopentyl)-1-methylpentyl group, a 1-(1-cyclohexyl)-1-methylethyl group, a 1-(1-cyclohexyl)-1-methylpropyl group, a 1-(1-cyclohexyl)-1-methylbutyl group, a 1-(1-cyclohexyl)-1-methylpentyl group, a tert-butyl group, a tert-pentyl group and a tert-hexyl group.

The acid non-dissociable group for $R^{51}$ is not particularly limited as long as it is an organic group that is not dissociable by the action of an acid (for example, an anion (1) or (2) generated from the structural unit (a0) upon exposure), and examples thereof include a primary or secondary linear or branched alkyl group and a non-acid-dissociable aliphatic cyclic group described later in the explanation of a structural unit (a4). Examples of preferable acid non-dissociable groups include a decyl group, a tricyclodecyl group, an adamantyl group, a 1-(1-adamantyl)methyl group, a tetracyclododecyl group, an isobornyl group and a norbornyl group.

Among these, as the substituent for the arylene group, an alkyl group and an alkoxy group are preferable, and an alkyl group is more preferable. In particular, a methyl group is particularly preferable.

The number of substituents for arylene group is preferably within the range from 0 to 4, more preferably 0 to 3, and particularly preferably 2. When the number of the hydroxy group is 2, it is preferable that the substituent is bonded to a para-position against the bonding position of adjacent $L^1$ (an oxygen atom (—O—) in the case that $L^1$ represents a single bond).

When the number of substituents is an integer of 2 to 4, the plurality of substituents may be the same or different from each other;

In formula (a0), each of $R^2$ and $R^3$ independently represents an aryl group, alkyl group or alkenyl group which may have a substituent. Here, an aryl group, alkyl group or alkenyl group "has a substituent" means that part or all of the hydrogen atoms within the aryl group, alkyl group or alkenyl group is substituted with a substituent (a group or an atom other than hydrogen).

The aryl group for $R^2$ and $R^3$ is not particularly limited, and includes, for example, an aryl group of 6 to 20 carbon atoms. The aryl group is preferably an aryl group having 6 to 10 carbon atoms because it can be synthesized at a low cost. Specific examples thereof include a phenyl group and a naphthyl group.

Examples of substituents which the aryl group may have include an alkyl group, an alkoxy group, a halogen atom, a hydroxy group, an alkoxyalkyloxy group, —O—$R^{50}$—C(=O)—(O)$_n$—$R^{51}$— [in the formula, $R^{50}$ represents an alkylene group or a single bond; $R^{51}$ represents an acid dissociable group or an acid non-dissociable group; and n represents 0 or 1].

As the alkyl group, alkoxy group, halogen atom, hydroxyl group, alkoxyalkyloxy group and —O—$R^{50}$—C(=O)—(O)$_n$—$R^{51}$— as a substituent, the same alkyl group, alkoxy group, halogen atom, hydroxyl group, alkoxyalkyloxy group and —O—$R^{50}$—C(=O)—(O)$^n$—$R_{51}$— as those described in the explanation for $R^1$, as the substituent which the arylene group may have, can be used.

The alkyl group for $R^2$ and $R^3$ is not particularly limited, and may be linear, branched or cyclic. The alkyl group preferably has 1 to 12 carbon atoms, more preferably 1 to 10, and still more preferably 1 to 5 because it is excellent in resolution and can be synthesized at a low cost.

Specific examples of the alkyl group include a methyl group, an ethyl group, an n-propyl group, an isopropyl group, an n-butyl group, an isobutyl group, an n-pentyl group, a cyclopentyl group, a hexyl group, a cyclohexyl group, a nonyl group and a decyl group.

Examples of substituents which the alkyl group may have include an oxygen atom (=O), an aryl group, an alkyl group, an alkoxy group, a halogen atom, a hydroxy group, an alkoxyalkyloxy group, —O—$R^{50}$—C(=O)—(O)$_n$—$R^{51}$— [in the formula, $R^{50}$ represents an alkylene group or a single bond; $R^{51}$ represents an acid dissociable group or an acid non-dissociable group; and n represents 0 or 1].

Examples of the aryl group as the substituent include the same aryl groups as those described above with respect to the aryl group for $R^2$ and $R^3$.

As the alkyl group, alkoxy group, halogen atom, hydroxyl group, alkoxyalkyloxy group and —O—$R^{50}$—C(=O)—(O)$_n$—$R^{51}$—, the same alkyl group, alkoxy group, halogen atom, hydroxyl group, alkoxyalkyloxy group and —O—$R^{50}$—C(=O)—(O)$^n$—$R_{51}$— as those described in the explanation for $R^1$, as the substituent which the arylene group may have can be used.

Preferable examples of the alkyl group for $R^2$ and $R^3$ include an unsubstituted alkyl group, an oxoalkyl group, an aralkyl group, an aryloxoalkyl group, a carboxyalkyl group and an alkoxycarbonylalkyl group.

The unsubstituted alkyl group is preferably an alkyl group of 1 to 5 carbon atoms, and a methyl group is particularly preferable.

The oxoalkyl group is preferably a 2-oxoalkyl group in which an oxygen atom (=O) is bonded to 2nd position of an alkyl group having 2 or more carbon atoms.

The aryloxoalkyl group refers to a group in which an aryl group is bonded to an oxoalkyl group, and the oxoalkyl group is the same group as those described above. In addition, examples of the aryl group bonded to the oxoalkyl group include the same aryl groups as those described above with respect to the aryl group for $R^2$ and $R^3$.

The alkenyl group for $R^2$ and $R^3$ is not particularly limited, and may be linear or branched. The alkenyl group preferably has 2 to 15 carbon atoms, and more preferably 2 to 10.

Examples of the substituent which the alkenyl group may have include the same groups as those described above as the substituent which the alkenyl group represented by $R^2$ and $R^3$ may have.

In general formula (a0), $R^2$ and $R^3$ may be mutually bonded to form a ring with the sulfur atom. In such a case, the ring including the sulfur atom is preferably a 3- to 10-membered ring, and more preferably a 5- to 7-membered ring.

In general formula (a0), $L^1$ represents a divalent linking group.

As preferable examples of the divalent linking group for a divalent hydrocarbon group which may have a substituent, and a divalent linking group containing a hetero atom can be given.

A hydrocarbon "has a substituent" means that part or all of the hydrogen atoms within the hydrocarbon group is substituted with a substituent (a group or an atom other than hydrogen).

The hydrocarbon group may be either an aliphatic hydrocarbon group or an aromatic hydrocarbon group.

An "aliphatic hydrocarbon group" refers to a hydrocarbon group that has no aromaticity.

The aliphatic hydrocarbon group as the divalent linking group for $L^1$ may be either saturated or unsaturated. In general, the divalent aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 8, still more preferably 1 to 5, and most preferably 1 or 2.

As the linear aliphatic hydrocarbon group, a linear alkylene group is preferable, and specific examples include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, a branched alkylene group is preferable, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$— and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$— and —$C(CH_2CH_3)_2$—$CH_2$—; alkyltrimethylene groups such as —$CH(CH_3)CH_2CH_2$— and —$CH_2CH(CH_3)CH_2$—; and alkyltetramethylene groups such as —$CH(CH_3)CH_2CH_2CH_2$— and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of substituents include a fluorine atom, a fluorinated lower alkyl group of 1 to 5 carbon atoms, and an oxygen atom (=O).

As examples of the hydrocarbon group containing a ring in the structure thereof, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of substituents include lower alkyl groups of 1 to 5 carbon atoms, fluorine atom, fluorinated lower alkyl groups of 1 to 5 carbon atoms, and oxygen atom (=O).

The aromatic hydrocarbon group is a hydrocarbon group having an aromatic ring.

The aromatic hydrocarbon group as a divalent linking group for $L^1$ preferably has 3 to 30 carbon atoms, more preferably 5 to 30, still more preferably 5 to 20, particularly preferably 6 to 15, and most preferably 6 to 10. Here, the number of carbon atoms within a substituent(s) is not included in the number of carbon atoms of the aromatic hydrocarbon group.

Specific examples of the aromatic hydrocarbon group include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and particularly preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

Examples of an aromatic hydrocarbon group in which part of the carbon atoms constituting the aromatic ring within the aromatic hydrocarbon group is substituted with a hetero atom include a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned heteroatom can be used.

As the substituent with which the hydrogen atom bonded to the aromatic ring is substituted, an alkyl group, an alkoxy group, a halogenated alkyl group, a hydroxy group, an oxygen atom (=O) or the like can be mentioned.

The alkyl group as the substituent is preferably an alkyl group of 1 to 5 carbon atoms, and a methyl group, an ethyl group, a propyl group, an n-butyl group or a tert-butyl group is most desirable.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogenated alkyl group for the substituent include groups in which part or all of the hydrogen atoms within the aforementioned alkyl groups has been substituted with the aforementioned halogen atoms. Examples of the aforementioned halogen atom include a fluorine atom, a chlorine atom, a bromine atom and an iodine atom, and a fluorine atom is preferable.

With respect to a "divalent linking group containing a hetero atom", a hetero atom is an atom other than carbon and hydrogen, and examples thereof include an oxygen atom, a nitrogen atom, a sulfur atom and a halogen atom.

Specific examples of the divalent linking group containing a hetero atom include non-hydrocarbon linking groups such as —O—, —C(=O)—, —C(=O)—O—, a carbonate bond (—O—C(=O)—O—), —S—, —S(=O)$_2$—, —S(=O)$_2$—O—, —NH—, —NR$^{04}$— (R$^{04}$ represents a substituent such as an alkyl group or an acyl group), —NH—C(=O)— and =N—. The alkyl group and acyl group as a substituent R$^{04}$ preferably has 1 to 10 carbon atoms, more preferably 1 to 8, and particularly preferably 1 to 5. Further, a combination of at least one of these non-hydrocarbon linking groups with a divalent hydrocarbon group can also be used. As examples of the divalent hydrocarbon group, the same hydrocarbon group which may have a substituent described above for a divalent linking group can be given, and a linear or branched aliphatic hydrocarbon group is preferable.

The divalent linking group for $L^1$ may or may not have an acid dissociable portion in the structure thereof. An "acid dissociable portion" refers to a portion having a bond which is dissociated by the action of acid (for example, an anion (1) or (2)) generated upon exposure. When $L^1$ group has an acid dissociable portion, it preferably has an acid dissociable portion having a tertiary carbon atom bonded to an oxygen atom (—O—) at the terminal of a carbonyloxy group. The action of acid to the acid dissociable portion causes cleavage of the bond between the oxygen atom and the tertiary carbon atom.

As the divalent linking group for a group represented by general formula: —$Y^2$—C(=O)—O— (in the formula, $Y^2$ represents a divalent linking group) is particularly desirable.

As the divalent linking group for $Y^2$, the same divalent linking group as described for $L^1$ can be mentioned, and an alkylene group, a divalent aliphatic cyclic group or a divalent linking group containing a hetero atom is particularly preferable. Among these, an alkylene group is particularly desirable.

When $Y^2$ represents an alkylene group, it preferably has 1 to 10 carbon atoms, more preferably 1 to 6, still more preferably 1 to 4, and most preferably 1 to 3. Specific examples of alkylene groups include the aforementioned linear alkylene groups and branched alkylene groups.

When $Y^2$ represents a divalent aliphatic cyclic group, as the aliphatic cyclic group, the same aliphatic cyclic groups as those described above for the "aliphatic hydrocarbon group containing a ring in the structure thereof" can be used.

As the aliphatic cyclic group, a group in which two or more hydrogen atoms have been removed from cyclopentane, cyclohexane, norbornane, isobornane, adamantane, tricyclodecane or tetracyclododecane is particularly desirable.

When $Y^2$ represents a divalent linking group containing a hetero atom, preferable examples of the divalent linking group containing a hetero atom include —O—, —C(=O)—O—, —C(=O)—, —O—C(=O)—O—, —C(=O)—NH—, —NH— (H may be substituted with a substituent such as an alkyl group or an acyl group), —S—, —S(=O)$_2$—, —S(=O)$_2$—O—, a group represented by the formula: -$A^1$-O—$B^1$—, a group represented by the formula -$A^1$-O—C(=O)—$B^1$— and a group represented by the formula -[$A^1$-C(=O)—O]$_m$—$B^1$—. Herein, each of $A^1$ and $B^1$ independently represents a divalent hydrocarbon group which may have a substituent, and m represents an integer of 0 to 3.

When $Y^2$ represents —NH—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In the group represented by the formula -$A^1$-O—$B^1$—, -$A^1$-O—C(=O)—$B^1$— or -[$A^1$-C(=O)—P]$_m$—$B^1$—, each of $A^1$ and $B^1$ independently represents a divalent hydrocarbon group which may have a substituent.

Examples of divalent hydrocarbon groups for $A^1$ and $B^1$ which may have a substituent include the same groups as those described above for the "divalent hydrocarbon group which may have a substituent" in the explanation for $L^1$.

As $A^1$, a linear aliphatic hydrocarbon group is preferable, more preferably a linear alkylene group, still more preferably a linear alkylene group of 1 to 5 carbon atoms, and a methylene group or an ethylene group is particularly desirable.

As $B^1$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the formula (a0), A is an anion represented by the general formula (1) or (2). Hereafter, an anion represented by the formula (1) refers to as an anion (1), whereas an anion represented by the formula (2) refers to as an anion (2).

{Anion (1)}

In general formula (1), $R^4$ represents an alkylene group of 1 to 4 carbon atoms which may have a substituent or a fluorinated alkylene group of 1 to 4 carbon atoms which may have a substituent.

The alkylene group for $R^4$ is preferably a linear or branched alkylene group. Specific examples of the alkylene group for $R^4$ include a methylene group [—CH$_2$—]; alkylmethylene groups such as —CH(CH$_3$)—, —CH(CH$_2$CH$_3$)—, —C(CH$_3$)$_2$— and —C(CH$_3$)(CH$_2$CH$_3$)—; an ethylene group [—CH$_2$CH$_2$—]; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—, —CH(CH$_2$CH$_3$)CH$_2$—; a trimethylene group (n-propylene group) [—CH$_2$CH$_2$CH$_2$—]; alkyltrimethylene groups such as —CH(CH$_3$)CH$_2$CH$_2$— and —CH$_2$CH(CH$_3$)CH$_2$—; and a tetramethylene group [—CH$_2$CH$_2$CH$_2$CH$_2$—].

As the fluorinated alkylene group for $R^4$, the aforementioned alkylene group in which part or all of the hydrogen atoms has been substituted with fluorine atoms can be used.

In the fluorinated alkyl group, the percentage of the number of fluorine atoms based on the total number of halogen atoms and hydrogen atoms (fluorination ratio (%)) is preferably 10 to 100%, more preferably 50 to 100%, and most preferably 100%. The higher fluorination ratio becomes, the higher acid strength becomes.

Specific examples of $R^4$ include —CF$_2$—, —CF$_2$CF$_2$—, —CF$_2$CF$_2$CF$_2$—, —CF(CF$_3$)CF$_2$—, —CF(CF$_2$CF$_3$)—, —C(CF$_3$)$_2$—, —CF$_2$CF$_2$CF$_2$CF$_2$—, —CF(CF$_3$)CF$_2$CF$_2$—, —CF$_2$CF(CF$_3$)CF$_2$—, —CF(CF$_3$)CF(CF$_3$)—, —C(CF$_3$)$_2$CF$_2$—, —CF(CF$_2$CF$_3$)CF$_2$—, —CF(CF$_2$CF$_2$CF$_3$)—, —C(CF$_3$)(CF$_2$CF$_3$)—, —CHF—, —CH$_2$CF$_2$—, —CH$_2$CH$_2$CF$_2$—, —CH$_2$CF$_2$CF$_2$—, —CH(CF$_3$)CH$_2$—, —CH(CF$_2$CF$_3$)—, —C(CH$_3$)(CF$_3$)—, —CH$_2$CH$_2$CH$_2$CF$_2$—, —CH$_2$CH$_2$CF$_2$CF$_2$—, —CH(CF$_3$)CH$_2$CH$_2$—, —CH$_2$CH(CF$_3$)CH$_2$—, —CH(CF$_3$)CH(CF$_3$)—, —C(CF$_3$)$_2$CH$_2$—, —CH$_2$—, —CH$_2$CH$_2$—, —CH$_2$CH$_2$CH$_2$—, —CH(CH$_3$)CH$_2$—, —CH(CH$_2$CH$_3$)—, —C(CH$_3$)$_2$—, —CH$_2$CH$_2$CH$_2$CH$_2$—, —CH(CH$_3$)CH$_2$CH$_2$—, —CH$_2$CH(CH$_3$)CH$_2$—, —CH(CH$_3$)CH(CH$_3$)—, —C(CH$_3$)$_2$CH$_2$—, —CH(CH$_2$CH$_3$)CH$_2$—, —CH(CH$_2$CH$_2$CH$_3$)— and —C(CH$_3$)(CH$_2$CH$_3$)—.

As $R^4$, a fluorinated alkylene group is preferable, and a fluorinated alkylene group in which the carbon atom bonded to the adjacent sulfur atom is fluorinated is particularly desirable. Examples of such fluorinated alkylene groups include —CF$_2$—, —CF$_2$CF$_2$—, —CF$_2$CF$_2$CF$_2$—, —CF(CF$_3$)CF$_2$—, —CF$_2$CF$_2$CF$_2$CF$_2$—, —CF(CF$_3$)CF$_2$CF$_2$—, —CF$_2$CF(CF$_3$)CF$_2$—, —CF(CF$_3$)CF(CF$_3$)—, —C(CF$_3$)$_2$CF$_2$—, —CF(CF$_2$CF$_3$)CF$_2$—, —CH$_2$CF$_2$—, —CH$_2$CH$_2$CF$_2$—, —CH$_2$CF$_2$CF$_2$—, —CH$_2$CH$_2$CH$_2$CF$_2$—, —CH$_2$CH$_2$CF$_2$CF$_2$— and —CH$_2$CF$_2$CF$_2$CF$_2$—.

Of these, —CF$_2$—, —CF$_2$CF$_2$—, —CF$_2$CF$_2$CF$_2$— or CH$_2$CF$_2$CF$_2$— is preferable, —CF$_2$—, —CF$_2$CF$_2$— or —CF$_2$CF$_2$CF$_2$— is more preferable, and —CF$_2$— is particularly desirable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with groups or atoms other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxy group.

In general formula (1), $L^2$ represents a single bond or a divalent linking group.

The divalent linking group for $L^2$ is not particularly limited, and examples thereof include the same divalent linking groups as those described above for the aforementioned $L^1$.

As the divalent linking group for $L^2$, a divalent linking group containing an oxygen atom (hereafter, referred to as an oxygen atom-containing linkage group) is preferable.

The oxygen atom-containing linkage group may contain an atom other than an oxygen atom. Examples of atoms other than oxygen include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), a carbonyl group (—C(=O)—), a carbonyloxy group (—C(=O)—O—), a carbonate group (—O—C(=O)—O—), sulfuryl group (—S(=O)$_2$—), sulfuryloxy group (—S(=O)$_2$—O—), an amido bond (—C(=O)—NH—); and combinations of at least one of the non-hydrocarbon, oxygen atom-containing linking groups with an alkylene group.

The divalent linking group for $L^2$ is preferably a divalent linking group containing at least any one of an ether bond, a carbonyl group and a sulfuryl group, and more preferably at least one group selected from —R$^{91}$—O—, —R$^{91}$—O—C(=O)—, —R$^{91}$—O—C(=O)—R$^{92}$—β—R$^{93}$—, —R$^{91}$—O—R$^{92}$—O—C(=O)—, —R$^{91}$—C(=O)—O—, —R$^{91}$—C(=O)—O—R$^{92}$—, —R$^{91}$—C(=O)—O—R$^{92}$—O—C(=O)— and —R$^{91}$—S(=O)$_2$—O—R$^{92}$—O—C(=O)—.

In the formulas, $R^{91}$ represents a single bond or an alkylene group. The alkylene group is preferably a linear or branched alkylene group, and preferably has 1 to 12 carbon atoms, more preferably 1 to 5, and most preferably 1 to 3.

Specific examples of the alkylene group include a methylene group [—CH$_2$—], alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—, an ethylene group [—CH$_2$CH$_2$—], alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—, a trimethylene group (n-propylene group) [—CH$_2$CH$_2$CH$_2$—], alkyltrimethylene groups such as —CH(CH$_3$)CH$_2$CH$_2$— and —CH$_2$CH(CH$_3$)CH$_2$—, a tetramethylene group [—CH$_2$CH$_2$CH$_2$CH$_2$—], alkyltetramethylene groups such as —CH(CH$_3$)CH$_2$CH$_2$CH$_2$— and —CH$_2$CH(CH$_3$)CH$_2$CH$_2$—, and a pentamethylene group [—CH$_2$CH$_2$CH$_2$CH$_2$CH$_2$—].

In the formulas, each of $R^{92}$ and $R^{93}$ independently represents an alkylene group. As the alkylene group, the same alkylene groups as those for $R^{91}$ above can be used.

As the divalent linking group for $L^2$, a divalent linking group containing a carbonyl group or a sulfuryl group is preferable.

In formula (1), $R^5$ represents a hydrocarbon group of 3 to 30 carbon atoms which may have a substituent.

The hydrocarbon group for $R^5$ may be either an aromatic hydrocarbon group or an aliphatic hydrocarbon group.

The aromatic hydrocarbon group is a hydrocarbon group having an aromatic ring.

The aromatic hydrocarbon group for $R^5$ preferably has 3 to 30 carbon atoms, more preferably 5 to 30, still more preferably 5 to 20, particularly preferably 6 to 15, and most preferably 6 to 12. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and particularly preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

Example of an aromatic hydrocarbon group in which part of the carbon atoms constituting the aromatic ring within the aromatic hydrocarbon group is substituted with a hetero atom include a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned heteroatom can be used.

When $R^5$ is an aryl group or a heteroaryl group, the atom to which $R^5$ is bonded is preferably a carbon atom. For example, $L^2$ is a divalent linking group, the atom within $L^2$ on the terminal bonded to $R^5$ is preferably a carbon atom.

Examples of the substituent with which the hydrogen atom bonded to the aromatic ring within the aromatic hydrocarbon group may be substituted include an alkyl group, an alkoxy group, a halogen atom, a hydroxy group, an oxygen atom (=O), a halogenated alkyl group, a halogenated alkoxy group, a hydroxyalkyl group, —C(=O)—R$^{80}$ [R$^{80}$ represents an alkyl group], —COOR$^{81}$ [R$^{81}$ represents a hydrogen atom or an alkyl group], —OC(=O)R$^{81}$ [R$^{81}$ represents a hydrogen atom or an alkyl group], a cyano group, an amino group, an amido group, a nitro group, a sulfur atom and a sulfonyl group (SO$_2$).

The alkyl group as a substituent may be linear, branched, cyclic, or a combination thereof. The number of carbon atoms thereof is preferably 1 to 30.

When the alkyl group is linear or branched, the number of carbon atoms thereof is preferably 1 to 20, more preferably 1 to 17, still more preferably 1 to 15, and most preferably 1 to 10. Specific examples include the same alkyl groups as those described later as examples of linear or branched, saturated hydrocarbon group which are exemplified as aliphatic hydrocarbon groups. In particular, an alkyl group of 1 to 6 carbon atoms is preferable, and specific examples thereof include a methyl group, an ethyl group, a propyl group, an isopropyl group, an n-butyl group, an isobutyl group, a tert-butyl group, a pentyl group, an isopentyl group, a neopentyl group and a hexyl group. Among these examples, a methyl group or an ethyl group is preferable, and a methyl group is particularly desirable.

When the alkyl group is cyclic (i.e., a cycloalkyl group), the number of carbon atoms is preferably 3 to 30, more preferably 3 to 20, still more preferably 3 to 15, still more preferably 4 to 12, and most preferably 5 to 10. The alkyl group may be monocyclic or polycyclic. Examples thereof include groups in which one or more of the hydrogen atoms have been removed from a monocycloalkane; and groups in which one or more of the hydrogen atoms have been removed from a polycycloalkane such as a bicycloalkane, a tricycloalkane, or a tetracycloalkane. Specific examples of the monocycloalkane include cyclopentane and cyclohexane. Specific examples of the polycycloalkane include adamantane, norbornane, isobornane, tricyclodecane and tetracyclododecane. These cycloalkyl groups may or may not have part or all of the hydrogen atoms bonded to the ring substituted with a substituent such as a fluorine atom or a fluorinated alkyl group.

As examples of the alkoxy group for the substituent, groups in which the alkyl groups described as alkyl group for the substituent have been bonded to an oxygen atom (—O—) can be given.

Examples of the halogen atom as the substituent include a fluorine atom, a chlorine atom, a bromine atom and an iodine atom, and a fluorine atom is preferable.

As examples of the halogenated alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

As examples of the halogenated alkoxy group as the substituent, groups in which part or all of the hydrogen atoms of the aforementioned alkoxy groups for the substituent have been substituted with the aforementioned halogen atoms can be given. As the halogenated alkoxy group, a fluorinated alkoxy group is preferable.

As examples of the hydroxyalkyl group as the substituent, groups in which at least one hydrogen atom of the aforementioned alkyl groups has been substituted with a hydroxy group can be given. The number of hydroxy groups within the hydroxyalkyl group is preferably 1 to 3, and most preferably 1.

In the —C(=O)—R$^{80}$ group, the —COOR$^{81}$ group and the —OC(=O)R$^{81}$ for the substituent, examples of the alkyl group for R$^{80}$ and R$^{81}$ include the same alkyl groups as those described above for the alkyl group for the substituent.

The aliphatic hydrocarbon group for R$^5$ may be either a saturated aliphatic hydrocarbon group, or an unsaturated aliphatic hydrocarbon group. Further, the aliphatic hydrocarbon group may be linear, branched or cyclic.

In the aliphatic hydrocarbon group, part of the carbon atoms constituting the aliphatic hydrocarbon group may be substituted with a substituent group containing a hetero atom, or part or all of the hydrogen atoms constituting the aliphatic hydrocarbon group may be substituted with a substituent group containing a hetero atom.

As the "hetero atom", there is no particular limitation as long as it is an atom other than carbon atom and hydrogen, and examples thereof include a halogen atom, an oxygen atom, a sulfur atom and a nitrogen atom. Examples of the halogen atom include a fluorine atom, a chlorine atom, an iodine atom and a bromine atom.

The "substituent group containing a hetero atom" (hereafter, referred to as "hetero atom-containing substituent") may consist of a hetero atom, or may be a group containing a group or atom other than a hetero atom.

Specific examples of the hetero atom-containing substituent for substituting part of the carbon atoms constituting the aliphatic hydrocarbon group include —O—, —C(=O)—O—, —C(=O)—, —O—C(=O)—O—, —C(=O)—NH—, —NH— (the H may be replaced with a substituent such as an alkyl group or an acyl group), —S—, —S(=O)$_2$— and —S(=O)$_2$O—. When the hetero atom-containing substituent is —NH—, the substituent for substituting H (an alkyl group, an acyl group or the like) preferably has 1 to 10 carbon atoms, more preferably 1 to 8 carbon atoms, and most preferably 1 to 5 carbon atoms. Among these, as the hetero atom-containing substituent, a group containing an oxygen atom is preferable, and a group containing —C(=O)— or —S(=O)$_2$— is more preferable.

When the aliphatic hydrocarbon group is cyclic, the aliphatic hydrocarbon group may contain any of these substituent groups in the ring structure.

Examples of the substituent with which part or all hydrogen atoms within the aliphatic hydrocarbon group may be substituted include an alkoxy group, a halogen atom, a hydroxy group, an oxygen atom, a halogenated alkyl group, a halogenated alkoxy group, a hydroxyalkyl group, —C(=O)—R$^{80}$ [R$^{80}$ represents an alkyl group], —COOR$^{81}$ [R$^{81}$ represents a hydrogen atom or an alkyl group], —OC(=O)R$^{81}$ [R$^{81}$ represents a hydrogen atom or an alkyl group], a cyano group, an amino group, an amido group, a nitro group, a sulfur atom and a sulfonyl group (SO$_2$).

As the alkoxy group, halogen atom, halogenated alkyl group, halogenated alkoxy group, hydroxyalkyl group, —C(=O)—R$^{80}$, —COOR$^{81}$ and —OC(=O)R$^{81}$ for the hetero atom-containing substituent, the same groups as the aforementioned substituent groups with which part or all of the hydrogen atoms bonded to the aromatic ring within the aromatic hydrocarbon group may be substituted, can be used.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable. Further, a group in which a linear or branched, saturated or unsaturated hydrocarbon group is bonded to an aliphatic cyclic group is also preferable.

The linear saturated hydrocarbon group (alkyl group) preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5, still more preferably 2 to 4, and particularly preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group. As the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, particularly preferably 6 to 15, and most preferably 6 to 12.

As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$ or —S(=O)$_2$—O—.

When the aliphatic cyclic group contains a substituent containing a hetero atom in the ring structure thereof, an aliphatic cyclic group which contains a lactone-containing cyclic group or a —SO$_2$-containing cyclic group is preferable.

The term "lactone-containing cyclic group" refers to a cyclic group including a ring containing a —O—C(=O)— structure (lactone ring). The term "lactone ring" refers to a single ring containing a —O—C(=O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group preferably has 3 to 30 carbon atoms, more preferably 4 to 20, still more preferably 4 to 15, and particularly preferably 4 to 12. Herein, the number of carbon atoms refers to the number of carbon atoms constituting the ring skeleton, excluding the number of carbon atoms within a substituent.

Examples of the lactone-containing cyclic group include groups in which at least one hydrogen atom has been removed from the aliphatic hydrocarbon ring in which part of the carbon atoms constituting the ring skeleton has been substituted with a —O—C(=O)—. More specifically, a group in which at least one hydrogen atom has been removed from the aliphatic hydrocarbon ring in which —CH$_2$— or —CH$_2$—CH$_2$— constituting the ring skeleton has been substituted with —O—C(=O)—.

The alicyclic hydrocarbon group preferably has 3 to 20 carbon atoms, and more preferably 3 to 12 carbon atoms. The alicyclic hydrocarbon group may be either a monocyclic group or a polycyclic group. As the monocyclic group, a group in which one hydrogen atom has been removed from a monocycloalkane of 3 to 6 carbon atoms is preferable. Examples of the monocycloalkane include cyclopentane and cyclohexane. As the polycyclic group, a group in which one hydrogen atom has been removed from a polycycloalkane of 7 to 12 carbon atoms is preferable. Examples of the polycycloalkane include adamantane, norbornane, isobornane, tricyclodecane and tetracyclododecane.

Specific examples of lactone-containing monocyclic groups include a group in which one hydrogen atom has been removed from a 4- to 6-membered lactone ring, such as a group in which one hydrogen atom has been removed from β-propionolatone, a group in which one hydrogen atom has been removed from γ-butyrolactone, and a group in which one hydrogen atom has been removed from δ-valerolactone. Specific examples of lactone-containing polycyclic groups include groups in which one hydrogen atom has been removed from a lactone ring-containing bicycloalkane, tricycloalkane or tetracycloalkane.

An "—SO$_2$— containing cyclic group" refers to a cyclic group having a ring containing —SO$_2$— within the ring structure thereof, i.e., a cyclic group in which the sulfur atom (S) within —SO$_2$— forms part of the ring skeleton of the cyclic group. The ring containing —SO$_2$— within the ring skeleton thereof is counted as the first ring. A cyclic group in which the only ring structure is the ring that contains —SO$_2$— in the ring skeleton thereof is referred to as a monocyclic group, and a group containing other ring structures is described as a polycyclic group regardless of the structure of the other rings. The —SO$_2$-containing cyclic group may be either a monocyclic group or a polycyclic group.

As the —SO$_2$— containing cyclic group, a cyclic group containing —O—SO$_2$— within the ring skeleton thereof, i.e., a cyclic group containing a sultone ring in which —O—S— within the —O—SO$_2$— group forms part of the ring skeleton thereof is particularly desirable.

The —SO$_2$— containing cyclic group preferably has 3 to 30 carbon atoms, more preferably 4 to 20, still more preferably 4 to 15, and most preferably 4 to 12. Herein, the number of carbon atoms refers to the number of carbon atoms constituting the ring skeleton, excluding the number of carbon atoms within a substituent.

Examples of the —SO$_2$— containing aliphatic cyclic group include aliphatic cyclic groups in which part of the carbon atoms constituting the ring skeleton has been substituted with a —SO$_2$— group or a —O—SO$_2$— group and has at least one hydrogen atom removed from the aliphatic hydrocarbon ring. Specific examples include an aliphatic hydrocarbon ring in which a —CH$_2$— group constituting the ring skeleton thereof has been substituted with a —SO$_2$— group and has at least one hydrogen atom removed therefrom; and an aliphatic hydrocarbon ring in which a —CH$_2$— or a —CH$_2$—CH$_2$— group constituting the ring skeleton has been substituted with a —O—SO$_2$— group and has at least one hydrogen atom removed therefrom.

The alicyclic hydrocarbon group preferably has 3 to 20 carbon atoms, and more preferably 3 to 12 carbon atoms. The alicyclic hydrocarbon group may be either a monocyclic group or a polycyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

Specific examples of such lactone-containing cyclic groups include groups represented by formulas (L1) to (L6) shown below.

Specific examples of such —SO$_2$-containing cyclic groups include groups represented by formulas (S1) to (S4) shown below.

[Chemical Formula 7]

(L1)
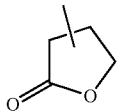

(L2)
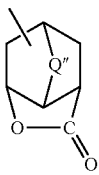

(L3)
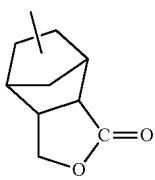

(L4)
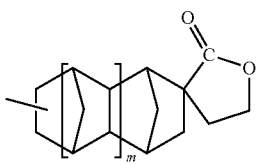

(L5)
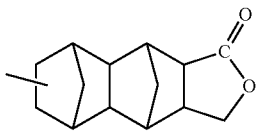

(L6)
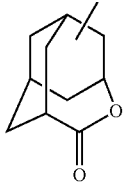

(S1)
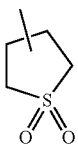

(S2)
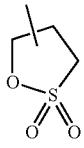

(S3)
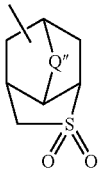

(S4)
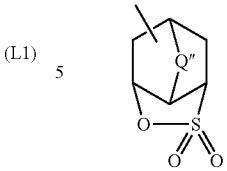

In the formulas, Q" represents an oxygen atom, a sulfur atom or an alkylene group which may contain an oxygen atom or a sulfur atom; and m represents 0 or 1.

In the formulas, the alkylene group for Q" is preferably linear or branched, and preferably has 1 to 5 carbon atoms. Specific examples of the alkylene group include a methylene group [—$CH_2$—], alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—, an ethylene group [—$CH_2CH_2$—], alkylethylene groups such as —CH($CH_3$)$CH_2$—, —CH($CH_3$)CH($CH_3$)—, —C($CH_3$)$_2CH_2$— and —CH($CH_2CH_3$)$CH_2$—, a trimethylene group (n-propylene group) [—$CH_2CH_2CH_2$—], alkyltrimethylene groups such as —CH($CH_3$)$CH_2CH_2$— and —$CH_2$CH($CH_3$)$CH_2$—, a tetramethylene group [—$CH_2CH_2CH_2CH_2$—], alkyltetramethylene groups such as —CH($CH_3$)$CH_2CH_2CH_2$— and —$CH_2$CH($CH_3$)$CH_2CH_2$—, and a pentamethylene group [—$CH_2CH_2CH_2CH_2CH_2$—]. Among these, a methylene group or an alkylmethylene group is preferable, and a methylene group, —CH($CH_3$)— or —C($CH_3$)$_2$ is particularly desirable.

The alkylene group may contain an oxygen atom (—O—) or a sulfur atom (—S—). As an example of such a group, the aforementioned alkylene group having —O— or —S— on the terminal or interposed between the carbon atoms can be mentioned. Specific examples thereof include —O—$R^{94}$—, —S—$R^{95}$—, —$R^{96}$—O—$R^{97}$— and —$R^{98}$—S—$R^{99}$—. Herein, each of $R^{94}$ to $R^{99}$ independently represents an alkylene group. Examples of the alkylene group include the same alkylene groups as those described above for Q". Among these, —O—$CH_2$—, —$CH_2$—O—$CH_2$—, —S—$CH_2$— and —$CH_2$—S—$CH_2$— are preferable.

These aliphatic cyclic groups may have part or all of the hydrogen atoms substituted with a substituent. Examples of the substituents include an alkyl group, an alkoxy group, a halogen atom, a hydroxy group, an oxygen atom (=O), a halogenated alkyl group, a halogenated alkoxy group, a hydroxyalkyl group, —C(=O)—$R^{80}$ [$R^{80}$ represents an alkyl group], —COO$R^{81}$ [$R^{81}$ represents a hydrogen atom or an alkyl group], —OC(=O)$R^{81}$ [$R^{81}$ represents a hydrogen atom or an alkyl group], a cyano group, an amino group, an amido group, a nitro group, a sulfur atom and a sulfonyl group ($SO_2$).

Among these, an alkyl group, alkoxy group, halogen atom, halogenated alkyl group, halogenated alkoxy group, hydroxyalkyl group, —C(=O)—$R^{80}$, —COO$R^{81}$ and —OC(=O)$R^{81}$ for the hetero atom-containing substituent, the same groups as the aforementioned substituent groups with which part or all of the hydrogen atoms bonded to the aromatic ring within the aromatic hydrocarbon group may be substituted, can be used.

Among these examples, as the substituent for substituting the hydrogen atom of the aforementioned aliphatic cyclic group, an alkyl group, an oxygen atom (=O) or a hydroxy group is preferable.

The aliphatic cyclic group may have 1 substituent, or 2 or more substituents. When the aliphatic cyclic group has a plurality of substituents, the substituents may be the same or different from each other.

As a group in which a linear or branched, saturated or unsaturated hydrocarbon group is bonded to an aliphatic cyclic group, for example, a group in which a linear or branched, saturated hydrocarbon group is bonded to a carbon atom constituting the ring structure of an aliphatic cyclic group is preferable, a group in which a linear, saturated hydrocarbon group is bonded to the carbon atom is more preferable, and a group in which a linear alkyl group is bonded to the carbon atom is particularly desirable.

In the present invention, as $R^5$, a cyclic group which may have a substituent is preferable. The cyclic group may be either an aromatic hydrocarbon group which may have a substituent, or an aliphatic cyclic group which may have a substituent.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, a group which may or may not have a hetero atom in the ring structure thereof can be mentioned, and a group having a hetero atom is preferable. When the aliphatic polycyclic group does not contain a hetero atom in the structure thereof, as the aliphatic polycyclic group, a group in which one or more hydrogen atoms have been removed from the aforementioned polycycloalkane is preferable. When the aliphatic polycyclic group contains a hetero atom in the structure thereof, as the aliphatic polycyclic group, a lactone-containing cyclic group or a —$SO_2$-containing cyclic group is preferable, and groups represented by the formulas (L2) to (L6) and (S3) to (S4) are preferable.

In terms of the effects of the present invention, as the anion (I), an anion represented by general formula (11) or (12) shown below is preferable, and an anion represented by general formula (11) is more preferable.

[Chemical Formula 8]

In the formulas, $X^{10}$ represents a hydrocarbon group of 3 to 30 carbon atoms which may have a substituent; $Q^1$ represents a divalent linking group containing a carbonyl group or a divalent linking group containing a sulfonyl group; p represents an integer of 1 to 3; $X^{20}$ represents a hydrocarbon group of 3 to 30 carbon atoms which may have a substituent; $Q^2$ represents a single bond or an alkylene group; and q represents an integer of 1 to 3.

In the formula (11), as examples of $X^{10}$, the same groups as those described above for $R^5$ in the formula (1) can be given.

The divalent linking group containing a carbonyl group or a divalent linking group containing a sulfonyl group for $Q^1$ is the same divalent linking group containing a carbonyl group or sulfonyl group as described in the explanation of $L^2$ in the formula (1). For example, —$R^{91}$—O—C(=O)—, —$R^{91}$—O—C(=O)—$R^{92}$—O—$R^{93}$—, —$R^{91}$—O—$R^{92}$—O—C(=O)—, —$R^{91}$—C(=O)—O—, —$R^{91}$—C(=O)—O—$R^{92}$—, —$R^{91}$—C(=O)—O—$R^{92}$—O—C(=O)— and —$R^{91}$—S(=O)$_2$—O—$R^{92}$—O—C(=O)— can be mentioned. In the formulas, as described above, $R^{91}$ represents a single bond or an alkylene group; and each of $R^{92}$ to $R^{93}$ independently represents an alkylene group.

p represents an integer of 1 to 3, is preferably 1 or 2, and is most preferably 1.

As the anion represented by formula (11), it is preferable that an anion selected from the group consisting of the anions represented by general formulas (11a) to (11f) shown below.

[Chemical Formula 9]

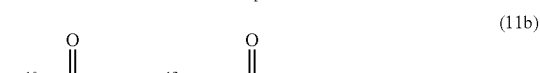

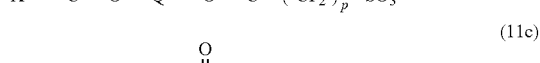

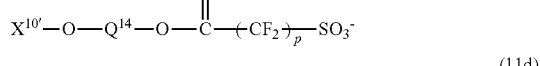

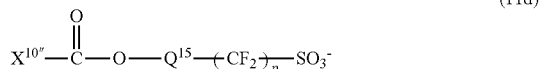

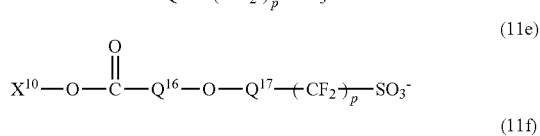

In formula (11a), $X^{10}$ and p are the same as defined above; and $Q^{12}$ represents a single bond or an alkylene group; in formula (11b), $X^{10}$ and p are the same as defined above; $Q^{13}$ represents an alkylene group; in formula (11c), p is the same as defined above; $X^{10'}$ represents a fluorinated aryl group which may have a substituent; $Q^{14}$ represents a single bond or an alkylene group; in formula (II d), p is the same as defined above; $X^{10''}$ represents an aliphatic cyclic group which may have a substituent; $Q^{15}$ represents an alkylene group which may have a substituent; in formula (11e), $X^{10}$ and p are the same as defined above; $Q^{16}$ represents a single bond or an alkylene group; $Q^{17}$ represents a methylene group; in formula (11f), $X^{10}$ and p are the same as defined above; and $Q^{13'}$ represents an alkylene group.

In formula (11a), $X^{10}$ and p are respectfully the same as defined for $X^{10}$ and p in general formula (11).

As $X^{10}$, an aliphatic cyclic group which may have a substituent, a linear aliphatic hydrocarbon group which may have a substituent, or an aromatic hydrocarbon group which may have a substituent is preferable. Of these, an aliphatic cyclic group which contains a hetero atom-containing substituent in the ring structure thereof is more preferable Examples of the alkylene group for $Q^{12}$ include the same alkylene groups as the alkylene group for $R^{91}$ within the —$R^{91}$—O—C(=O)— described as an oxygen atom-containing linkage group in the explanation of the divalent linking group for $L^2$.

As $Q^{12}$, a single bond or a methylene group is particularly desirable. Especially, when $X^{10}$ is an aliphatic cyclic group which may have a substituent, $Q^{12}$ is preferably a single bond. On the other hand, when $X^{10}$ is an aromatic hydrocarbon group, $Q^{12}$ is preferably a methylene group.

Specific examples of preferable anion moieties represented by general formula (11a) are shown below.

[Chemical Formula 10]

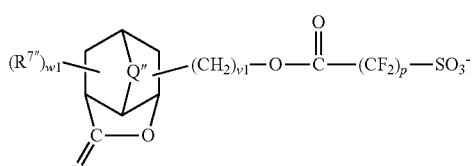
(11a-1)

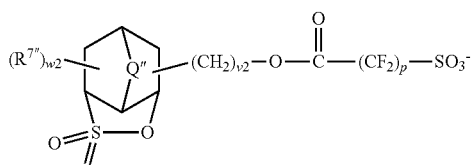
(11a-2)

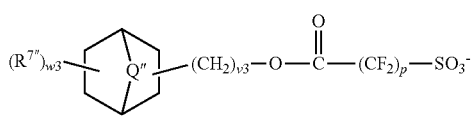
(11a-3)

In the formulas, Q″ and p are the same as defined above; $R^{7″}$ represents a substituent; each of w1 to w3 independently represents an integer of 0 to 9; each of v1 to v3 independently represents an integer of 0 to 5; and p represents an integer of 1 to 3.

In formulas (11a-1) to (11a-3), Q″ is the same as defined for Q″ in the formula (L2), and p is the same as defined for p in the formula (11).

Examples of the substituent for $R^{7″}$ include the same substituents as those described above for substituting part or all of the hydrogen atoms within the aliphatic hydrocarbon group in the explanation for $R^5$.

If there are two or more of the $R^{7″}$ group, as indicated by the values w1 to w3, then the two or more of the $R^{7″}$ groups may be the same or different from each other.

It is preferable that each of v1 to v3 independently represents an integer of 0 to 3, most preferably 0.

It is preferable that each of w1 to w3 independently represents an integer of 0 to 2, and most preferably 0.

In formula (11b), $X^{10}$ and p are respectfully the same as defined for $X^{10}$ and p in general formula (11).

As $X^{10}$, an aliphatic cyclic group which may have a substituent, a linear aliphatic hydrocarbon group which may have a substituent, or an aromatic hydrocarbon group which may have a substituent is preferable.

As the alkylene group for $Q^{13}$, the same alkylene groups as those described above for $Q^{12}$ can be used.

Specific examples of preferable anion moieties represented by general formula (11b) are shown below.

[Chemical Formula 11]

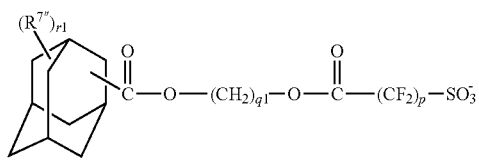
(11b-1)

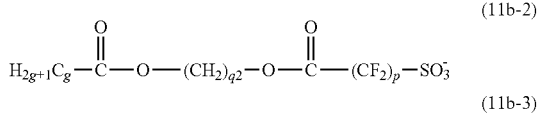
(11b-2)

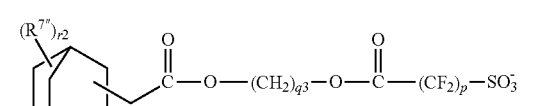
(11b-3)

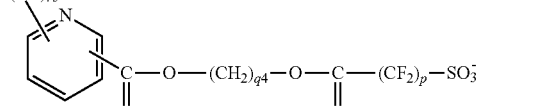
(11b-4)

In the formulas, p is the same as defined above; $R^{7″}$ represents a substituent; each of r1 and r2 independently represents an integer of 0 to 15; r3 represents an integer of 0 to 4; each of q1 to q4 independently represents an integer of 1 to 12; and g represents an integer of 1 to 20.

In the formulas (11b-1) to (11b-4), as the substituent for $R^{7″}$, the same groups as those described above for $R^{7″}$ in the formulas (11a-1) to (11a-3) can be given.

If there are two or more of the $R^{7″}$ group, as indicated by the values r1 to r3, then the two or more of the $R^{7″}$ groups may be the same or different from each other.

It is preferable that each of r1 and r2 independently represent an integer of 0 to 15, more preferably 0 or 1, and still more preferably 0.

r3 is preferably an integer of 0 to 2, more preferably 0 or 1, and still more preferably 0.

It is preferable that each of q1 to q4 independently represent 1 to 8, more preferably 1 to 5, and still more preferably 1 to 3.

g is preferably 1 to 15, and more preferably 1 to 10.

In general formula (11c), p is the same as defined for p in the formula (11), and preferably an integer of 1 or 2, and most preferably 1.

The "fluorinated aryl group" for $X^{10′}$ is an aryl group in which at least one hydrogen atom has been substituted with a fluorine atom. As the aryl group, the same the aryl groups as those described in the explanation of the aromatic hydrocarbon group for $R^5$ can be mentioned, and a phenyl group or a naphthyl group is preferable, and a phenyl group is particularly desirable.

The aryl group may have a substituent other than a fluorine atom. Examples of the substituents include the same groups (provided that, a fluorine atom is excluded) as the substituents for substituting a hydrogen atom within an aromatic hydrocarbon group, which are described in the explanation of the aromatic hydrocarbon group for $X^{10}$.

As the alkylene group for $Q^{14}$, the same alkylene groups as those described above for $Q^{12}$ can be used. As $Q^{14}$, a single bond or a linear alkylene group is particularly desirable. As the alkylene group, an alkylene group of 1 to 5 carbon atoms is particularly desirable.

Specific examples of preferable anion moieties represented by general formula (11c) are shown below.

[Chemical Formula 12]

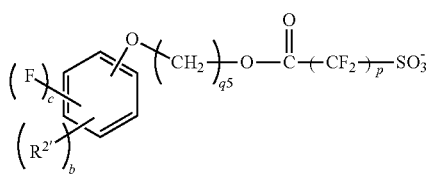

(11c-1)

In the formula, p is the same as defined above; q5 represents an integer of 0 to 5; $R^{2\prime}$ represents a substituent (provided that, a fluorine atom is excluded); b represents an integer of 0 to 4, and c represents an integer of 1 to 5, provided that $1 \leq b+c \leq 5$.

In formula (11c-1), q5 is preferably 1 to 4, more preferably 1 or 2, and most preferably 2.

In the formula (11c), as $R^{2\prime}$, the same groups as those described above for $R^{7\prime\prime}$ in the formulas (11a-1) to (11a-3) can be given. Examples of $R^{2\prime}$ include the same groups (provided that, a fluorine atom is excluded) as the substituents for substituting a hydrogen atom within an aromatic hydrocarbon group, which are described in the explanation of $R^5$. As the substituent, an alkyl group, an alkoxy group, a halogen atom (provided that, a fluorine atom is excluded), a halogenated alkyl group, a hydroxy group, an oxygen atom (=O), —COOR$^{81}$, —OC(=O)R$^{81}$, a hydroxyalkyl group and a cyano group are preferable. As described above, $R^{81}$ represents a hydrogen atom or an alkyl group.

When b is 2, the plurality of $R^{2\prime}$ may be the same or different from each other.

b is most preferably 0.

c is preferably 2 to 5, and most preferably 5.

However, $1 \leq b+c \leq 5$.

In formula (11d), p is the same as defined for p in the formula (11).

In $X^{10\prime\prime}$, as the aliphatic cyclic group, the same aliphatic cyclic group as those described above as the aliphatic hydrocarbon group for $R^5$ can be mentioned, and an adamantly group is particularly preferable.

The aliphatic cyclic group may have a substituent. Examples of the substituent include the same substituents as those described above for substituting part or all of the hydrogen atoms within the aliphatic hydrocarbon group.

As the alkylene group for $Q^{15}$, the same alkylene groups as those described above for $Q^{12}$ can be used. As $Q^{15}$, a linear or branched alkylene group is preferable. As the alkylene group, an alkylene group in which the number of carbon atoms in the main chain is 1 to 12 is preferable. The alkylene group preferably has 1 to 5 of carbon atoms, more preferably 1 to 3, and particularly preferably 1. That is, as $Q^{15}$, a methylene group or an alkylmethylene group is particularly desirable. The alkyl group within the alkylmethylene group is preferably an alkyl group of 1 to 5 carbon atoms.

The alkylene group may have a substituent. Examples of the substituent include the same substituents for substituting part or all of the hydrogen atoms within the aliphatic hydrocarbon group as described in the explanation of $R^5$, preferably a halogen atom, and particularly preferably a fluorine atom.

Specific examples of preferable anion moieties represented by general formula (11d) are shown below.

[Chemical Formula 13]

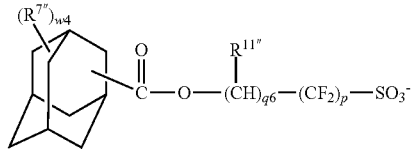

(11d-1)

In the formula, p is the same as defined above; q6 represents an integer of 1 to 12; w4 represents an integer of 0 to 15; $R^{7\prime\prime}$ represents a substituent; and $R^{11\prime\prime}$ represents a hydrogen atom, an alkyl group of 1 to 5 carbon atoms, or a halogenated alkyl group of 1 to 5 carbon atoms.

In the formula, q6 is preferably 1 to 5, more preferably 1 to 3, and most preferably 1.

w4 is preferably an integer of 0 to 2, more preferably 0 or 1, and still more preferably 0.

As the substituent for $R^{7\prime\prime}$, the same groups as those described above for $R^{7\prime\prime}$ in the formulas (11a-1) to (11a-3) can be given. Examples of $R^{7\prime\prime}$ include an alkyl group, an alkoxy group, a halogen atom, a halogenated alkyl group, a hydroxy group, an oxygen atom (=O), —COOR$^{81}$, —OC(=O)R$^{81}$, a hydroxyalkyl group and a cyano group. As described above, $R^{81}$ represents a hydrogen atom or an alkyl group.

If there are two or more of the $R^{7\prime\prime}$ group, as indicated by the value w4, then the two or more of the $R^{7\prime\prime}$ groups may be the same or different from each other.

$R^{11\prime\prime}$ represents a hydrogen atom, an alkyl group of 1 to 5 carbon atoms or a halogenated alkyl group of 1 to 5 carbon atoms. As the halogenated alkyl group, a fluorinated alkyl group is desirable.

[Chemical Formula 14]

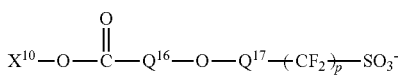

(11e)

In formula (11e), $X^{10}$ and p are the same as defined above; $Q^{16}$ represents a single bond or an alkylene group; and $Q^{17}$ represents a methylene group.

In formula (11e), $X^{10}$ and p are respectfully the same as defined for $X^{10}$ and p in general formula (11).

As $X^{10}$, an aliphatic cyclic group which may have a substituent, a linear or branched aliphatic hydrocarbon group which may have a substituent, or an aromatic hydrocarbon group which may have a substituent is preferable, and an aliphatic cyclic group which may have a substituent, or a linear or branched aliphatic hydrocarbon group which may have a substituent is more preferable.

In particular, $X^{10}$ is preferably a tertiary alkyl ester-type acid-dissociable, dissolution-inhibiting group, because the solubility of the entire component (A) in an alkali developing solution can be increased when the tertiary alkyl ester-type acid-dissociable, dissolution-inhibiting group is dissociated. Examples of tertiary alkyl ester-type acid-dissociable, dissolution-inhibiting groups include the same groups as those exemplified in relation to a structural unit (a1) described later. The tertiary alkyl ester-type acid dissociable, dissolution inhibiting groups may be either aliphatic branched, acid dissociable, dissolution inhibiting groups or aliphatic cyclic group-containing acid dissociable, dissolution inhibiting groups, and are preferably aliphatic cyclic group-containing acid dissociable, dissolution inhibiting groups. In particular, a monovalent aliphatic cyclic group in which an alkyl group is bonded to the carbon atom on the ring skeleton to which an atom adjacent to the acid dissociable, dissolution inhibiting group (e.g., "—O—" within "—C(=O)—O— group") is bonded to form a tertiary carbon atom is preferable. As the alkyl group, a linear or branched alkyl group is preferable. The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable. The branched alkyl group preferably has 3 to 10 carbon atoms, and more preferably 3 to 5. Specific examples of such branched alkyl groups include an isopropyl group, an isobutyl group, a tert-butyl group, an isopentyl group and a neopentyl group, and an isopropyl group is most desirable.

As the alkylene group for $Q^{16}$, the same alkylene groups as those described above for $Q^{12}$ can be used.

Specific examples of preferable anions represented by general formula (11e) are shown below.

[Chemical Formula 15]

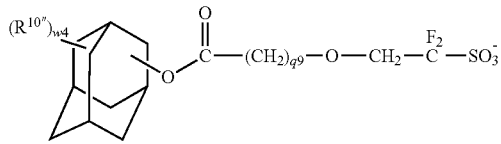

(11e-1)

In the formula, w4 represents an integer of 0 to 15; $R^{10\prime\prime\prime}$ represents a substituent; and q9 represents an integer of 1 to 12.

w4 represents an integer of 0 to 15, and preferably 0 or 1.

As the substituent for $R^{10\prime\prime\prime}$, the same groups as those described above for $R^{7\prime\prime\prime}$ in formulas (11a-1) to (11a-3) can be used, and an alkyl group is particularly preferable.

q9 is preferably 1 to 5, more preferably 1 to 3, and most preferably 1.

In the formula (11e-1), it is preferable that the oxygen atom at the terminal of —C(=O)—O— be bonded to the 2nd position of the adamantane ring. In such a case, $R^{10\prime\prime\prime}$ is preferably a group in which an alkyl group is bonded to the 2nd position of the adamantane ring to form 2-alkyl-2-adamantyl group. The 2-alkyl-2-adamantyl group functions as an acid dissociable, dissolution inhibiting group.

In formula (11f), $X^{10}$ and p are respectfully the same as defined for $X^{10}$ and p in general formula (11).

As $X^{10}$, an aliphatic cyclic group which may have a substituent, a linear aliphatic hydrocarbon group which may have a substituent, or an aromatic hydrocarbon group which may have a substituent is preferable.

As the alkylene group for $Q^{13\prime}$, the same alkylene groups as those described above for $Q^{13}$ can be used.

Specific examples of anion moieties represented by general formula (11f) include an anion in which a carbonyl group not bonded to $(CF_2)_p$ group in the general formula (11b-1) to (11b-4) is substituted with a sulfonyl group. Further, an anion represented by formula (11f-1) shown below is also preferable.

[Chemical Formula 16]

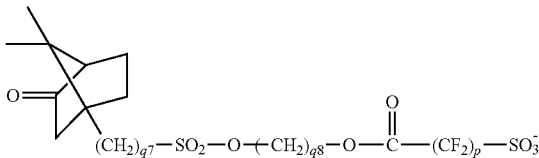

(11f-1)

In the formula, p is the same as defined above; and each of q7 and q8 independently represents an integer of 1 to 12.

In general formula (12), $X^{20}$ represents a hydrocarbon group of 3 to 30 carbon atoms which may have a substituent. As examples of $X^{20}$, the same groups as those described above for $X^{10}$ in the formula (11) can be given.

$Q^2$ represents a single bond or an alkylene group.

Examples of the alkylene group for $Q^2$ include the same alkylene groups as the alkylene group for $R^{91}$ within the —$R^{91}$—O— described as an oxygen atom-containing linkage group in the explanation of the divalent linking group for $L^2$.

q represents an integer of 1 to 3, and preferably an integer of 1 or 2, and is most preferably 2.

Specific examples of preferable anions represented by formula (12) are shown below.

[Chemical Formula 17]

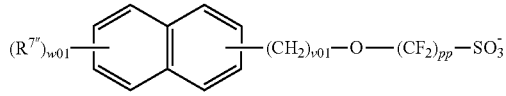

(12a)

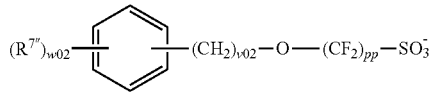

(12b)

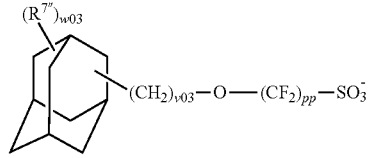

(12c)

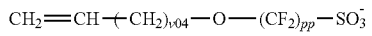

(12d)

In the formulas, $R^{7\prime\prime\prime}$ represents a substituent; w01 represents an integer of 0 to 7; w02 represents an integer of 0 to 5; w03 represents an integer of 0 to 15; each of v01 to v04 independently represents an integer of 0 to 5; and pp represents an integer of 1 to 3.

In the formulas (12a) to (12d), as the substituent for $R^{7\prime\prime\prime}$, the same groups as those described above for $R^{7\prime\prime\prime}$ in the formulas (11a-1) to (11a-3) can be given.

If there are two or more of the $R^{7\prime\prime\prime}$ group, as indicated by the values w01 to w03, then the two or more of the $R^{7\prime\prime\prime}$ groups may be the same or different from each other.

It is preferable that each of v01 to v04 independently represents an integer of 0 to 3, and preferably 0 or 1.

It is preferable that each of w01 to w03 independently represents an integer of 0 to 2, and most preferably 0.

pp is the same as the aforementioned q, preferably 1 or 2, and most preferably 2.

{Anion (2)}

The anion (2) is represented by general formula (2) shown below.

[Chemical Formula 18]

$$R^7\text{-}L^3\text{-}Y^{10}\text{—}N^-\text{—}SO_2\text{—}R^6 \quad (2)$$

In the formula, $R^6$ represents an alkyl group which may have a substituent or a fluorinated alkyl group which may have a substituent; $L^3$ represents a single bond or a divalent linking group; $Y^{10}$ represents a —$SO_2$— or a —CO—; and $R^7$ represents a hydrocarbon group which may have a substituent.

In general formula (2), $R^6$ represents an alkyl group which may have a substituent or a fluorinated alkyl group which may have a substituent.

The alkyl group or fluorinated alkyl group preferably has 1 to 10 carbon atoms, more preferably 1 to 8, and still more preferably 1 to 4.

$R^6$ is preferably a fluorinated alkyl group which may have a substituent because the acid strength of the generated acid is increased. The fluorination ratio (percentage (%) of the number of fluorine atoms, base on the total number of fluorine atoms and hydrogen atoms) is preferably 50 to 100%, more preferably 80 to 100%, and still more preferably 85 to 100%.

The alkyl group or fluorinated alkyl group may have a substituent. The alkyl group or fluorinated alkyl group "has a substituent" means that part or all of the hydrogen atoms or fluorine atoms in the alkyl group or fluorinated alkyl group has been substituted with groups other than hydrogen atoms and fluorine atoms.

Examples of substituents which the alkyl group or fluorinated alkyl group may have include an alkoxy group, a halogen atom other than fluorine atom, a halogenated alkyl group, a hydroxyl group and an oxygen atom (═O).

The alkoxy group as a substituent is preferably an alkoxy group having 1 to 5 carbon atoms, more preferably a methoxy group, an ethoxy group, an n-propoxy group, an isopropoxy group, an n-butoxy group or a tert-butoxy group, and particularly preferably a methoxy group or an ethoxy group.

Examples of the halogen atom as the substituent include a chlorine atom, a bromine atom and an iodine atom.

Examples of the halogenated alkyl group as the substituent include groups in which part or all of the hydrogen atoms within the aforementioned alkyl groups has been substituted with the aforementioned halogen atoms.

In general formula (2), $L^3$ represents a single bond or a divalent linking group.

As the divalent linking group for $L^3$, the same divalent linking group as described for $L^2$ in the general formula (1) can be mentioned, and a divalent hydrocarbon group which may have a substituent or a divalent linking group containing a hetero atom is particularly preferable.

The divalent hydrocarbon group which may have a substituent is preferably an alkylene group or a fluorinated alkylene group. The alkylene group or fluorinated alkylene group is preferably a linear or branched group. Further, the alkylene group or fluorinated alkylene group preferably has 1 to 12 carbon atoms, more preferably 1 to 5 carbon atoms, still more preferably 1 to 4 carbon atoms, and particularly preferably 1 to 3 carbon atoms. As the alkylene group or fluorinated alkylene group, the same alkylene groups and fluorinated alkylene groups as those described above for $R^4$ in the formula (1) can be used.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with groups or atoms other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxy group.

As the divalent linking groups containing a hetero atom, a divalent linking group containing at least one oxygen atom as a hetero atom is preferable. Examples of divalent linking groups containing an oxygen atom include non-hydrocarbon, oxygen atom-containing linkage groups such as an oxygen atom (an ether bond; —O—), an ester bond (—C(═O)—O—), an amido bond (—C(═O)—NH—), a carbonyl group (—C(═O)—) and a carbonate group (—O—C(═O)—O—); and a combination of any of the aforementioned non-hydrocarbon, oxygen atom-containing linkage groups with either an alkylene group or a fluorinated alkylene group.

Examples of combinations of the aforementioned non-hydrocarbon, oxygen-containing linking groups with an alkylene group or a fluorinated alkylene group include $R^{101}$—O—, —O—$R^{102}$—O—C(═O)—, —C(═O)—O—$R^{103}$—, —C(═O)—O—$R^{104}$—O—, —C(═O)—O—$R^{105}$—O—C(═O)—, —$R^{106}$—C(═O)—O—$R^{107}$—O— and —$R^{108}$—C(═O)—O—$R^{109}$—O—C(═O)— [in the formula, each of $R^{101}$ to $R^{109}$ independently represents an alkylene group or a fluoroalkylene group]. In the formula, As the alkylene group or fluorinated alkylene group for $R^{101}$ to $R^{109}$, the same alkylene groups and fluorinated alkylene groups as described in the explanation of the divalent hydrocarbon group for $R^4$ can be used.

As $L^3$, a single bond, an alkylene group, a fluorinated alkylene group or a divalent linking group containing an ether bond is preferable, and a single bond, an alkylene group or —$R^{101}$—O— is more desirable.

In particular, when $Y^{10}$ in the formula (2) is a sulfonyl group, $L^3$ is preferably a fluorinated alkylene group, and a fluorinated alkylene group in which the carbon atom bonded to the adjacent sulfur atom within $Y^{10}$ group is fluorinated is particularly desirable. In such a case, an acid having a strong acid strength is generated from the component (A) upon exposure. As a result, a resist pattern with an excellent shape can be formed, and various lithography properties such as EL margin and the like can be improved.

Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CH_2CF_2$—, —$CH_2CH_2CF_2$—, —$CH_2CF_2CF_2$—, —$CH_2CH_2CH_2CF_2$—, —$CH_2CH_2CF_2CF_2$— and —$CH_2CF_2CF_2CF_2$—. Of these, —$CF_2$—, —$CF_2CF_2$—, —$CF_2CF_2CF_2$— or $CH_2CF_2CF_2$— is preferable, —$CF_2$—, —$CF_2CF_2$— or —$CF_2CF_2CF_2$— is more preferable, and —$CF_2$— is particularly desirable.

When $Y^{10}$ in the formula (2) is a sulfonyl group, the acid strength of the acid generated upon exposure can be controlled by adjusting the number of fluorine atoms within $L^3$. When the carbon atom is not fluorinated, although the acid strength becomes weak, improvement in roughness and the like can be expected.

In the formula (2), $Y^{10}$ may be either —$SO_2$— (i.e., sulfuryl group) or —CO— (i.e., carbonyl group).

$R^7$ represents a hydrocarbon group which may have a substituent. The hydrocarbon group preferably has 1 to 30 carbon atoms, and more preferably 3 to 30. As the hydrocarbon group of 3 to 30 carbon atoms, the same groups as those described above for $R^5$ in the formula (1) can be given.

As $R^7$, a linear or branched saturated hydrocarbon group, a linear or branched monovalent unsaturated hydrocarbon group, or a cyclic group which may have a substituent is preferable. Further, a group in which a linear or branched, saturated or unsaturated hydrocarbon group is bonded to a cyclic group which may have a substituent is also preferable.

Among these, as $R^7$, a cyclic group which may have a substituent is preferable.

The cyclic group may be either an aromatic hydrocarbon group which may have a substituent, or an aliphatic cyclic group which may have a substituent.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group which may have a substituent, the aforementioned group in which one or more hydrogen atoms have been removed from a polycycloalkane, and groups represented by the aforementioned formulas (L2) to (L6), (S3) and (S4) are preferable.

Specific examples of anion moieties preferable as the anion (2) are shown below.

[Chemical Formula 19]

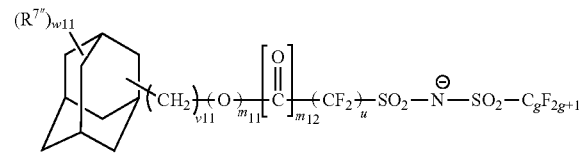
(2a)

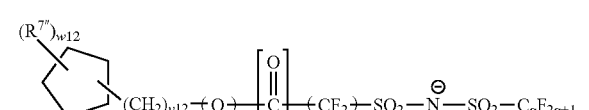
(2b)

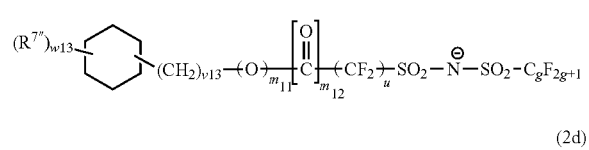
(2c)

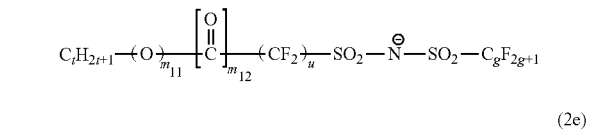
(2d)

(2e)

[Chemical Formula 20]

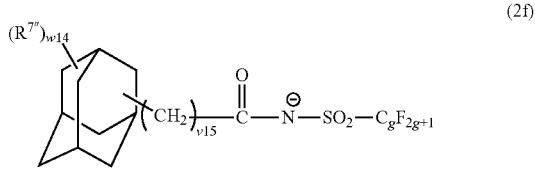
(2f)

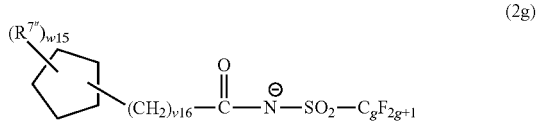
(2g)

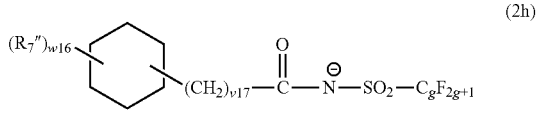
(2h)

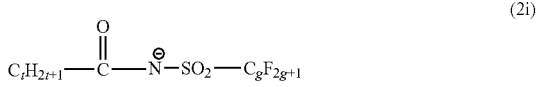
(2i)

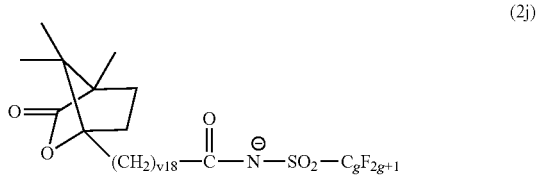
(2j)

In the formulas, $R^{7\prime\prime}$ represents a substituent; w11 represents an integer of 0 to 15; w12 represents an integer of 0 to 9; w13 represents an integer of 0 to 11; w14 represents an integer of 0 to 15; w15 represents an integer of 0 to 9; w16 represents an integer of 0 to 11; each of v11 to v18 independently represents an integer of 0 to 3; u represents an integer of 0 to 4; m11 to m12 represents 0 or 1; g represents an integer of 1 to 3; and t represents an integer of 3 to 20.

In the formulas (2a) to (2j), as the substituent for $R^{7\prime\prime}$, the same groups as those described above for $R^{7\prime\prime}$ in the formulas (11a-1) to (11a-3) can be given.

If there are two or more of the $R^{7\prime\prime}$ group, as indicated by the values w11 to w16, then the two or more of the $R^{7\prime\prime}$ groups may be the same or different from each other.

w11 represents an integer of 0 to 15, w12 represents an integer of 0 to 9, w13 represents an integer of 0 to 11, w14 represents an integer of 0 to 15, w15 represents an integer of 0 to 9, and w16 represents an integer of 0 to 11. It is preferable that each of w11 to w16 independently represents an integer of 0 or 1, and most preferably 0.

Each of v11 to v18 independently represents an integer of 0 to 3, and more preferably 0 or 1.

Each u independently represents an integer of 0 to 4, and preferably 0 to 2.

Each g independently represents an integer of 1 to 3, preferably 1 or 2, and most preferably 1.

t represents an integer of 3 to 20, preferably 3 to 15, and more preferably 3 to 12.

As the structural unit (a0), a structural unit represented by general formula (a0-1) shown below, and a structural unit represented by general formula (a0-11) shown below is more preferable.

[Chemical Formula 21]

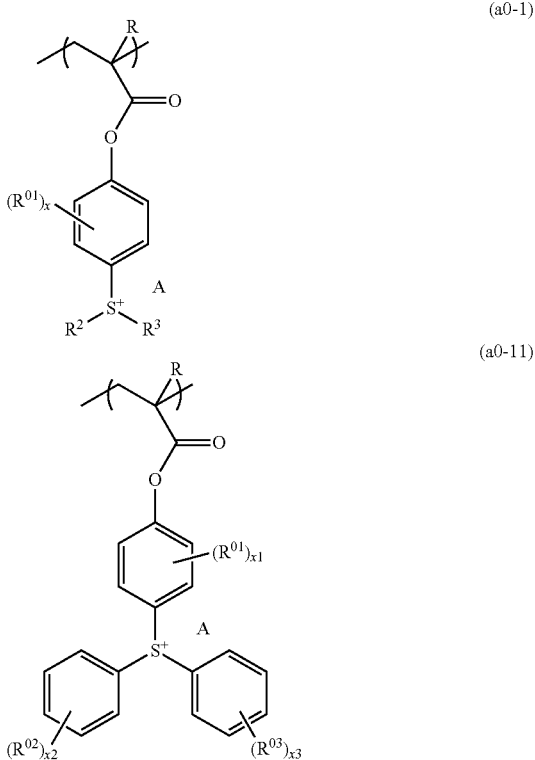

In the formulas, R, $R^2$, $R^3$ and A are the same as defined above; each of $R^{01}$ to $R^{03}$ independently represents an alkyl group or an alkoxy group; x represents an integer of 0 to 4; x1 represents an integer of 0 to 4; and each of x2 and x3 independently represents an integer of 0 to 5.

In general formula (a0-1), R, $R^2$, $R^3$ and A are the same as defined for R, $R^2$, $R^3$ and A in the formula (a0).

Examples of the alkyl group and alkoxy group for $R^{01}$ include the same alkyl groups and alkoxy group as the substituent which the arylene group may have, as described in the explanation of $R^1$ in the formula (a0).

x represents an integer of 0 to 4, preferably an integer of 0 to 2, and particularly preferably an integer of 2.

When x is an integer of 2 or more, the plurality of $R^{01}$ group may be the same or different from each other.

When x is 2, it is preferable that two of $R^{01}$ bond to two of ortho positions against the bonding position of an oxygen atom adjacent to the benzene ring.

In general formula (a0-11), R and A are the same as defined for R and A in the formula (a0), and $R^{01}$ and x1 are the same as defined for $R^{01}$ and x in the formula (a0-1).

As the alkyl group and alkoxy group for $R^{01}$, the same groups as those described above for $R^{01}$ can be used.

x2 represents an integer of 0 to 5, preferably an integer of 0 to 3, and particularly preferably an integer of 0.

When x2 is an integer of 2 or more, the plurality of $R^{02}$ group may be the same or different from each other.

x3 represents an integer of 0 to 5, preferably an integer of 0 to 3, and particularly preferably an integer of 0.

When x3 is an integer of 2 or more, the plurality of $R^{02}$ group may be the same or different from each other.

In the component (A), as the structural unit (a0), one type of structural unit may be used, or two or more structural units may be used.

In the component (A1), the amount of the structural unit (a0) based on the combined total of all structural units constituting the component (A) is preferably 3 mol % or more, more preferably 5 mol % or more, and still more preferably 8 mol % or more. The larger the amount of the component (A), the better the sensitivity. The upper limit of the amount of the component (A) is not particularly limited, and may be 100%. In order to impart predetermined properties (such as a property of exhibiting changed solubility in an alkali developing solution by the action of acid, a compatibility with an alkali developing solution and the like) to the component (A), in the case where structural units other than the structural unit (a0) is arbitrarily used, the amount of the structural unit (a0) may be appropriately adjusted, taking into consideration the valance between the effect of the structural unit (a0) and the properties to be imparted.

For example, when the component (A) contains the structural unit (a1) described later, the amount of the structural unit (a0) based on the combined total of all structural units constituting the component (A) is preferably 50 mol % or less, more preferably 30 mol % or less, and still more preferably 20 mol % or less.

The component (A) may include a structural unit other than the structural unit (a0) as necessary. The other structural unit is not particularly limited, and any of the known structural unit contained in base components in conventional positive-type or negative-type chemically amplified resist compositions can be selected, taking into consideration the component (A) being used for either a positive resist composition or a negative resist composition.

When the resist composition according to the present invention is a positive resist composition, as the component (A), a component which has an acid dissociable, dissolution inhibiting group and exhibits increased solubility in an alkali developing solution by the action of acid (hereafter, referred to as "component (A1)") is preferable. In the case where the component (A1) contains the structural unit (a0) and an acid dissociable, dissolution inhibiting group in the structure thereof, acid (A in the formula (a0)) is generated from the structural unit (a0) upon exposure, and the acid dissociable, dissolution inhibiting group is dissociated by the action of acid. As a result, the solubility of the entire component (A1) in an alkali developing solution is increased. Therefore, the component (A1) can constitute a positive chemically amplified resist composition alone. The acid dissociable, dissolution inhibiting group will be described later in relation to the structural unit (a1).

However, the present invention is not limited thereto, and in the case of positive-type, the component (A1) may not be have an acid dissociable, dissolution inhibiting group. For example, when the resist composition contains a component which exhibits increased solubility in an alkali developing solution by the action of acid (for example, a component (C) described later) as well as the component (A1), the resist composition exhibits increased solubility in an alkali developing solution by the action of acid.

When the resist composition according to the present invention is a negative resist composition, as the component (A), a component which exhibits alkali solubility and has a group which has a cross-linking reactivity to occur a crosslinking reaction by the action of acid (hereafter, referred to as crosslinking reactive group) (hereafter, referred to as "component (A2)") is preferable. Furthermore, the resist composition preferably contains a cross-linking agent as well as the component (A2). When a resist film formed using the resist composition is subjected to a selective exposure, acid is generated from the structural unit (a0) at exposed portions, and a crosslinking reaction between a crosslinking reactive group and a cross-linking agent is proceeded by the action of acid, thereby reducing the solubility of the component (A2) in the alkali developing solution. As a result, a resist pattern can be formed. As an example of such a crosslinking reactive group, a hydroxy group and a carboxy group can be given.

However, the present invention is not limited thereto, and in the case of negative-type, the component (A2) may not be have a crosslinking reactive group. For example, when the resist composition contains a component which exhibits alkali solubility and has a crosslinking reactive group (for example, an alkali soluble resin which has been conventionally used as a base component for a negative resist composition), the resist composition exhibits reduced solubility in an alkali developing solution by the action of acid. In addition, the component (A2) may be a self-crosslinkable component which can form a crosslinkage between molecules of the components (A2). In the case, a crosslinking agent is not necessarily added.

In the present invention, in the case where the component (A) contains an other structural unit as well as the structural unit (a0), the other structural unit is preferably a structural unit derived from an acrylate ester in terms of the adhesiveness to a substrate, the dissolution contrast to a developing solution and the etching resistance.

In the present descriptions and the claims, the expression "structural unit derived from an acrylate ester" refers to a structural unit that is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. Examples of the substituent bonded to the carbon atom on the α-position include an alkyl group of 1 to 5 carbon atoms, a halogenated alkyl group of 1 to 5 carbon atoms and a hydroxyalkyl group of 1 to 5 carbon atoms.

A carbon atom on the α-position of an acrylate ester refers to the carbon atom bonded to the carbonyl group, unless specified otherwise.

As the alkyl group at the α-position in the acrylate ester, a linear or branched alkyl group is preferable, and specific examples include a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group at the α-position include groups in which part or all of the hydrogen atoms of the aforementioned "alkyl group of 1 to 5 carbon atoms for the substituent at the α-position" are substituted with halogen atoms. Examples of the halogen atom include a fluorine atom, a chlorine atom, a bromine atom and an iodine atom, and a fluorine atom is particularly preferred.

Specific examples of the hydroxy alkyl group for the substituent at the α-position include groups in which part or all of the hydrogen atoms of the aforementioned "alkyl group for the substituent at the α-position" are substituted with hydroxy group.

In the present invention, it is preferable that a hydrogen atom, an alkyl group of 1 to 5 carbon atoms or a halogenated alkyl group of 1 to 5 carbon atoms is bonded to the α-position of the acrylate ester, a hydrogen atom, an alkyl group of 1 to 5 carbon atoms or a fluorinated alkyl group of 1 to 5 carbon atoms is more preferable, and in terms of industrial availability, a hydrogen atom or a methyl group is the most desirable.

When the component (A) is a component (A1), It is particularly desirable that the component (A1) have a structural unit (a1) derived from an acrylate ester containing an acid dissociable, dissolution inhibiting group.

In addition, The component (A1) preferably includes at least one structural unit (a2) selected from the group consisting of a structural unit derived from an acrylate ester containing a —$SO_2$— containing cyclic group and a structural unit derived from an acrylate ester containing a lactone-containing cyclic group, as well as the structural unit (a1).

Furthermore, it is preferable that the component (A1) include a structural unit (a3) derived from an acrylate ester containing a polar group-containing aliphatic hydrocarbon group, as well as either the structural unit (a1), or the structural unit (a1) and the structural unit (a2).

[Structural Unit (a1)]

The structural unit (a1)) is a structural unit derived from an acrylate ester containing an acid dissociable, dissolution inhibiting group.

The "acid dissociable, dissolution inhibiting group" has an alkali dissolution inhibiting effect that renders the entire component (A1) insoluble in an alkali developing solution prior to dissociation, and then following dissociation under action of acid generated from the structural unit (a0) or an arbitrary component (B) described later upon exposure, increases the solubility of the entire component (A1) in the alkali developing solution.

As the acid dissociable, dissolution inhibiting group for the structural unit (a1), any of those which have been proposed as acid dissociable, dissolution inhibiting groups for a base resin of a chemically amplified resist may be used. Generally, groups that form either a cyclic or chain-like tertiary alkyl ester with the carboxyl group of the (meth)acrylic acid, and acetal-type acid dissociable, dissolution inhibiting groups such as alkoxyalkyl groups are widely known. Here, the term "(meth)acrylate ester" is a generic term that includes either or both of the acrylate ester having a hydrogen atom bonded to the α-position and the methacrylate ester having a methyl group bonded to the α-position.

A "tertiary alkyl ester" describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" refers to a branched structure having no aromaticity. The "aliphatic branched, acid dissociable, dissolution inhibiting group" is not limited to be constituted of only carbon atoms and hydrogen atoms (not limited to hydrocarbon groups), but is preferably a hydrocarbon group. Further, the "hydrocarbon group" may be either saturated or unsaturated, but is preferably saturated.

As an example of the aliphatic branched, acid dissociable, dissolution inhibiting group, for example, a group represented by the formula —C(R$^{71}$)(R$^{72}$)(R$^{73}$) can be given (in the formula, each of R$^{71}$ to R$^{73}$ independently represents a linear alkyl group of 1 to 5 carbon atoms). The group represented by the formula —C(R$^{71}$)(R$^{72}$)(R$^{73}$) preferably has 4 to 8 carbon atoms, and specific examples include a tert-butyl group, a 2-methyl-2-butyl group, a 2-methyl-2-pentyl group and a 3-methyl-3-pentyl group. Among these, a tert-butyl group is particularly desirable.

The term "aliphatic cyclic group" refers to a monocyclic group or polycyclic group that has no aromaticity. The aliphatic cyclic group preferably has 3 to 30 carbon atoms, more preferably 5 to 30, still more preferably 5 to 20, particularly preferably 6 to 15, and most preferably 6 to 12.

In the "aliphatic cyclic group-containing acid dissociable, dissolution inhibiting group", the "aliphatic cyclic group" may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated.

The aliphatic cyclic group is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated alkyl group, may be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. Further, these groups in which one or more hydrogen atoms have been removed from a monocycloalkane and groups in which one or more hydrogen atoms have been removed from a polycycloalkane may have part of the carbon atoms constituting the ring replaced with an ethereal oxygen atom (—O—).

Examples of aliphatic cyclic group-containing acid dissociable, dissolution inhibiting groups include (i) a monovalent aliphatic cyclic group in which a substituent (a group or an atom other than hydrogen) is bonded to the carbon atom on the ring skeleton to which an atom adjacent to the acid dissociable, dissolution inhibiting group (e.g., "—O—" within "—C(=O)—O— group") is bonded to form a tertiary carbon atom; and (ii) a group which has a branched alkylene group containing a tertiary carbon atom, and a monovalent aliphatic cyclic group to which the tertiary carbon atom is bonded.

In the group (i), as the substituent bonded to the carbon atom to which an atom adjacent to the acid dissociable, dissolution inhibiting group on the ring skeleton of the aliphatic cyclic group, an alkyl group can be mentioned. Examples of the alkyl group include the same groups as those represented by R$^{14}$ in formulas (1-1) to (1-9) described later.

Specific examples of the group (i) include groups represented by general formulas (1-1) to (1-9) shown below.

Specific examples of the group (ii) include groups represented by general formulas (2-1) to (2-6) shown below.

[Chemical Formula 22]

(1-1)

(1-2)

(1-3)

(1-4)

(1-5)

(1-6)

(1-7)

(1-8)

(1-9)

In the formulas above, R$^{14}$ represents an alkyl group; and g represents an integer of 0 to 8.

[Chemical Formula 23]

(2-1)
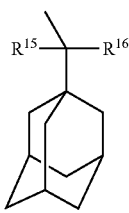

(2-2)
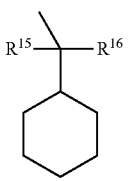

(2-3)
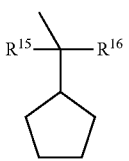

(2-4)
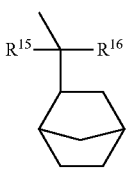

(2-5)
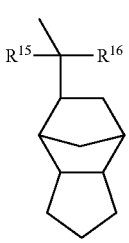

(2-6)
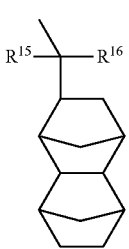

In the formulas above, each of $R^{15}$ and $R^{16}$ independently represents an alkyl group.

As the alkyl group for $R^{14}$, a linear or branched alkyl group is preferable.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples of such branched alkyl groups include an isopropyl group, an isobutyl group, a tert-butyl group, an isopentyl group and a neopentyl group, and an isopropyl group is most desirable.

g is preferably an integer of 0 to 3, more preferably 1 to 3, and still more preferably 1 or 2.

As the alkyl group for $R^{15}$ and $R^{16}$, the same alkyl groups as those for $R^{14}$ can be used.

In formulas (1-1) to (1-9) and (2-1) to (2-6), part of the carbon atoms constituting the ring may be replaced with an ethereal oxygen atom (—O—).

Further, in formulas (1-1) to (1-9) and (2-1) to (2-6), one or more of the hydrogen atoms bonded to the carbon atoms constituting the ring may be substituted with a substituent. Examples of the substituent include an alkyl group of 1 to 5 carbon atoms, a fluorine atom and a fluorinated alkyl group.

An "acetal-type acid dissociable, dissolution inhibiting group" generally substitutes a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 24]

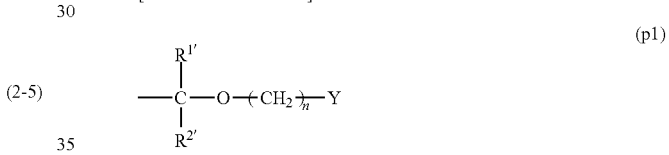
(p1)

In the formula, $R^{1'}$ and $R^{2'}$ each independently represent a hydrogen atom or an alkyl group of 1 to 5 carbon atoms; n represents an integer of 0 to 3; and Y represents an alkyl group of 1 to 5 carbon atoms or an aliphatic cyclic group.

In general formula (p1) above, n is preferably an integer of 0 to 2, more preferably 0 or 1, and most preferably 0.

As the alkyl group for $R^{1'}$ and $R^{2'}$, the same alkyl groups as those described above the alkyl groups as the substituent on the α-position of the aforementioned alkylester can be used, although a methyl group or ethyl group is preferable, and a methyl group is particularly desirable.

In the present invention, it is preferable that at least one of $R^{1'}$ and $R^{2'}$ be a hydrogen atom. That is, it is preferable that the acid dissociable, dissolution inhibiting group (p1) is a group represented by general formula (p1-1) shown below.

[Chemical Formula 25]

(p1-1)

In the formula, $R^{1'}$, n and Y are the same as defined above.

As the alkyl group for Y, the same alkyl groups as those described above the for the substituent on the α-position of the aforementioned alkylester can be mentioned.

As the aliphatic cyclic group for Y, any of the aliphatic monocyclic or polycyclic groups which have been proposed for conventional ArF resists and the like can be appropriately selected for use. For example, the same aliphatic cyclic groups described above in connection with the "acid dissociable, dissolution inhibiting group containing an aliphatic cyclic group" can be used.

Further, as the acetal-type, acid dissociable, dissolution inhibiting group, groups represented by general formula (p2) shown below can also be used.

[Chemical Formula 26]

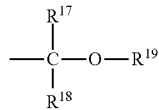

(p2)

In the formula, $R^{17}$ and $R^{18}$ each independently represent a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the $R^{19}$ group may be bonded to the $R^{17}$ group.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

Specific examples of the structural unit (a1) include a structural unit represented by general formula (a1-0-1) shown below and a structural unit represented by general formula (a1-0-2) shown below.

[Chemical Formula 27]

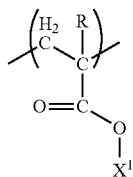

(a1-0-1)

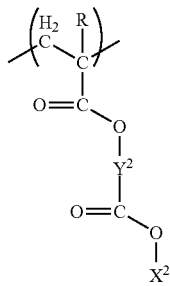

(a1-0-2)

In the formulas, R represents a hydrogen atom, an alkyl group of 1 to 5 carbon atoms or a halogenated alkyl group of 1 to 5 carbon atoms; $X^1$ represents an acid dissociable, dissolution inhibiting group; $Y^2$ represents a divalent linking group; and $X^2$ represents an acid dissociable, dissolution inhibiting group.

In general formula (a1-0-1), the alkyl group and the halogenated alkyl group for R are respectively the same as defined for the alkyl group and the halogenated alkyl group for the substituent on the α-position of the aforementioned alkylester. R is preferably a hydrogen atom, an alkyl group of 1 to 5 carbon atoms or a fluorinated alkyl group of 1 to 5 carbon atoms, and most preferably a hydrogen atom or a methyl group.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is the same as defined above.

$X^2$ is the same as defined for $X^1$ in general formula (a1-0-1).

The divalent linking group for $Y^2$ is not particularly limited, and examples thereof include the same divalent linking groups as those described above for the aforementioned $L^1$ in the formula (a0).

As the divalent linking group for $Y^2$, an alkylene group, a divalent aliphatic cyclic group, a divalent aromatic cyclic group or a divalent linking group containing a hetero atom is particularly preferable.

When $Y^2$ represents an alkylene group, it preferably has 1 to 10 carbon atoms, more preferably 1 to 6, still more preferably 1 to 4, and most preferably 1 to 3.

When $Y^2$ represents a divalent aliphatic cyclic group, as the aliphatic cyclic group, the same aliphatic cyclic groups as those described above for the "acid dissociable, dissolution inhibiting group containing an aliphatic cyclic group" except that two or more hydrogen atoms have been removed therefrom can be used. As the aliphatic cyclic group for $Y^2$, a group in which two or more hydrogen atoms have been removed from cyclopentane, cyclohexane, norbornane, isobornane, adamantane, tricyclodecane or tetracyclododecane is particularly desirable.

When $Y^2$ is a divalent aromatic cyclic group, specific examples of the aromatic cyclic groups include an aromatic hydrocarbon ring (which may have a substituent) having 2 hydrogen atoms removed therefrom. The aromatic hydrocarbon ring preferably has 6 to 15 carbon atoms. Examples of the ring skeleton include a benzene ring, a naphthalene ring, a phenanthrene ring and an anthracene ring. Among these, a benzene ring or a naphthalene ring is particularly desirable.

Examples of the substituent which the aromatic cyclic group may have include a halogen atom, an alkyl group, an alkoxy group, a halogenated lower alkyl group and an oxygen atom (=O). Examples of the halogen atom include a fluorine atom, a chlorine atom, an iodine atom and a bromine atom.

When $Y^2$ represents a divalent linking group containing a hetero atom, examples of the divalent linking group containing a hetero atom include —O—, —C(=O)—O—, —C(=O)—, —O—C(=O)—O—, —C(=O)—NH—, —NH— (H may be substituted with a substituent such as an alkyl group or an acyl group), —S—, —S(=O)$_2$—, —S(=O)$_2$—O—, a group represented by the formula: -$A^1$-O—$B^1$—, a group represented by the formula -$A^1$-O—C(=O)—$B^1$— and a group represented by the formula -[$A^1$-C(=O)—O]$_m$—$B^1$—. Here, in the formula -$A^1$-O—$B^1$—, -$A^1$-O—C(=O)—$B^1$— or -[$A^1$-C(=O)—O]$_m$—$B^1$—, each of $A^1$ and $B^1$ independently represents a divalent hydrocarbon group which may have a substituent, —O— represents an oxygen atom, and m represents an integer of 0 to 3.

When $Y^2$ represents —NH—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In the case where $Y^2$ represents -$A^1$-O—$B^1$—, -$A^1$-O—C(=O)—$B^1$— or -[$A^1$-C(=O)—O]$_m$—$B^1$—, each of $A^1$ and $B^1$ independently represents a divalent hydrocarbon group which may have a substituent. A hydrocarbon "has a substituent" means that part or all of the hydrogen atoms within the hydrocarbon group is substituted with groups or atoms other than hydrogen atom.

The hydrocarbon group for $A^1$ may be either an aliphatic hydrocarbon group, or an aromatic hydrocarbon group. An "aliphatic hydrocarbon group" refers to a hydrocarbon group that has no aromaticity. The aliphatic hydrocarbon group for $A^1$ may be either saturated or unsaturated. In general, the aliphatic hydrocarbon group is preferably saturated.

As specific examples of the aliphatic hydrocarbon group for $A^1$, a linear or branched aliphatic hydrocarbon group, and an aliphatic hydrocarbon group having a ring in the structure thereof can be given.

The linear or branched aliphatic hydrocarbon group preferably has 1 to 10 carbon atoms, more preferably 1 to 8, still more preferably 2 to 5, and most preferably 2.

As the linear aliphatic hydrocarbon group, a linear alkylene group is preferable, and specific examples include a methylene group, an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As the branched aliphatic hydrocarbon group, a branched alkylene group is preferable, and specific examples include various alkylalkylene groups, including alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—; alkyltrimethylene groups such as —CH(CH$_3$)CH$_2$CH$_2$— and —CH$_2$CH(CH$_3$)CH$_2$—; and alkyltetramethylene groups such as —CH(CH$_3$)CH$_2$CH$_2$CH$_2$— and —CH$_2$CH(CH$_3$)CH$_2$CH$_2$—. As the alkyl group within the alkylalkylene group, a linear alkyl group of 1 to 5 carbon atoms is preferable.

The linear or branched aliphatic hydrocarbon group may or may not have a substituent. Examples of the substituent include a fluorine atom, a fluorinated alkyl group of 1 to 5 carbon atoms, and an oxygen atom (=O).

As examples of the hydrocarbon group containing a ring in the structure thereof, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of substituents include lower alkyl groups of 1 to 5 carbon atoms, fluorine atom, fluorinated lower alkyl groups of 1 to 5 carbon atoms, and oxygen atom (=O).

As A in -$A^1$-O—$B^1$—, -$A^1$-O—C(=O)—$B^1$— or -[$A^1$-C(=O)—O]$_m$—$B^1$—, a linear aliphatic hydrocarbon group is preferable, more preferably a linear alkylene group, still more preferably a linear alkylene group of 1 to 5 carbon atoms, and a methylene group or an ethylene group is particularly desirable.

As $B^1$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula -[$A^1$-C(=O)—O]$_m$—$B^1$—, m represents an integer of 0 to 3, preferably an integer of 0 to 2, more preferably 0 or 1, and most preferably 1.

Specific examples of the structural unit (a1) include structural units represented by general formulas (a1-1) to (a1-4) shown below.

[Chemical Formula 28]

(a1-1)

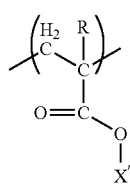

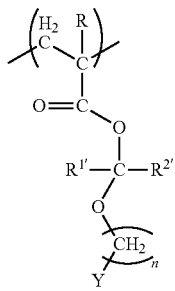

(a1-2)

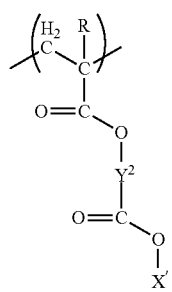

(a1-3)

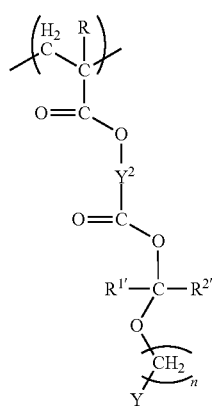

(a1-4)

In the formulas, R, $R^{1\prime}$, $R^{2\prime}$, n, Y and $Y^2$ are the same as defined above; and X' represents a tertiary alkyl ester-type acid dissociable, dissolution inhibiting group.

In the formulas, the tertiary alkyl ester-type acid dissociable, dissolution inhibiting group for X' include the same tertiary alkyl ester-type acid dissociable, dissolution inhibiting groups as those described above.

As $R^{1\prime}$, $R^{2\prime}$, n and Y are respectively the same as defined for $R^{1\prime}$, $R^{2\prime}$, n and Y in general formula (p1) described above in connection with the "acetal-type acid dissociable, dissolution inhibiting group".

$Y^2$ is the same as defined for $Y^2$ in general formula (a1-0-2). Specific examples of structural units represented by general formulas (a1-1) to (a1-4) are shown below.

In the formulas shown below, $R^\alpha$ represents a hydrogen atom, a methyl group or a trifluoromethyl group.

[Chemical Formula 29]

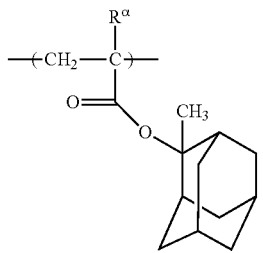

(a1-1-1)

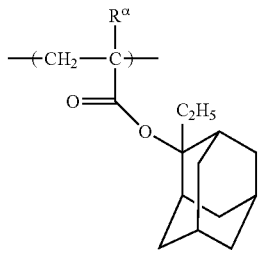

(a1-1-2)

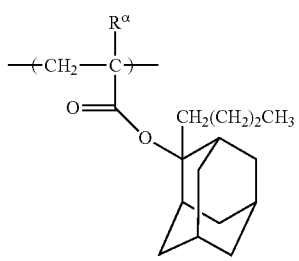

(a1-1-3)

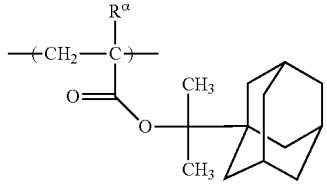

(a1-1-4)

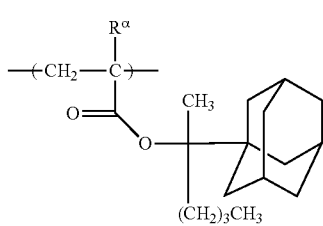

(a1-1-5)

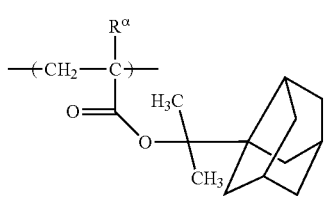

(a1-1-6)

(a1-1-7) 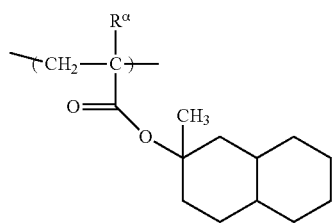
(a1-1-8) 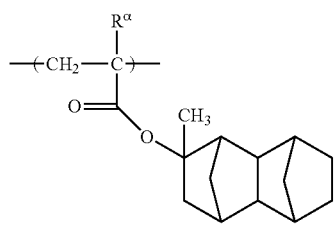
(a1-1-9) 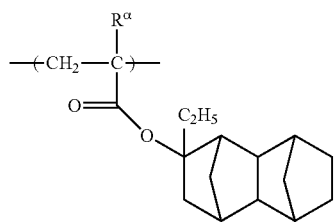
(a1-1-10) 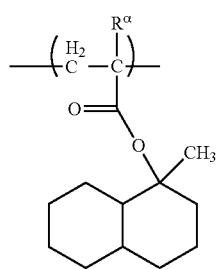
(a1-1-11) 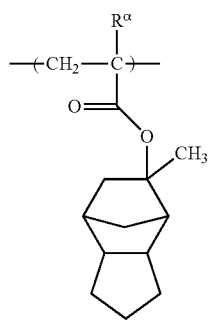
(a1-1-12) 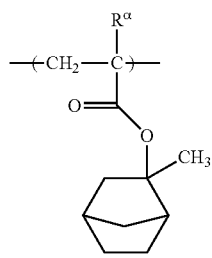
(a1-1-13) 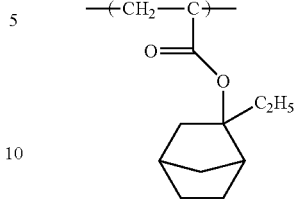
(a1-1-14) 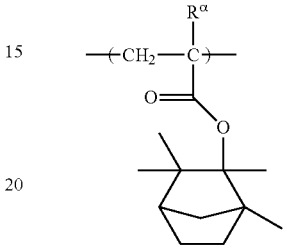
(a1-1-15) 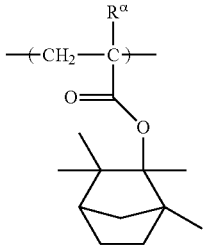
(a1-1-16) 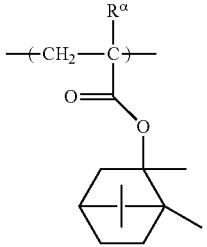
(a1-1-17) 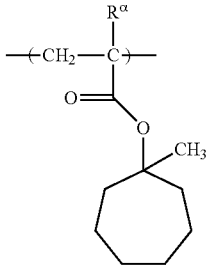
(a1-1-18) 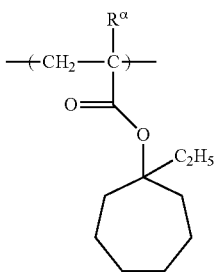

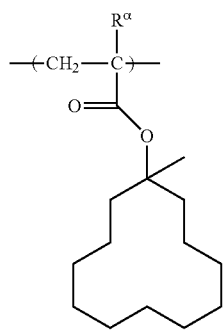 (a1-1-19)
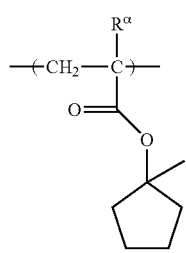 (a1-1-20)
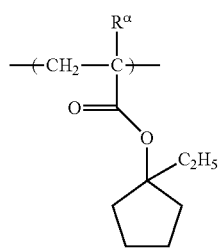 (a1-1-21)
[Chemical Formula 30]
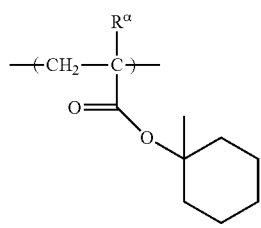 (a1-1-22)
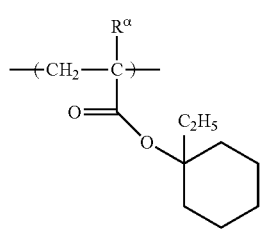 (a1-1-23)
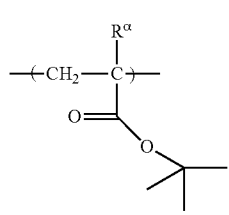 (a1-1-24)
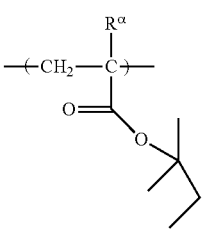 (a1-1-25)
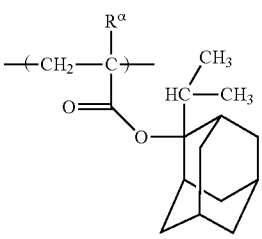 (a1-1-26)
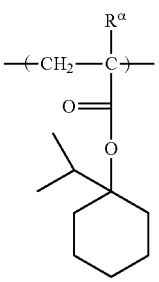 (a1-1-27)
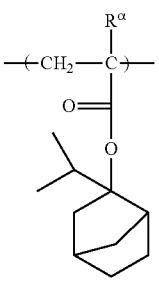 (a1-1-28)
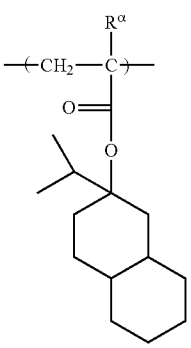 (a1-1-29)

(a1-1-30)
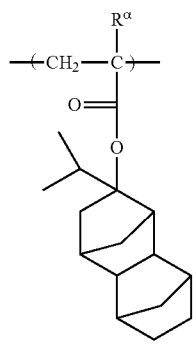
(a1-2-3)
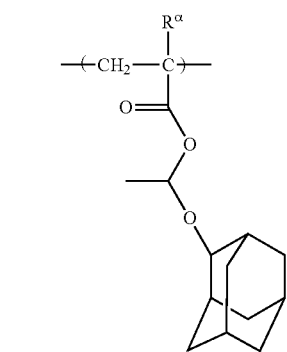
(a1-1-31)
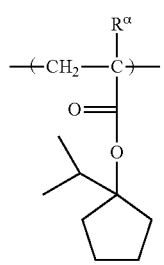
[Chemical Formula 31]
(a1-2-4)
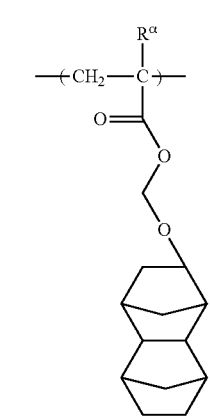
(a1-2-1)
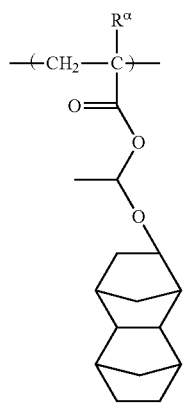
(a1-2-5)
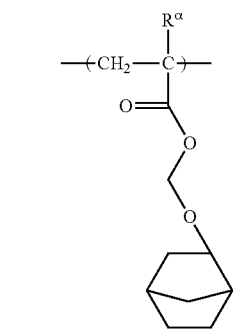
(a1-2-2)
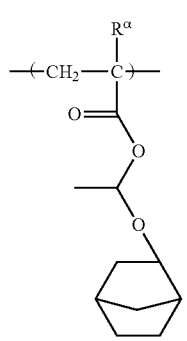
(a1-2-6)
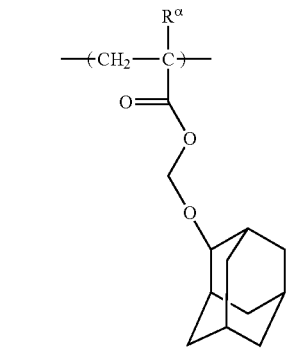

(a1-2-7)
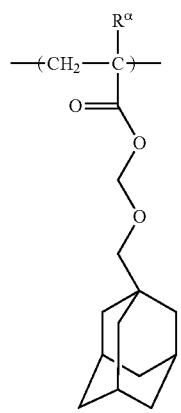
(a1-2-8)
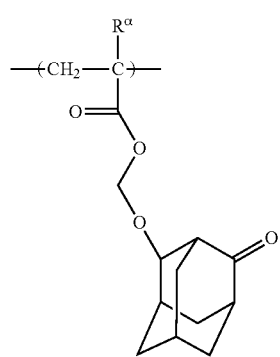
(a1-2-9)
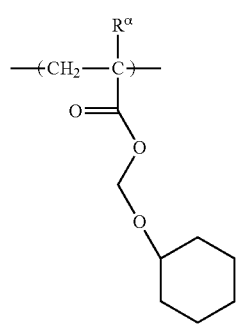
(a1-2-10)
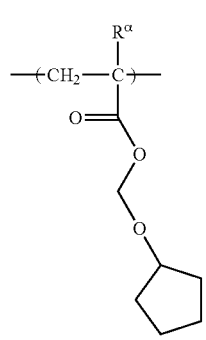
(a1-2-11)
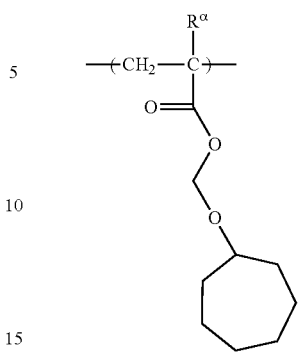
(a1-2-12)
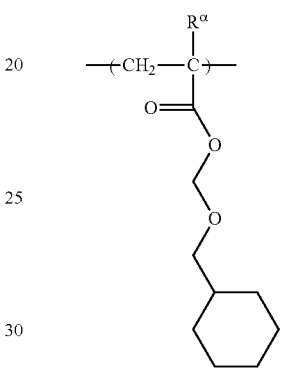
(a1-2-13)
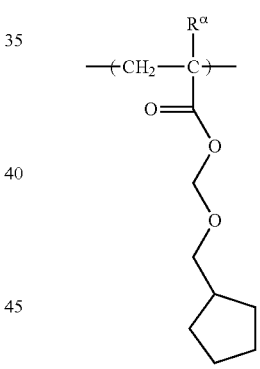
(a1-2-14)
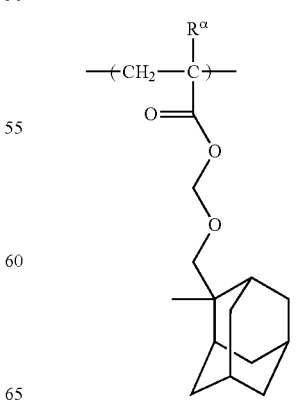

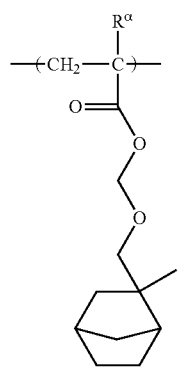
(a1-2-15)
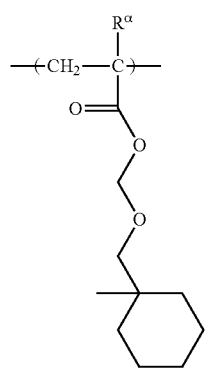
(a1-2-16)
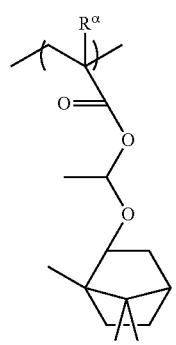
(a1-2-17)
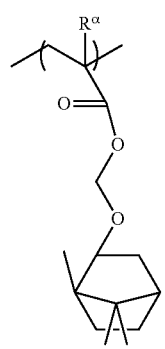
(a1-2-18)
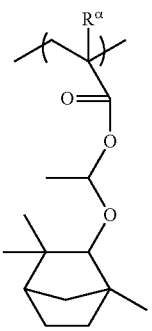
(a1-2-19)
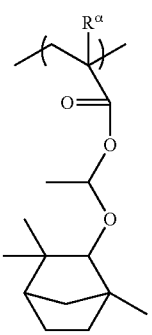
(a1-2-20)
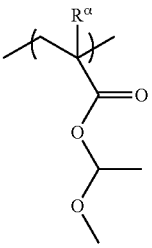
(a1-2-21)
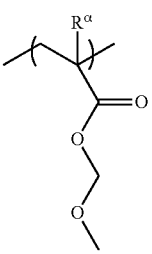
(a1-2-22)
(a1-2-23)

(a1-2-24) 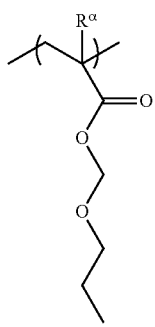
[Chemical Formula 32]
(a1-3-1) 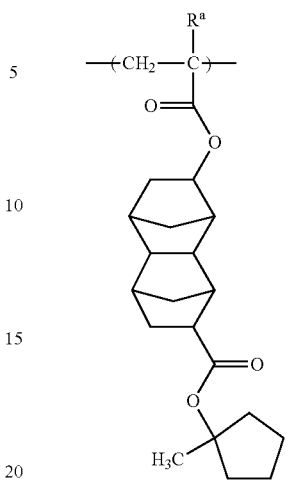
(a1-3-3)
(a1-3-4)
(a1-3-2) 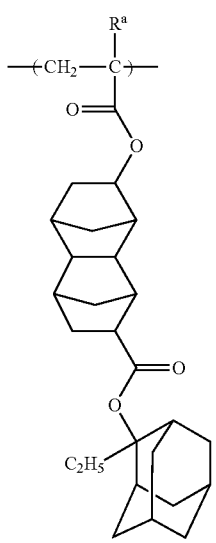
(a1-3-5) 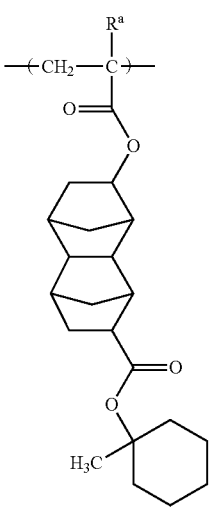
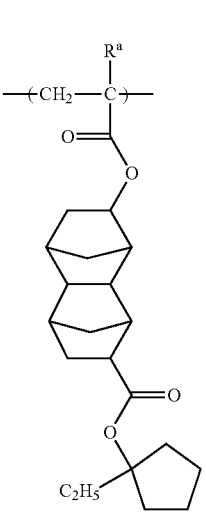

(a1-3-6)
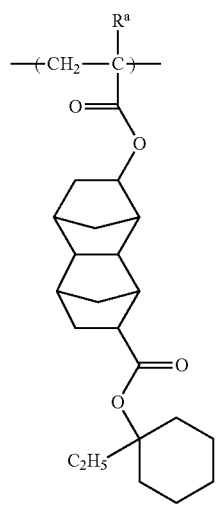
(a1-3-7)
(a1-3-8)
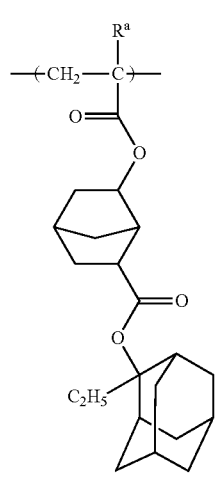
(a1-3-9)
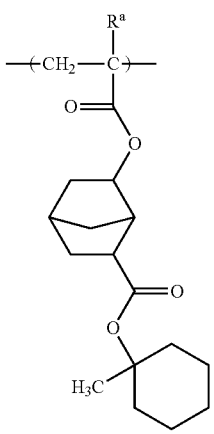
(a1-3-10)
(a1-3-11)
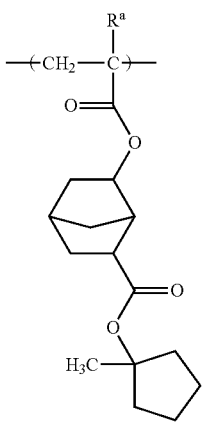

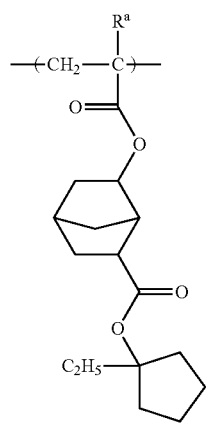 (a1-3-12)
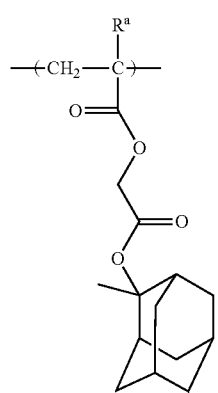 (a1-3-13)
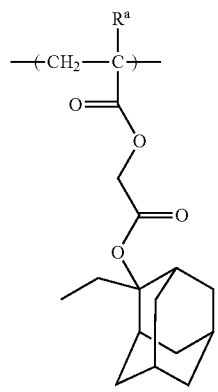 (a1-3-14)
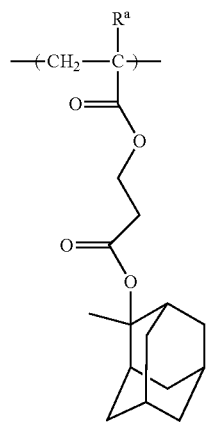 (a1-3-15)
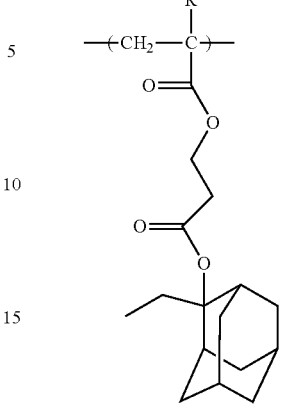 (a1-3-16)
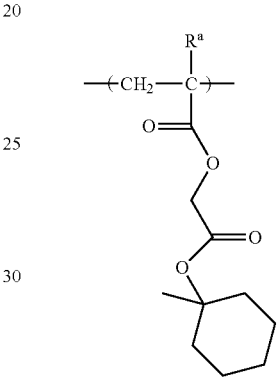 (a1-3-17)
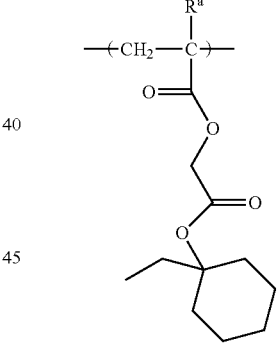 (a1-3-18)
[Chemical Formula 33]
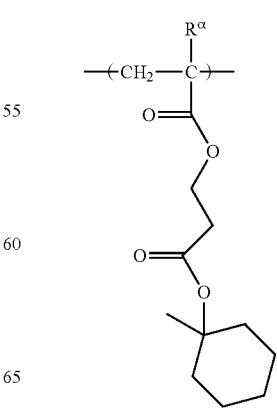 (a1-3-19)

(a1-3-20)
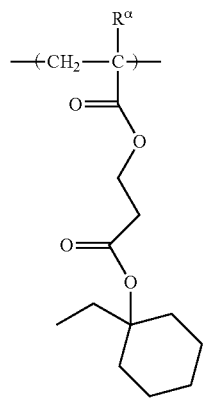
(a1-3-21)
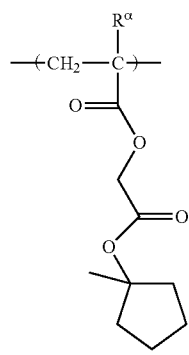
(a1-3-22)
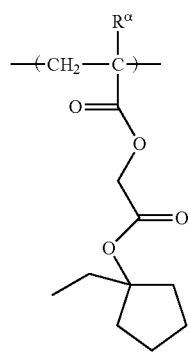
(a1-3-23)
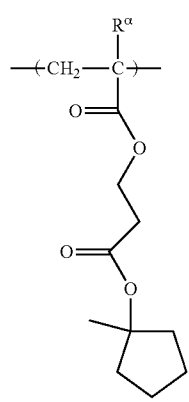
(a1-3-24)
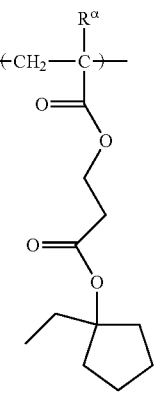
[Chemical Formula 34]
(a1-3-25)
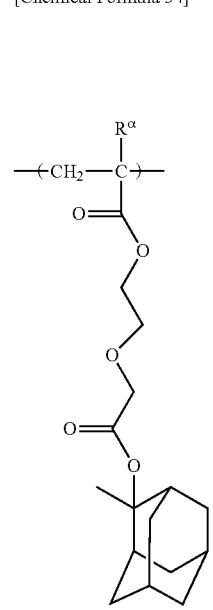
(a1-3-26)
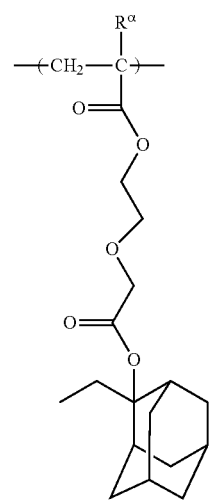

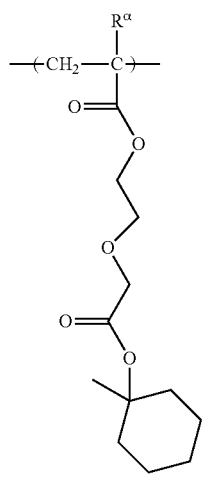
(a1-3-27)
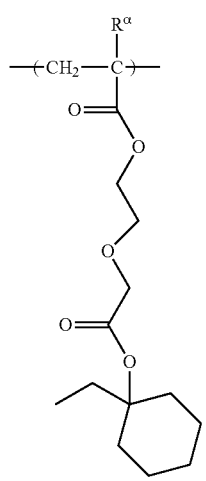
(a1-3-28)
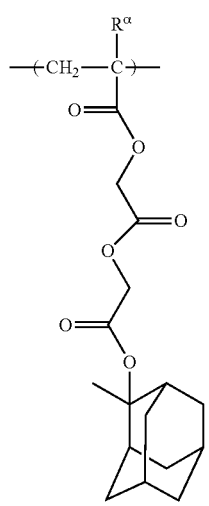
(a1-3-29)
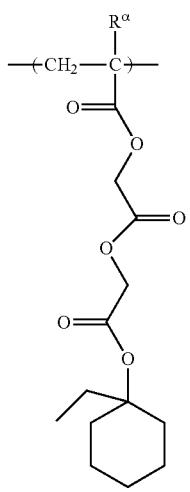
(a1-3-30)
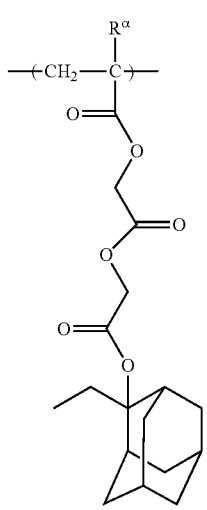
(a1-3-31)
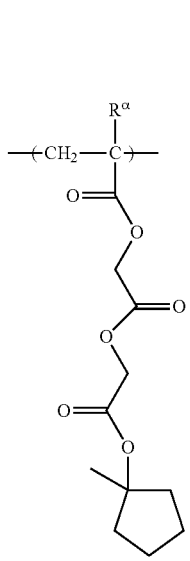
(a1-3-32)

[Chemical Formula 35]
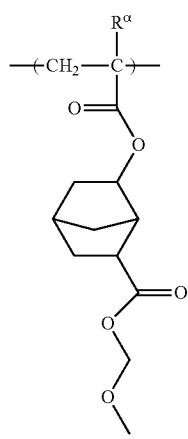
(a1-4-1)
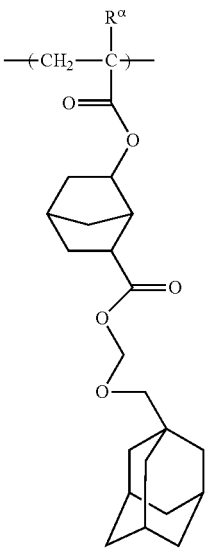
(a1-4-4)
(a1-4-2)
(a1-4-5)
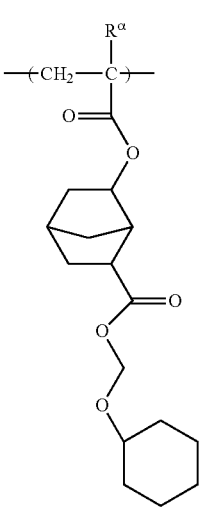
(a1-4-3)
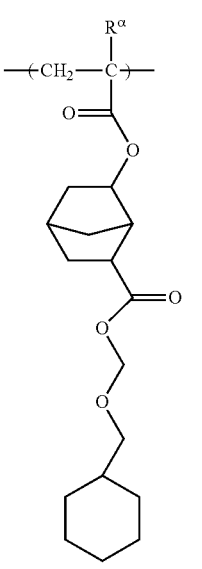
(a1-4-6)

(a1-4-7)
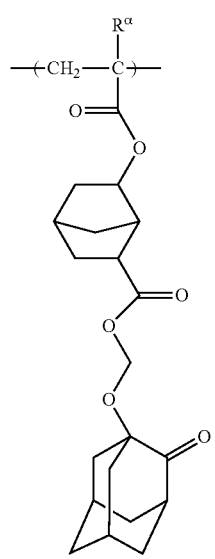
(a1-4-10)
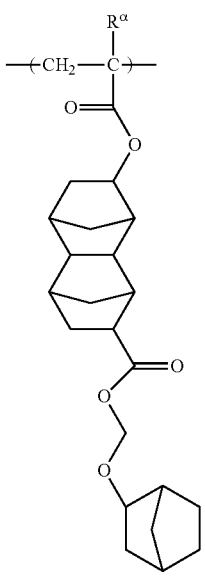
(a1-4-8)
(a1-4-9)
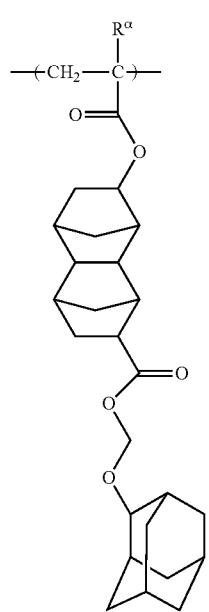
(a1-4-11)
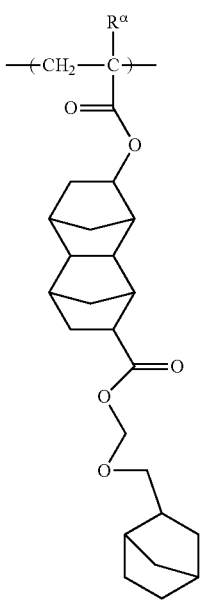

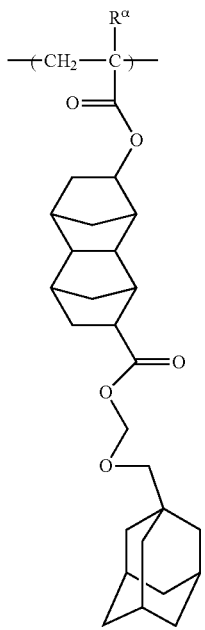

(a1-4-12)

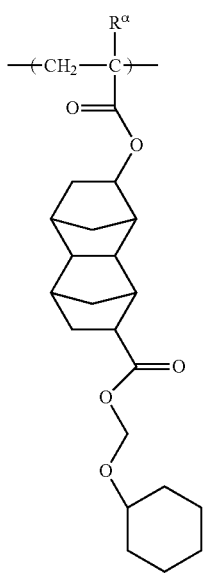

(a1-4-13)

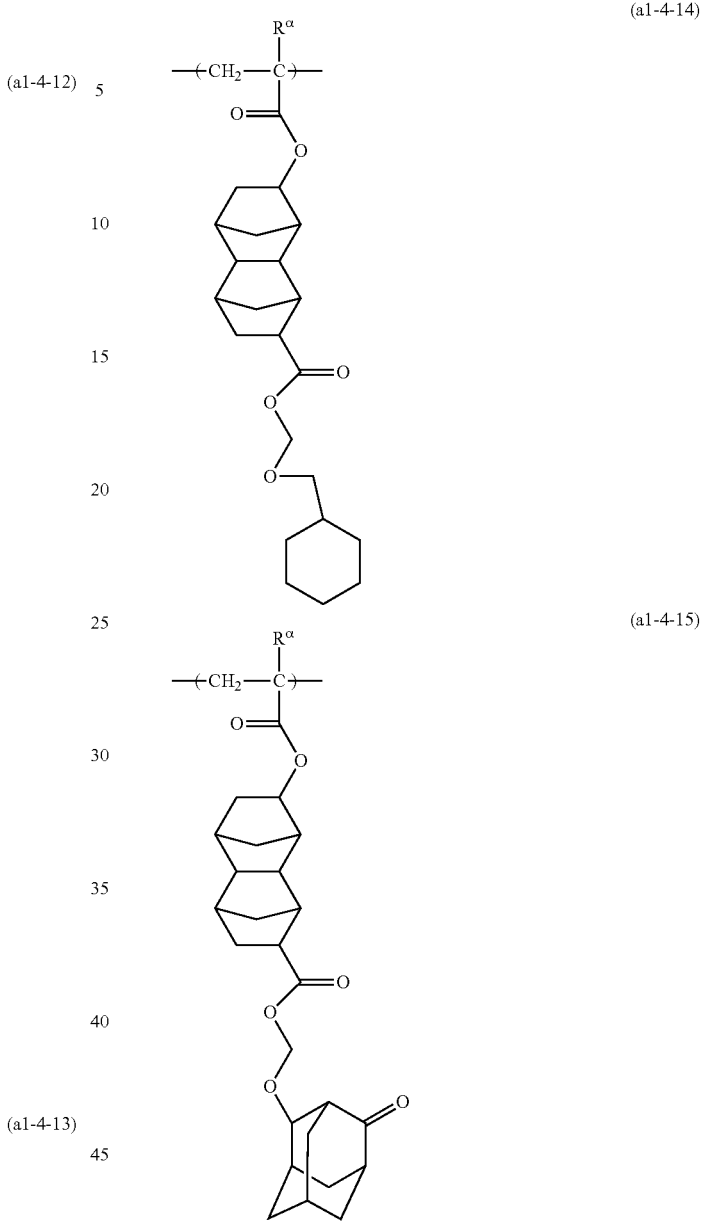

As the structural unit (a1), one type of structural unit may be used, or two or more types may be used in combination.

As the structural unit (a1), a structural units represented by general formula (a1-1) or (a1-3) are preferable. More specifically, at least one structural unit selected from the group consisting of structural units represented by formulas (a1-1-1) to (a-1-1-4), (a1-1-20) to (a1-1-23) and (a1-3-25) to (a1-3-32) is more preferable.

Further, as the structural unit (a1), structural units represented by general formula (a1-1-01) shown below which includes the structural units represented by formulas (a1-1-1) to (a1-1-3), structural units represented by general formula (a1-1-02) shown below which includes the structural units represented by formulas (a1-1-16) to (a1-1-18), (a1-1-20) to (a1-1-23), (a1-1-27) and (a1-1-31), structural units represented by general formula (a1-3-01) shown below which include the structural units represented by formulas (a1-3-25) to (a1-3-26), structural units represented by general formula (a1-3-02) shown below which include the structural units represented by formulas (a1-3-27) and (a1-3-28), and structural units represented by general formula (a1-3-03) shown below which include the structural units represented by formulas (a1-3-29) to (a1-3-32) are also preferable.

[Chemical Formula 36]

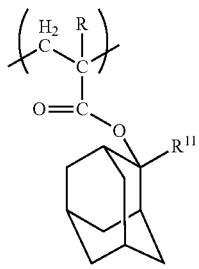

(a1-1-01)

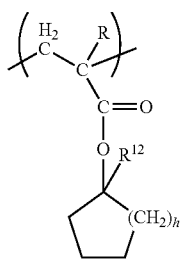

(a1-1-02)

In the formulas, R represents a hydrogen atom, an alkyl group of 1 to 5 carbon atoms or a halogenated alkyl group of 1 to 5 carbon atoms; $R^{11}$ represents an alkyl group of 1 to 5 carbon atoms; $R^{12}$ represents an alkyl group of 1 to 5 carbon atoms; and h represents an integer of 1 to 6.

In general formula (a1-1-01), R is the same as defined above.

The alkyl group for $R^{11}$ is the same as the alkyl group for R above, and a methyl group, an ethyl group or an isopropyl group is preferable.

In general formula (a1-1-02), R is as defined above.

The alkyl group for $R^{12}$ is the same as the alkyl group for R above, and a methyl group, an ethyl group or an isopropyl group is preferable.

h is preferably 1 or 2, and most preferably 2.

[Chemical Formula 37]

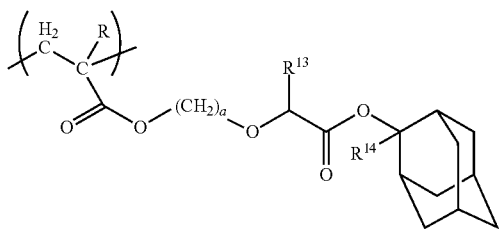

(a1-3-01)

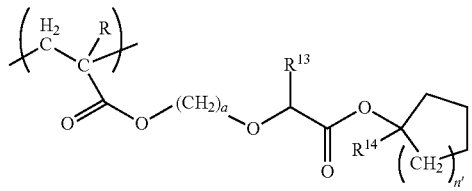

(a1-3-02)

In the formulas, R represents a hydrogen atom, an alkyl group of 1 to 5 carbon atoms or a halogenated alkyl group of 1 to 5 carbon atoms; $R^{14}$ represents an alkyl group of 1 to 5 carbon atoms; $R^{13}$ represents a hydrogen atom or a methyl group; a represents an integer of 1 to 10; and n' represents an integer of 1 to 6.

In general formulas (a1-3-01) and (a1-3-02), R is the same as defined above.

$R^{13}$ is preferably a hydrogen atom.

The alkyl group for $R^{14}$ is the same as the alkyl group for $R^{14}$ in the aforementioned formulas (I-1) to (1-9), and is preferably a methyl group, an ethyl group or an isopropyl group.

a is preferably an integer of 1 to 8, more preferably 2 to 5, and most preferably 2.

n' is most preferably 1 or 2.

[Chemical Formula 38]

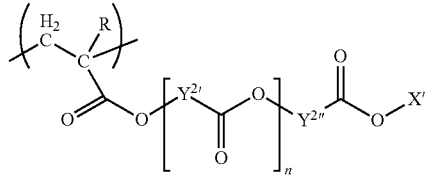

(a1-3-03)

In the formula, R is as defined above; each of $Y^{2'}$ and $Y^{2''}$ independently represents a divalent linking group; X' represents an acid dissociable, dissolution inhibiting group; and n represents an integer of 0 to 3.

In general formula (a1-3-03), as the divalent linking group for $Y^{2'}$ and $Y^{2''}$, the same groups as those described above for $Y^2$ in general formula (a1-3) can be given.

As $Y^{2'}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As $Y^{2''}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As the acid dissociable, dissolution inhibiting group for X', the same groups as those described above can be used. X is preferably a tertiary alkyl ester-type acid dissociable, dissolution inhibiting group, more preferably the aforementioned group (i) which has a tertiary carbon atom on the ring structure of a monovalent aliphatic cyclic group. Among the aforementioned groups (i), a group represented by general formula (I-1) above is preferable.

n represents an integer of 0 to 3, preferably an integer of 0 to 2, more preferably 0 or 1, and most preferably 1.

In the component (A1), the amount of the structural unit (a1) based on the combined total of all structural units constituting the component (A1) is preferably 5 to 90 mol %, more preferably 10 to 70 mol %, and still more preferably 20 to 50 mol %. When the amount of the structural unit (a1) is at least as large as the lower limit of the above-mentioned range, a pattern can be easily formed using a resist composition prepared from the component (A1). On the other hand, when the amount of the structural unit (a1) is no more than the upper limit of the above-mentioned range, a good balance can be achieved with the other structural units.

[Structural Unit (a2)]

The structural unit (a2) is at least one structural unit selected from the group consisting of a structural unit derived from an acrylate ester containing a —SO$_2$— containing cyclic group (hereafter, referred to as "structural unit (a2$^S$)") and a structural unit derived from an acrylate ester containing a lactone-containing cyclic group (hereafter, referred to as "structural unit (a2$^L$)").

When the structural unit represented by the aforementioned general formula (a0) has a —SO$_2$-containing cyclic group or a lactone-containing cyclic group, the structural unit is regarded as a structural unit (a0), and but is not regarded as a structural unit (a2).

Structural Unit (a2$^S$):

The structural unit (a2$^S$) is a structural unit derived from an acrylate ester containing a —SO$_2$— containing cyclic group.

As described above, an "—SO$_2$— containing cyclic group" refers to a cyclic group having a ring containing —SO$_2$— within the ring structure thereof, i.e., a cyclic group in which the sulfur atom (S) within —SO$_2$— forms part of the ring skeleton of the cyclic group. The ring containing —SO$_2$— within the ring skeleton thereof is counted as the first ring. A cyclic group in which the only ring structure is the ring that contains —SO$_2$— in the ring skeleton thereof is referred to as a monocyclic group, and a group containing other ring structures is described as a polycyclic group regardless of the structure of the other rings. The —SO$_2$— containing cyclic group may be either a monocyclic group or a polycyclic group.

As the —SO$_2$— containing cyclic group, a cyclic group containing —O—SO$_2$— within the ring skeleton thereof, i.e., a cyclic group containing a sultone ring in which —O—S— within the —O—SO$_2$— group forms part of the ring skeleton thereof is particularly desirable.

The —SO$_2$— containing cyclic group preferably has 3 to 30 carbon atoms, more preferably 4 to 20, still more preferably 4 to 15, and most preferably 4 to 12. Herein, the number of carbon atoms refers to the number of carbon atoms constituting the ring skeleton, excluding the number of carbon atoms within a substituent.

The —SO$_2$— containing cyclic group may be either a —SO$_2$— containing aliphatic cyclic group or a —SO$_2$— containing aromatic cyclic group. A —SO$_2$— containing aliphatic cyclic group is preferable.

Examples of the —SO$_2$— containing aliphatic cyclic group include aliphatic cyclic groups in which part of the carbon atoms constituting the ring skeleton has been substituted with a —SO$_2$— group or a —O—SO$_2$— group and has at least one hydrogen atom removed from the aliphatic hydrocarbon ring. Specific examples include an aliphatic hydrocarbon ring in which a —CH$_2$— group constituting the ring skeleton thereof has been substituted with a —SO$_2$— group and has at least one hydrogen atom removed therefrom; and an aliphatic hydrocarbon ring in which a —CH$_2$—CH$_2$— group constituting the ring skeleton has been substituted with a —O—SO$_2$— group and has at least one hydrogen atom removed therefrom.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The —SO$_2$— containing cyclic group may have a substituent. Examples of the substituents include an alkyl group, an alkoxy group, a halogen atom, a hydroxy group, an oxygen atom, a halogenated alkyl group, a halogenated alkoxy group, a hydroxyalkyl group, —C(=O)—R$^{80}$ [R$^{80}$ represents an alkyl group], —COOR$^{81}$ [R$^{81}$ represents a hydrogen atom or an alkyl group], —OC(=O)R$^{81}$ [R$^{81}$ represents a hydrogen atom or an alkyl group], a cyano group, an amino group, an amido group, a nitro group, a sulfur atom and a sulfonyl group (SO$_2$).

Among these, as the alkyl group, alkoxy group, halogen atom, halogenated alkyl group, halogenated alkoxy group, hydroxyalkyl group, —C(=O)—R$^{80}$, —COOR$^{81}$ and —OC(=O)R$^{81}$, the same groups as the aforementioned substituent groups with which part or all of the hydrogen atoms within an aliphatic cyclic group may be substituted, in relation to R$^5$ in the formula (a0) represented by the formula (1), can be used.

As the substituent for —SO$_2$-containing cyclic group, an alkyl group, an alkoxy group, a halogen atom, a hydroxy group, an oxygen atom (=O), a halogenated alkyl group, a hydroxyalkyl group, —COOR$^{81}$, —OC(=O)R$^{81}$ and a cyano group are preferable.

More specific examples of the —SO$_2$— containing cyclic group include groups represented by general formulas (3-1) to (3-4) shown below.

[Chemical Formula 39]

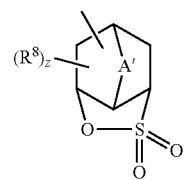

(3-1)

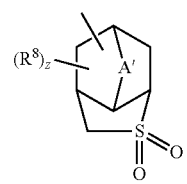

(3-2)

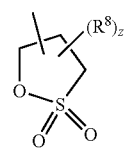

(3-3)

-continued (3-4)

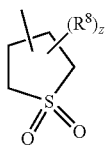

In the formulas, A' represents an oxygen atom, a sulfur atom or an alkylene group of 1 to 5 carbon atoms which may contain an oxygen atom or a sulfur atom; z represents an integer of 0 to 2; and $R^8$ represents an alkyl group, an alkoxy group, a halogen atom, a hydroxy group, an oxygen atom (=O), a halogenated alkyl group, a hydroxyalkyl group, —COOR$^{81}$, —OC(=O)$^{81}$ or a cyano group, wherein $R^{81}$ represents a hydrogen atom or an alkyl group.

In general formulas (3-1) to (3-4) above, A' represents an oxygen atom (—O—), a sulfur atom (—S—) or an alkylene group of 1 to 5 carbon atoms which may contain an oxygen atom or a sulfur atom.

As the alkylene group of 1 to 5 carbon atoms for A', a linear or branched alkylene group is preferable, and examples thereof include a methylene group, an ethylene group, an n-propylene group and an isopropylene group.

Examples of alkylene groups that contain an oxygen atom or a sulfur atom include the aforementioned alkylene groups in which —O— or —S— is bonded to the terminal of the alkylene group or interposed within the alkyl group. Specific examples of such alkylene groups include —O—CH$_2$—, —CH$_2$—O—CH$_2$—, —S—CH$_2$— and —CH$_2$S—CH$_2$—.

As A', an alkylene group of 1 to 5 carbon atoms or —O— is preferable, more preferably an alkylene group of 1 to 5 carbon atoms, and most preferably a methylene group.

z represents an integer of 0 to 2, and is most preferably 0.

When z is 2, the plurality of $R^8$ may be the same or different from each other.

As the alkyl group, alkoxy group, halogen atom, halogenated alkyl group, hydroxyalkyl group, —COOR$^{81}$ and —OC(=O)R$^{81}$ for $R^8$, the same alkyl groups, alkoxy groups, halogenated alkyl groups, —COOR$_{81}$, —OC(=O)R$^{81}$ and hydroxyalkyl groups as those described above as the substituent for the —SO$_2$— containing cyclic group can be mentioned.

Specific examples of the cyclic groups represented by general formulas (3-1) to (3-4) are shown below. In the formulas shown below, "AC" represents an acetyl group.

[Chemical Formula 40]

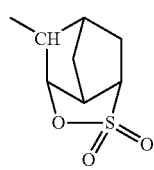

(3-1-1)

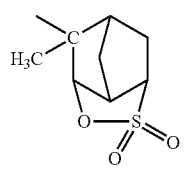

(3-1-2)

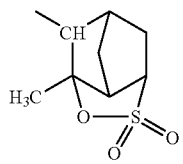

(3-1-3)

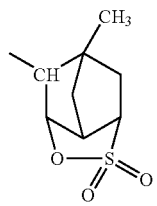

(3-1-4)

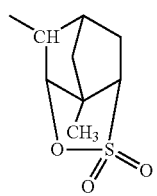

(3-1-5)

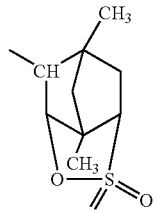

(3-1-6)

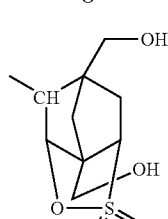

(3-1-7)

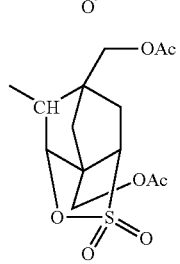

(3-1-8)

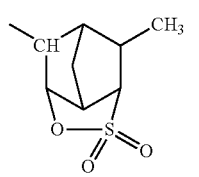

(3-1-9)

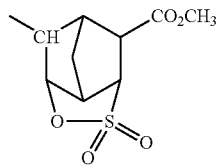

(3-1-10)

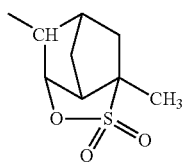 (3-1-11)
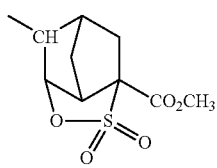 (3-1-12)
[Chemical Formula 41]
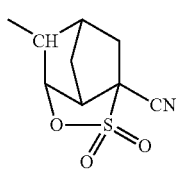 (3-1-13)
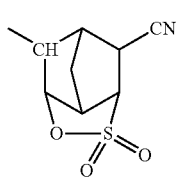 (3-1-14)
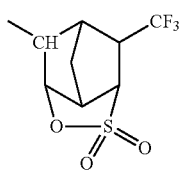 (3-1-15)
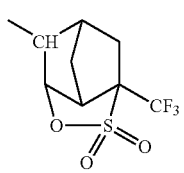 (3-1-16)
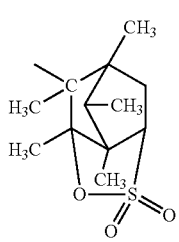 (3-1-17)
[Chemical Formula 42]
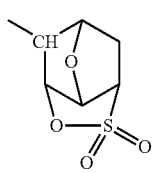 (3-1-18)
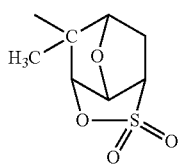 (3-1-19)
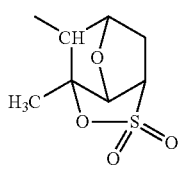 (3-1-20)
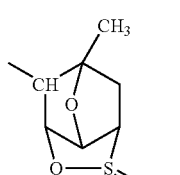 (3-1-21)
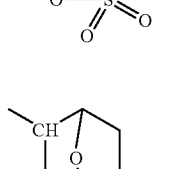 (3-1-22)
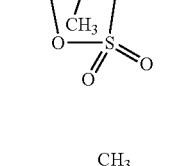 (3-1-23)
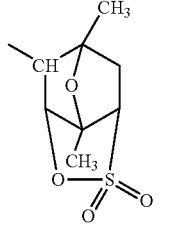 (3-1-24)
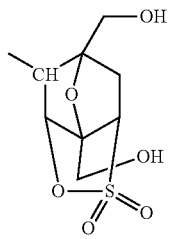 (3-1-25)

[Chemical Formula 43]

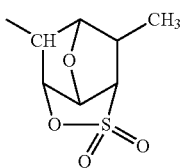
(3-1-26)

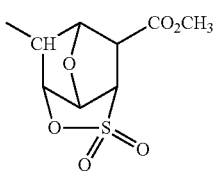
(3-1-27)

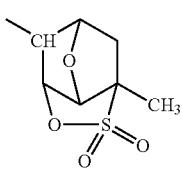
(3-1-28)

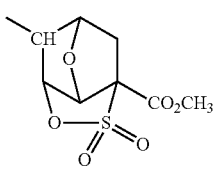
(3-1-29)

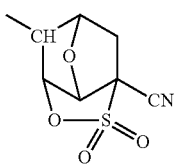
(3-1-30)

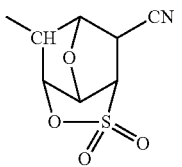
(3-1-31)

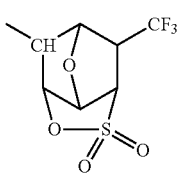
(3-1-32)

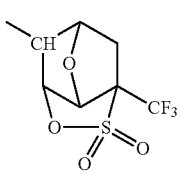
(3-1-33)

[Chemical Formula 44]

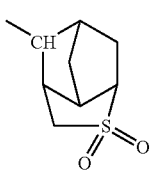
(3-2-1)

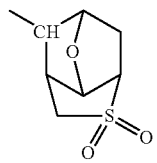
(3-2-2)

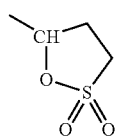
(3-3-1)

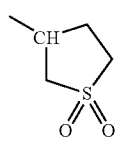
(3-4-1)

As the —$SO_2$— containing cyclic group, a group represented by the aforementioned general formula (3-1) is preferable, at least one member selected from the group consisting of groups represented by the aforementioned chemical formulas (3-1-1), (3-1-18), (3-3-1) and (3-4-1) is more preferable, and a group represented by chemical formula (3-1-1) is most preferable.

More specific examples of the structural unit ($a2^S$) include structural units represented by general formula (a2-6) shown below.

[Chemical Formula 45]

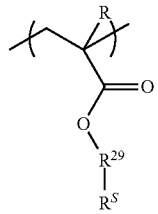
(a2-6)

In the formula, R represents a hydrogen atom, an alkyl group of 1 to 5 carbon atoms or a halogenated alkyl group of 1 to 5 carbon atoms; $R^S$ represents a —$SO_2$-containing cyclic group; and $R^{29}$ represents a single bond or a divalent linking group.

In genera formula (a2-6), R is the same as defined above. $R^S$ is the same as defined for the aforementioned —$SO_2$— containing group.

$R^{29}$ may be either a single bond or a divalent linking group. In terms of the effects of the present invention, a divalent linking group is preferable.

As examples of the divalent linking group for $R^{29}$, the same divalent linking groups as those described above for the $L^1$ in the aforementioned formula (a0) can be mentioned. Among these, an alkylene group or a divalent linking group containing an ester bond (—C(=O)—O—) is preferable.

As the alkylene group, a linear or branched alkylene group is preferable. Specific examples include the same linear alkylene groups and branched alkylene groups as those described above for the aliphatic hydrocarbon group for $Y^2$.

As the divalent linking group containing an ester bond, a group represented by general formula: -$L^4$-C(=O)—O— (in the formula, L⁴ represents a divalent linking group) is particularly desirable. That is, the structural unit (a2$^S$) is preferably a structural unit represented by general formula (a2-6-1) shown below.

[Chemical Formula 46]

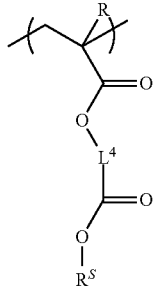

(a2-6-1)

In the formula, R and R$^s$ are the same as defined above; and L⁴ represents a divalent linking group.

L⁴ is not particularly limited. For example, the same divalent linking groups as those described for Y² in general formula (a1-0-2) explained above in relation to the structural unit (a1) can be mentioned.

As the divalent linking group for L⁴, an alkylene group, a divalent alicyclic hydrocarbon group or a divalent linking group containing a hetero atom is preferable.

As the linear or branched alkylene group, the divalent alicyclic hydrocarbon group and the divalent linking group containing a hetero atom, the same linear or branched alkylene group, divalent alicyclic hydrocarbon group and divalent linking group containing a hetero atom as those described above as preferable examples of Y² can be mentioned.

Among these, a linear or branched alkylene group, or a divalent linking group containing an oxygen atom as a hetero atom is more preferable.

The linear or branched alkylene group for L⁴ preferably has 1 to 10 carbon atoms, more preferably 1 to 8, and still more preferably 1 to 5. As the linear alkylene group, a methylene group or an ethylene group is preferable, and a methylene group is particularly desirable. As the branched alkylene group, an alkylmethylene group or an alkylethylene group is preferable, and —CH(CH₃)—, —C(CH₃)₂— or —C(CH₃)₂CH₂— is particularly desirable.

As the divalent linking group containing a hetero atom, a divalent linking group containing an ether bond or an ester bond is preferable, and a group represented by the aforementioned formula -A¹-O—B¹—, -A¹-O—C(=O)—B¹— or -[A¹-C(=O)—O]ₘ—B¹— is more preferable. Among these, a group represented by the formula -A¹-O—C(=O)—B¹— is preferable, and a group represented by the formula: —(CH₂)ₑ—C(=O)—O—(CH₂)_d— is particularly desirable. c represents an integer of 1 to 5, and preferably 1 or 2. d represents an integer of 1 to 5, and preferably 1 or 2.

In particular, as the structural unit (a2$^S$), a structural unit represented by general formula (a2-6-11) or (a2-6-12) shown below is preferable, and a structural unit represented by general formula (a2-6-12) shown below is more preferable.

[Chemical Formula 47]

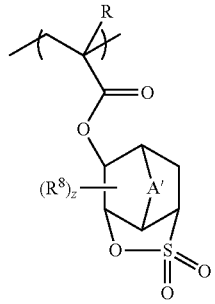

(a2-6-11)

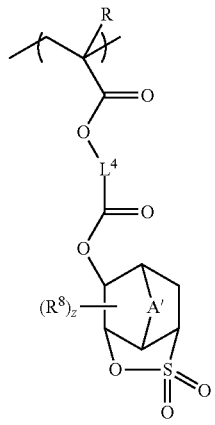

(a2-6-12)

In the formulas, R, A', R⁸ z and L⁴ are the same as defined above.

In general formula (a2-6-11), A' is preferably a methylene group, an oxygen atom (—O—) or a sulfur atom (—S—).

As L⁴, a linear or branched alkylene group or a divalent linking group containing an oxygen atom is preferable. As the linear or branched alkylene group and the divalent linking group containing an oxygen atom represented by L⁴, the same linear or branched alkylene groups and the divalent linking groups containing an oxygen atom as those described above can be mentioned.

As the structural unit represented by general formula (a2-6-12), a structural unit represented by general formula (a2-6-12a) or (a2-6-12b) shown below is particularly desirable.

[Chemical Formula 48]

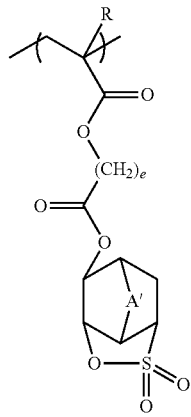

(a2-6-12a)

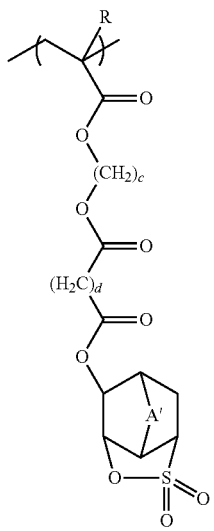

(a2-6-12b)

In the formulas, R and A' are the same as defined above; and each of c to e independently represents an integer of 1 to 3.

Structural Unit (a2$^L$):

The structural unit (a2$^L$) is a structural unit derived from an acrylate ester containing a lactone-containing cyclic group.

As described above, the term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2$^L$) is effective in improving the adhesion between the resist film and the substrate, and increasing the compatibility with the developing solution containing water.

The lactone-containing cyclic group for the structural unit (a2$^L$) is not particularly limited, and an arbitrary structural unit may be used. Specific examples of lactone-containing monocyclic groups include a group in which one hydrogen atom has been removed from a 4- to 6-membered lactone ring, such as a group in which one hydrogen atom has been removed from β-propionolatone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

The lactone-containing cyclic group may have a substituent. Examples of the substituents include an alkyl group, an alkoxy group, a halogen atom, a hydroxy group, an oxygen atom, a halogenated alkyl group, a halogenated alkoxy group, a hydroxyalkyl group, —C(=O)—R$^{80}$ [R$^{80}$ represents an alkyl group], —COOR$^{81}$ [R$^{81}$ represents a hydrogen atom or an alkyl group], —OC(=O)R$^{81}$ [R$^{81}$ represents a hydrogen atom or an alkyl group], a cyano group, an amino group, an amido group, a nitro group, a sulfur atom and a sulfonyl group (SO$_2$).

Among these, as the alkyl group, alkoxy group, halogen atom, halogenated alkyl group, halogenated alkoxy group, hydroxyalkyl group, —C(=O)—R$^{80}$, —COOR$^{81}$ and —OC(=O)R$^{81}$ for the hetero atom-containing substituent, the same groups as the aforementioned substituent groups with which part or all of the hydrogen atoms within an aliphatic cyclic group may be substituted, in relation to R$^5$ in the formula (a0) represented by the formula (1), can be used.

As the substituent for the lactone-containing cyclic group, an alkyl group of 1 to 5 carbon atoms, an alkoxy group of 1 to 5 carbon atoms or —COOR" [R" represents a hydrogen atom or an alkyl group] is preferable. As the alkyl group, alkoxy group and —COOR", the same alkyl group, alkoxy group or —COOR" for W in general formulas (a2-1) to (a2-5) described later can be mentioned.

Examples of the structural unit (a2$^L$) include structural units represented by the aforementioned general formula (a2-6) in which the R$^S$ group has been substituted with a lactone-containing cyclic group. Specific examples include structural units represented by general formulas (a2-1) to (a2-5) shown below.

[Chemical Formula 49]

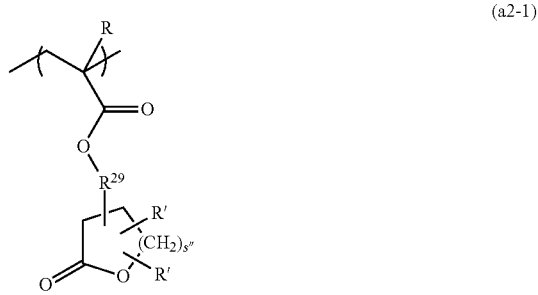

(a2-1)

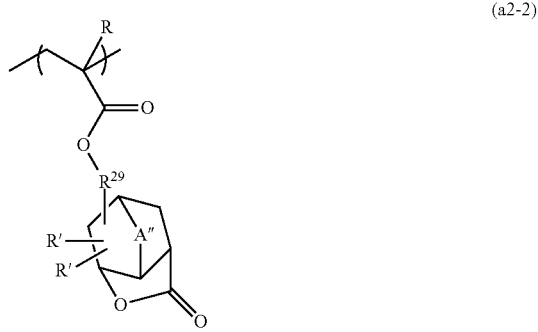

(a2-2)

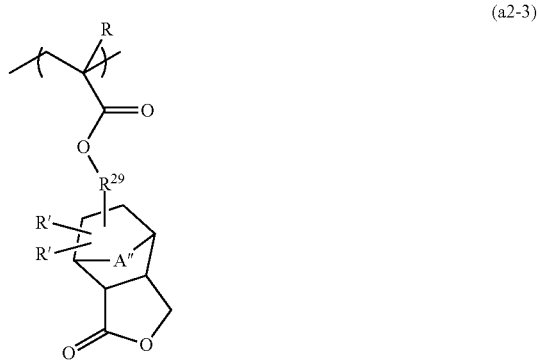

(a2-3)

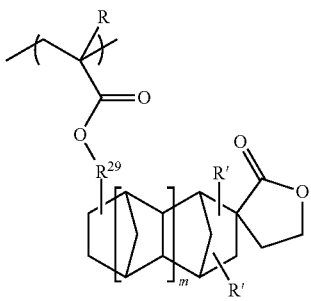

(a2-4)

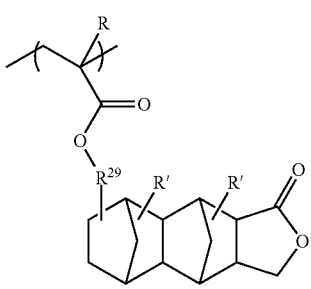

(a2-5)

In the formulas, R represents a hydrogen atom, an alkyl group of 1 to 5 carbon atoms or a halogenated alkyl group of 1 to 5 carbon atoms; each R' independently represents a hydrogen atom, an alkyl group of 1 to 5 carbon atoms, an alkoxy group of 1 to 5 carbon atoms or —COOR", wherein R" represents a hydrogen atom or an alkyl group; $R^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as R in the structural unit (a1).

Examples of the alkyl group of 1 to 5 carbon atoms for R' include a methyl group, an ethyl group, a propyl group, an n-butyl group and a tert-butyl group.

Examples of the alkoxy group of 1 to 5 carbon atoms for R' include a methoxy group, an ethoxy group, an n-propoxy group, an iso-propoxy group, an n-butoxy group and a tert-butoxy group.

In terms of industrial availability, R' is preferably a hydrogen atom.

The alkyl group for R" may be any of linear, branched or cyclic.

When R" is a linear or branched alkyl group, it preferably has 1 to 10 carbon atoms, more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

A" is preferably an alkylene group of 1 to 5 carbon atoms, an oxygen atom (—O—) or a sulfur atom (—S—), and more preferably an alkylene group of 1 to 5 carbon atoms or —O—. As the alkylene group of 1 to 5 carbon atoms, a methylene group or a dimethylethylene group is preferable, and a methylene group is particularly desirable.

$R^{29}$ is the same as defined for $R^{29}$ in the aforementioned general formula (a2-6).

In formula (a2-1), s" is preferably 1 or 2.

Specific examples of structural units represented by general formulas (a2-1) to (a2-5) are shown below. In the formulas shown below, $R^\alpha$ represents a hydrogen atom, a methyl group or a trifluoromethyl group.

[Chemical Formula 50]

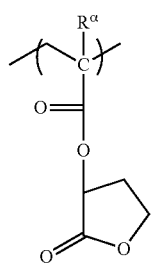

(a2-1-1)

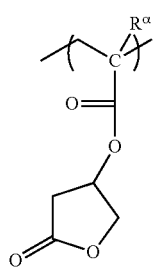

(a2-1-2)

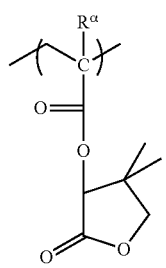

(a2-1-3)

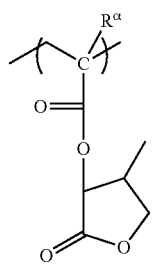

(a2-1-4)

-continued
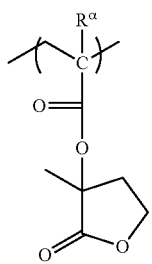 (a2-1-5)
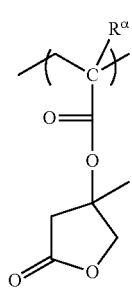 (a2-1-6)
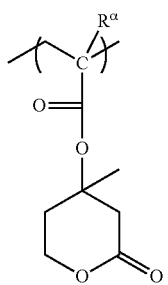 (a2-1-7)
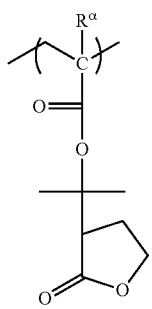 (a2-1-8)
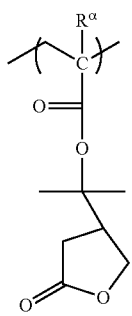 (a2-1-9)
-continued
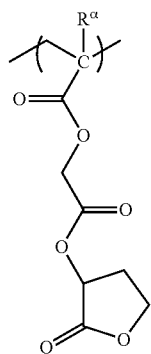 (a2-1-10)
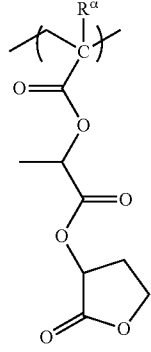 (a2-1-11)
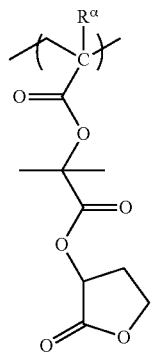 (a2-1-12)
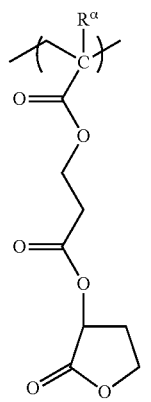 (a2-1-13)

[Chemical Formula 51]
(a2-2-1) 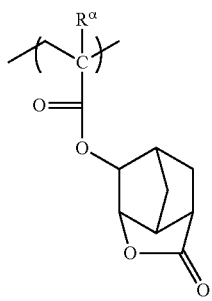
(a2-2-2) 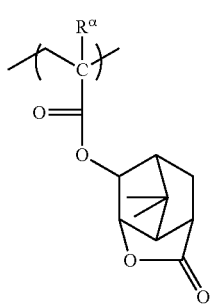
(a2-2-3) 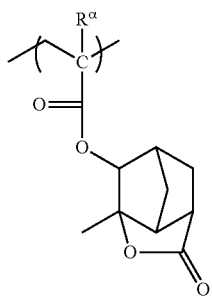
(a2-2-4) 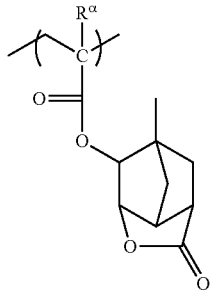
(a2-2-5) 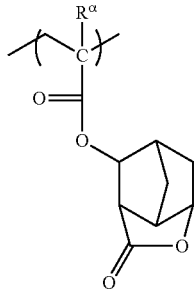
(a2-2-6) 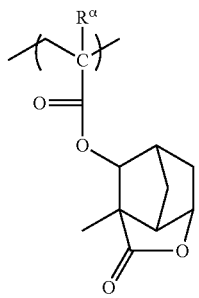
(a2-2-7) 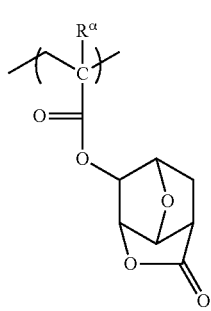
(a2-2-8) 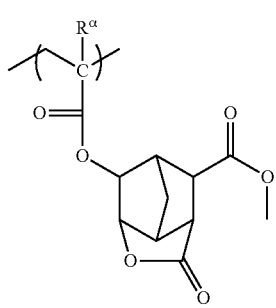
(a2-2-9) 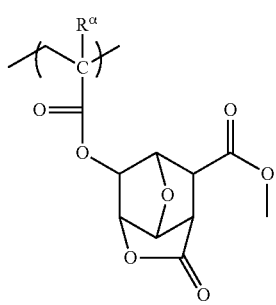
(a2-2-10) 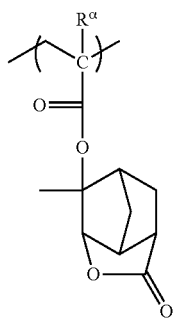

(a2-2-11) 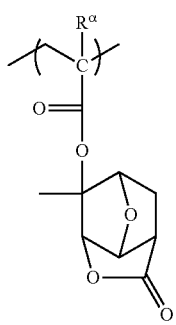
(a2-2-12) 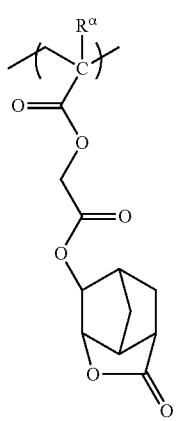
(a2-2-13) 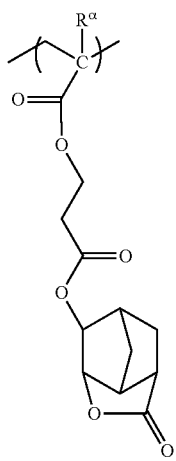
(a2-2-14) 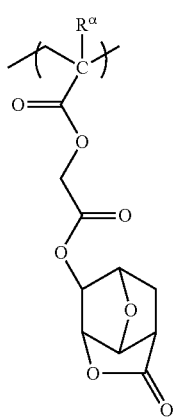
(a2-2-15) 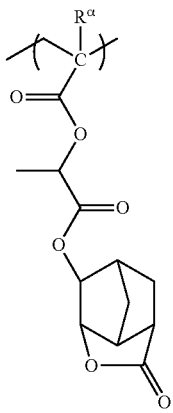
(a2-2-16) 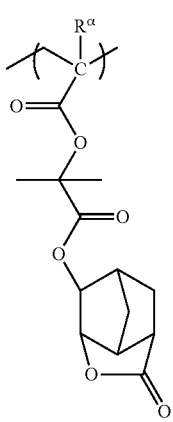
(a2-2-17) 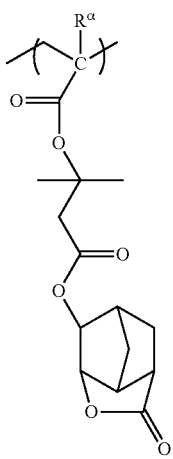
[Chemical Formula 52]
(a2-3-1) 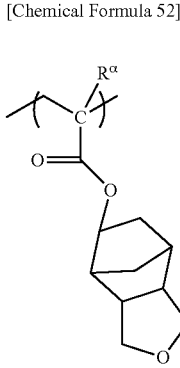

(a2-3-2)
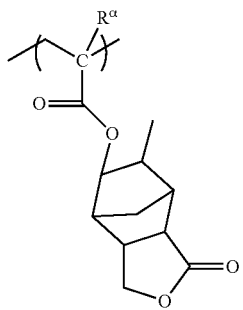
(a2-3-3)
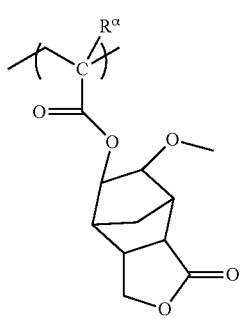
(a2-3-4)
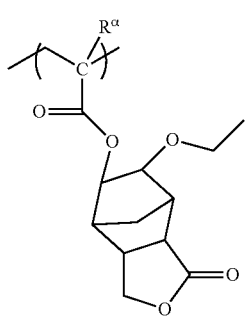
(a2-3-5)
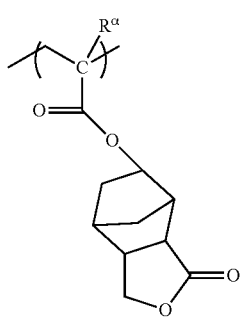
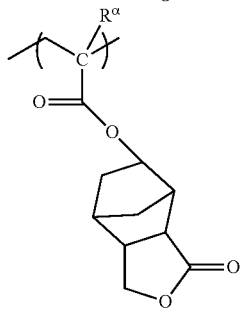
[Chemical Formula 53]
(a2-4-1)
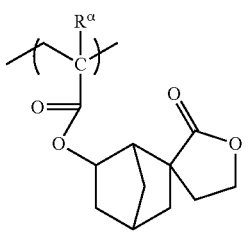
(a2-4-2)
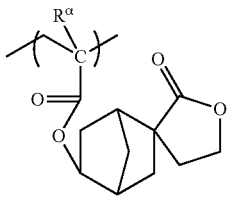
(a2-4-3)
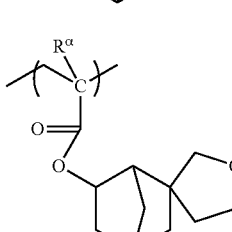
(a2-4-4)
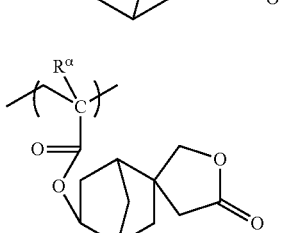
(a2-4-5)
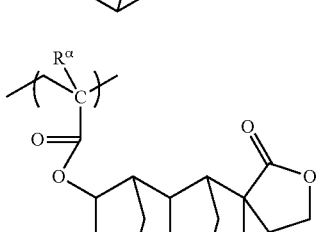
(a2-4-6)
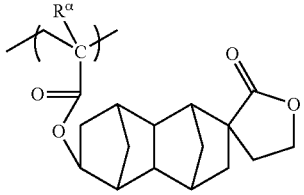
(a2-4-7)
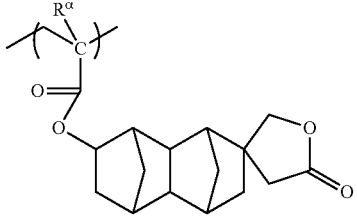

-continued
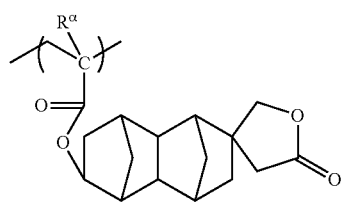
(a2-4-8)
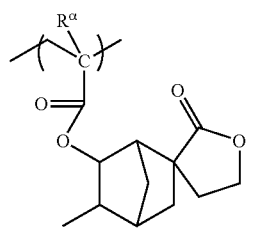
(a2-4-9)
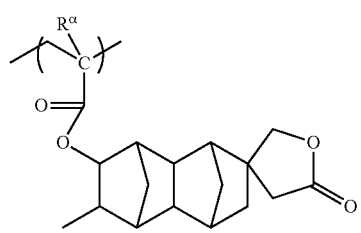
(a2-4-10)
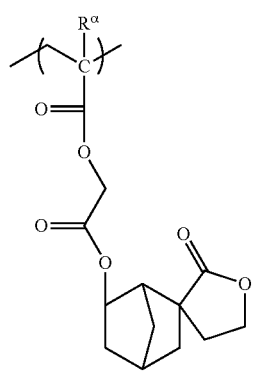
(a2-4-11)
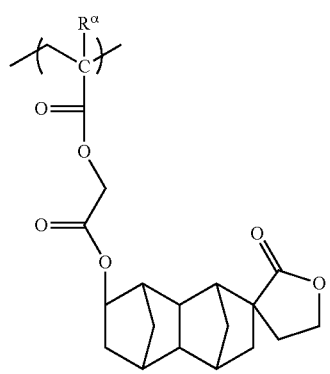
(a2-4-12)
[Chemical Formula 54]
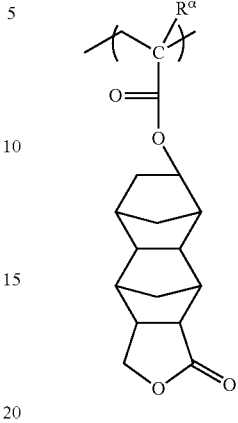
(a2-5-1)
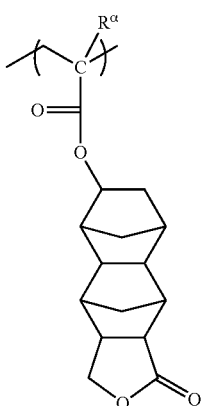
(a2-5-2)
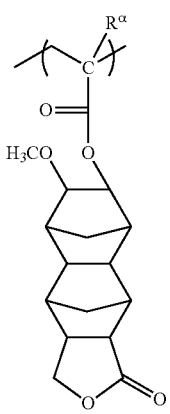
(a2-5-3)

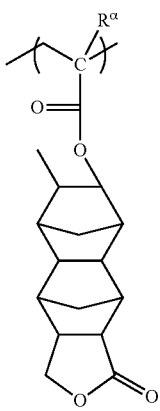

(a2-5-4)

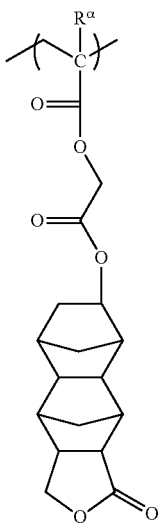

(a2-5-5)

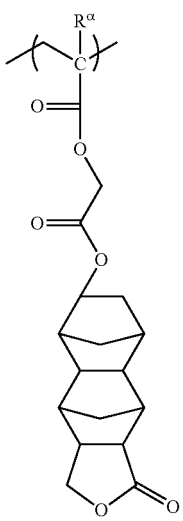

(a2-5-6)

In the component (A1), as the structural unit (a2), one type of structural unit may be used, or two or more types may be used in combination. For example, as the structural unit (a2), a structural unit (a2$^S$) may be used alone, or a structural unit (a2$^L$), or a combination of these structural units may be used. Further, as the structural unit (a2$^S$) or the structural unit (a2$^L$), either a single type of structural unit may be used, or two or more types may be used in combination.

As the structural unit (a2), at least one structural unit selected from the group consisting of formulas (a2-1) to (a2-6) is preferable, and at least one structural unit selected from the group consisting of formulas (a2-1) to (a2-3) and (a2-6) is more preferable. Specifically, it is preferable to use at least one structural unit selected from the group consisting of formulas (a2-1-1), (a2-2-1), (a2-2-7), (a2-3-1), (a2-3-5) and (a2-6-1).

In the component (A1), the amount of the structural unit (a2) based on the combined total of all structural units constituting the component (A1) is preferably 5 to 60 mol %, more preferably 10 to 50 mol %, and still more preferably 20 to 50 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units.

[Structural Unit (a3)]

The structural unit (a3) is a structural unit derived from an acrylate ester containing a polar group-containing aliphatic hydrocarbon group. When the component (A1) includes the structural unit (a3), the hydrophilicity of the component (A1) is improved, and hence, the compatibility of the component (A1) with the developing solution is improved. As a result, the alkali solubility of the exposed portions improves, which contributes to favorable improvements in the resolution.

Examples of the polar group include a hydroxy group, a cyano group, a carboxy group and a fluorinated alcohol group (a hydroxyalkyl group in which part of the hydrogen atoms bonded to carbon atoms have been substituted with fluorine atoms). Among these, a hydroxy group or a carboxy group is preferable, and a hydroxy group is particularly desirable.

In the structural unit (a3), the number of polar groups bonded to the aliphatic hydrocarbon group is not particularly limited, although 1 to 3 groups is preferable, and 1 group is particularly desirable.

The aliphatic hydrocarbon group to which the polar group is bonded may be either saturated or unsaturated, preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 12 carbon atoms, more preferably 1 to 10, still more preferably 1 to 8, and still more preferably 1 to 6.

The linear or branched aliphatic hydrocarbon group may have part or all of the hydrogen atoms substituted with a substituent other than a polar group. Examples of the substituent include a fluorine atom, a fluorinated alkyl group of 1 to 5 carbon atoms, and an oxygen atom (═O). Further, the linear or branched aliphatic hydrocarbon group may have a divalent group containing a hetero atom present between the carbon atoms. Examples of the "divalent group containing a hetero atom" include the same groups as those described for the "divalent linking group containing a hetero atom" as the divalent linking group represented by $L^1$ explained above in relation to the structural unit (a0).

As examples of the hydrocarbon group containing a ring in the structure thereof, a cyclic aliphatic hydrocarbon group, and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 30 carbon atoms. Further, the cyclic aliphatic hydrocarbon group may be either a polycyclic group or a monocyclic group, and is preferably a polycyclic group.

Specifically, the cyclic aliphatic hydrocarbon group can be selected appropriately from the multitude of groups that have been proposed for the resins of resist compositions designed for use with ArF excimer lasers. As the monocyclic aliphatic hydrocarbon group, a group in which two hydrogen atoms have been removed from a monocycloalkane of 3 to 20 carbon atoms is preferable. Examples of the monocycloalkane include cyclopentane and cyclohexane. As the polycyclic aliphatic hydrocarbon group, a group in which two hydrogen atoms have been removed from a polycycloalkane of 7 to 30 carbon atoms is preferable. Examples of the polycycloalkane include adamantane, norbornane, isobornane, tricyclodecane and tetracyclododecane.

The cyclic aliphatic hydrocarbon group may have part or all of the hydrogen atoms substituted with a substituent other than a polar group. Examples of the substituent include an alkyl group of 1 to 5 carbon atoms, a fluorine atom, a fluorinated alkyl group of 1 to 5 carbon atoms, and an oxygen atom (=O).

When the hydrocarbon group within the polar group-containing aliphatic hydrocarbon group is a linear or branched aliphatic hydrocarbon group, as the structural unit (a3), a structural unit derived from a hydroxyalkylester of acrylic acid is preferable. As the hydroxyalkyl group in the structural unit, a hydroxyalkyl group of 1 to 10 carbon atoms is preferable.

In addition, when the polar group-containing aliphatic hydrocarbon group is an aliphatic hydrocarbon group containing a ring in the structure thereof, as the structural unit (a3), a structural unit represented by general formula (a3-1) shown below, a structural unit represented by general formula (a3-2) shown below, and a structural unit represented by general formula (a3-3) shown below are preferable. Among these, a structural unit represented by the formula (a3-1) is preferable.

[Chemical Formula 55]

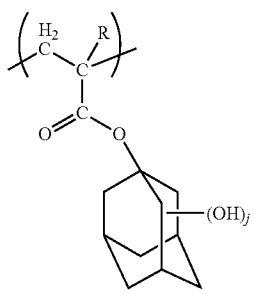

(a3-1)

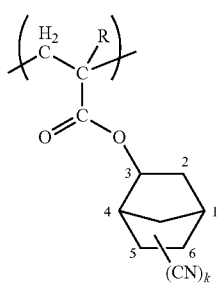

(a3-2)

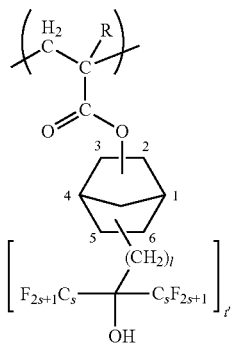

(a3-3)

In the formulas, R is the same as defined above; j represents an integer of 1 to 3; k represents an integer of 1 to 3; t' represents an integer of 1 to 3; 1 represents an integer of 1 to 5; and s represents an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group. j is preferably 1, and it is particularly desirable that the hydroxyl group be bonded to the 3rd position of the adamantyl group. In formula (a3-2), k is preferably 1. The cyano group is preferably bonded to the 5th or 6th position of the norbornyl group.

In formula (a3-3), t' is preferably 1. 1 is preferably 1. s is preferably 1. Further, in formula (a3-3), it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3), one type of structural unit may be used, or two or more types may be used in combination.

In the component (A 1), the amount of the structural unit (a3) based on the combined total of all structural units constituting the component (A1) is preferably 5 to 50 mol %, more preferably 5 to 40 mol %, and still more preferably 2 to 25 mol %.

The component (A1) may also have a structural unit other than the above-mentioned structural units (a1) to (a3), as long as the effects of the present invention are not impaired.

As such a structural unit, any other structural unit which cannot be classified as one of the above structural units (a1) to (a3) can be used without any particular limitation, and any of the multitude of conventional structural units used within resist resins for ArF excimer lasers or KrF excimer lasers (and particularly for ArF excimer lasers) can be used.

As such a structural unit, for example, a structural unit (a4) derived from an acrylate ester containing a non-acid-dissociable aliphatic polycyclic group can be mentioned.

An "acid non-dissociable, aliphatic polycyclic group" in the structural unit (a4) refers to an aliphatic polycyclic group which is not dissociated by the action of acid generated from the structural unit (a0) or component (B) upon exposure, and remains in the structural unit. By including the structural unit (a4) having the aliphatic polycyclic group, the shape of the resist pattern can be improved.

Specific examples of the acid non-dissociable aliphatic polycyclic group include monovalent aliphatic polycyclic groups in which the carbon atom having an atom adjacent to the aliphatic polycyclic group (e.g., —O— within —C(=O)—O—) bonded thereto has no substituent (a group or an atom other than hydrogen).

The aliphatic cyclic group is not particularly limited as long as it is acid non-dissociable, and any of the multitude of conventional polycyclic groups used within the resin component of resist compositions for ArF excimer lasers or KrF excimer lasers (and particularly for ArF excimer lasers) can be used. The aliphatic cyclic group may be either saturated or unsaturated, preferably saturated. Specific examples include groups in which one hydrogen atom has been removed from the cycloalkanes (such as monocycloalkanes and polycycloalkanes) described above in the explanation of the aliphatic cyclic group for the structural unit (a1).

The aliphatic cyclic group may be either a monocyclic group or a polycyclic group. In terms of the aforementioned effects, a polycyclic group is preferable. In particular, a bi-, tri- or tetracyclic group is preferable. In consideration of industrial availability and the like, at least one polycyclic group selected from amongst a tricyclodecyl group, an adamantyl group, a tetracyclododecyl group, an isobornyl group and a norbornyl group is particularly desirable.

Specific examples of the acid non-dissociable aliphatic cyclic group include monovalent aliphatic cyclic groups in which the carbon atom having an atom adjacent to the aliphatic cyclic group (e.g., —O— within —C(=O)—O—) bonded thereto has no substituent (a group or an atom other than hydrogen). More specific examples include groups represented by general formulas (1-1) to (1-9) explained above in relation to the structural unit (a1) in which the $R^{14}$ group has been substituted with a hydrogen atom; and a cycloalkane having a tertiary carbon atom constituting the ring skeleton and having one hydrogen atom removed from.

The aliphatic cyclic group may have a substituent. Examples of the substituent include an alkyl group of 1 to 5 carbon atoms, a fluorine atom and a fluorinated alkyl group of 1 to 5 carbon atoms.

As the structural unit (a4), a structural unit represented by general formula (a4-0) shown below is preferable, and a structural unit represented by any one of general formulas (a4-1) to (a4-5) shown below is particularly desirable.

[Chemical Formula 56]

(a4-0)

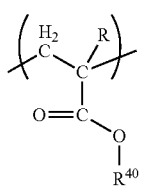

In the formulas, R is the same as defined above; and $R^{40}$ represents an acid non-dissociable aliphatic polycyclic group.

[Chemical Formula 57]

(a4-1)

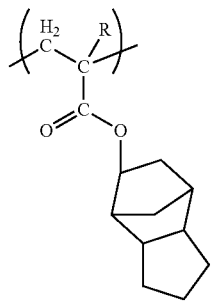

(a4-2)

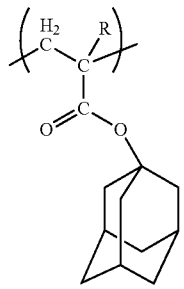

(a4-3)

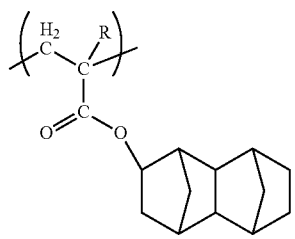

(a4-4)

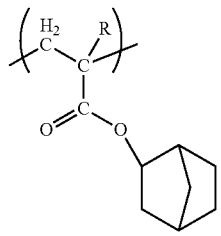

(a4-5)

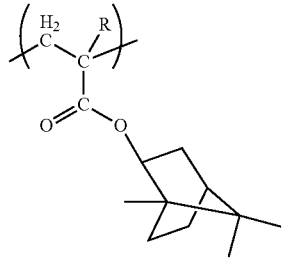

In the formulas, R is the same as defined above.

As the structural unit (a4), one type of structural unit may be used, or two or more types may be used in combination.

In the component (A1), the amount of the structural unit (a4) based on the combined total of all structural units constituting the component (A1) is preferably 1 to 30 mol %, and more preferably 10 to 20 mol %.

The component (A1) is preferably a copolymer containing the structural units (a0) and (a1). Specific examples of the component (A1) include a copolymer consisting of the structural units (a0) and (a1); a copolymer consisting of the structural units (a0), (a1) and (a2); a copolymer consisting of the structural units (a0), (a1) and (a3); a copolymer consisting of the structural units (a0), (a1), (a2) and (a3); and a copolymer consisting of the structural units (a0), (a1), (a2), (a3) and (a4). Among these, a copolymer consisting of the structural unit (a0), (a1), (a2) and (a3) is preferable.

As the component (A1), a copolymer represented by general formula (A1-1) shown below which includes four types of structural units is particularly desirable.

[Chemical Formula 58]

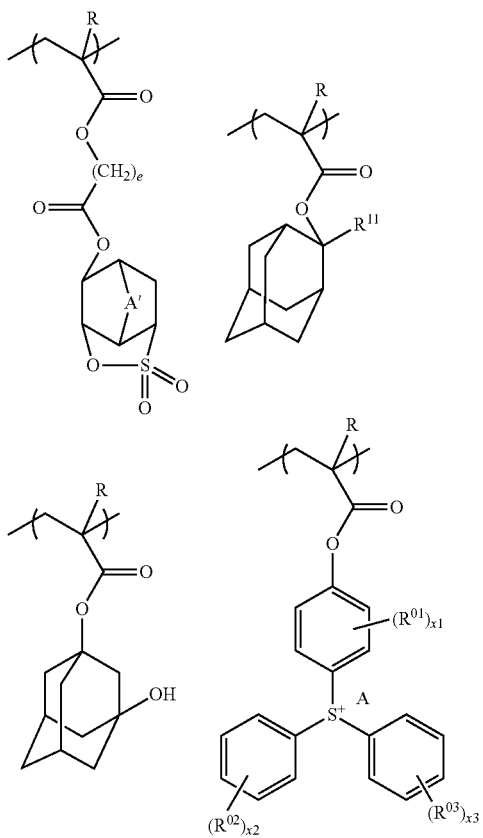

(A1-1)

In the formula, R, e, A", $R^{11}$, A, $R^{01}$ to $R^{03}$ and x1 to x3 are the same as defined above, wherein the plurality of R may be the same or different from each other.

The weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,000 to 20,000. When the weight average molecular weight of the polymer is no more than the upper limit of the above-mentioned range, the resist composition exhibits a satisfactory solubility in a resist solvent. On the other hand, when the weight average molecular weight is at least as large as the lower limit of the abovementioned range, dry etching resistance and the cross-sectional shape of the resist pattern becomes satisfactory.

Further, the dispersity (Mw/Mn) is not particularly limited, but is preferably 1.0 to 5.0, more preferably 1.0 to 3.0, and most preferably 1.2 to 2.5. Here, Mn is the number average molecular weight.

When the component (A) is a component (A2) (that is, a component which exhibits an alkali solubility, and contains a crosslinking reactive group), as the component (A), a component in which the structural unit (a0) has been included in an alkali resin which has been conventionally used as a base component for a negative resist composition, can be mentioned. Examples of the alkali soluble resin include the same resins as those in the explanation of the compound (C) described later.

As the alkali soluble resin, a resin containing a structural unit which contains a hydrophilic group such as a phenolic hydroxy group, an alcohol group, a fluorinated alcohol group, a carboxy group or a sulfoneamide group is preferable. Specific examples of the structural units include a structural unit derived from hydroxystyrene, a structural unit derived from a fluorinated alcohol (meth)acrylate, and a structural unit derived from a norbornenehexafluoroalcohol.

Here, a "structural unit derived from a hydroxystyrene" refers to a structural unit that is formed by the cleavage of the ethylenic double bond of a hydroxystyrene, a fluorinated alcohol (meth)acrylate or a norbornenehexafluoroalcohol.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

As the monomers for deriving the corresponding structural units, commercially available monomers may be used, or the monomers may be synthesized by a conventional method.

For example, as a monomer for deriving the structural unit (a0), a compound (I) represented by general formula (1) shown below (hereafter, referred to as compound (I)) can be used. The method of producing the compound (I) will be described later.

[Chemical Formula 59]

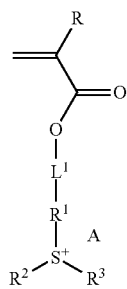

(I)

In the formula, R, $R^1$, $R^2$, $R^3$, $L^1$ and A are the same as defined above.

<Component (B)>

The resist composition of the present invention may also contain an acid-generator component (B) (hereafter, referred to as "component (B)") which generates acid upon exposure and which does not fall under the definition of the component (A).

As the component (B), there is no particular limitation, and any of the known acid generators used in conventional chemically amplified resist compositions can be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As an onium salt acid generator, a compound represented by general formula (b-1) or (b-2) shown below can be used.

[Chemical Formula 60]

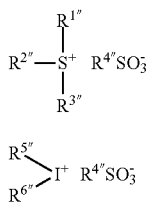

In the formulas above, $R^{1''}$ to $R^{3''}$, $R^{5''}$ and $R^{6''}$ each independently represent an aryl group or alkyl group which may have a substituent, wherein two of $R^{1''}$ to $R^3$ may be bonded to each other to form a ring with the sulfur atom; and $R^{4''}$ represents an alkyl group, a halogenated alkyl group, an aryl group or an alkenyl group which may have a substituent, and at least one of $R^{5''}$ and $R^{6''}$ represents an aryl group.

In formula (b-1), $R^{1''}$ to $R^{3''}$ each independently represents an aryl group which may have a substituent or an alkyl group which may have a substituent. In formula (b-1), two of $R^{1''}$ to $R^{3''}$ may be bonded to each other to form a ring with the sulfur atom.

Further, among $R^{1''}$ to $R^{3''}$, at least one group represents an aryl group. Among $R^{1''}$ to $R^3$, two or more groups are preferably aryl groups, and it is particularly desirable that all of $R^{1''}$ to $R^{3''}$ are aryl groups.

The aryl group of $R^{1''}$ to $R^{3''}$ is not particularly limited, and includes, for example, an aryl group of 6 to 20 carbon atoms. The aryl group is preferably an aryl group having 6 to 10 carbon atoms because it can be synthesized at a low cost. Specific examples thereof include a phenyl group and a naphthyl group.

The aryl group may have a substituent. The expression "has a substituent" means that part or all of the hydrogen atoms within the aryl group has been substituted with a substituent. Examples of the substituent include an alkyl group, an alkoxy group, a halogen atom, a hydroxyl group, an alkoxyalkyloxy group, —O—$R^{50}$—C(=O)—(O)$_n$—$R^{51}$ (in the formula, $R^{50}$ represents an alkylene group or a single bond, $R^{51}$ represents an acid dissociable group or an acid non-dissociable group, and n represents 0 or 1).

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

The halogen atom, with which hydrogen atoms of the aryl group may be substituted, is preferably a fluorine atom.

Examples of the alkoxyalkyloxy group which substitutes the hydrogen atoms) within the aryl group include —O—C($R^{47}$)($R^{48}$)—O—$R^{49}$ (in the formula, each of $R^{47}$ and $R^{48}$ independently represents a hydrogen atom or a linear or branched alkyl group, and $R^{49}$ represents an alkyl group, wherein $R^{48}$ and $R^{49}$ may be mutually bonded to form a ring structure, provided that at least one of $R^{47}$ and $R^{48}$ represents a hydrogen atom).

The alkyl group for $R^{47}$ and $R^{48}$ preferably has 1 to 5 carbon atoms. As the alkyl group, an ethyl group or a methyl group is preferable, and a methyl group is most preferable.

Further, it is preferable that at least one of $R^{47}$ and $R^{48}$ represent a hydrogen atom, and the other represent a hydrogen atom or a methyl group. It is particularly desirable that both of $R^{47}$ and $R^{48}$ represent a hydrogen atom.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, an ethyl group, a propyl group, an n-butyl group and a tert-butyl group.

The cyclic alkyl group for $R^{49}$ preferably has 4 to 15 carbon atoms, more preferably 4 to 12, and most preferably 5 to 10. Specific examples thereof include groups in which one or more hydrogen atoms have been removed from a monocycloalkane or a polycycloalkane such as a bicycloalkane, tricycloalkane or tetracycloalkane, and which may or may not be substituted with an alkyl group of 1 to 5 carbon atoms, a fluorine atom or a fluorinated alkyl group. Examples of the monocycloalkane include cyclopentane and cyclohexane. Examples of polycycloalkanes include adamantane, norbornane, isobornane, tricyclodecane and tetracyclododecane. Among these, a group in which one or more hydrogen atoms have been removed from adamantane is preferable.

$R^{48}$ and $R^{49}$ may be mutually bonded to form a ring structure. In such a case, a cyclic group is formed by $R^{48}$, $R^{49}$, the oxygen atom having $R^{49}$ bonded thereto, and the carbon atom having the oxygen atom and $R^{48}$ bonded thereto. Such a cyclic group is preferably a 4 to 7-membered ring, and more preferably a 4 to 6-membered ring.

In the —O—$R^{50}$—C(=O)—(O)$_n$—$R^{51}$ group which may substitute the hydrogen atoms within the aryl group, the alkylene group for $R^{50}$ is preferably a linear or branched alkylene group of 1 to 5 carbon atoms. Examples of the alkylene group include a methylene group, an ethylene group, a trimethylene group, a tetramethylene group and a 1,1-dimethylethylene group.

The acid dissociable group for $R^{51}$ is not particularly limited as long as it is an organic group that is dissociable by the action of an acid (generated from the component (B) upon exposure), and examples thereof include the same acid dissociable, dissolution inhibiting groups as those described above in the explanation of the component (A). Among these, a tertiary alkyl ester-type acid dissociable group is preferable.

Preferable examples of the acid non-dissociable group for $R^{51}$ include a decyl group, a tricyclodecyl group, an adamantyl group, a 1-(1-adamantyl)methyl group, a tetracyclododecyl group, an isobornyl group and a norbornyl group.

The alkyl group for $R^{1''}$ to $R^{3''}$ may be linear, branched, cyclic, or a combination thereof. The number of carbon atoms thereof is preferably 1 to 30.

When the alkyl group is linear or branched, the number of carbon atoms thereof is preferably 1 to 20, more preferably 1 to 17, still more preferably 1 to 15, and most preferably 1 to 10. In particular, an alkyl group of 1 to 6 carbon atoms is preferable, and specific examples thereof include a methyl group, an ethyl group, a propyl group, an isopropyl group, an n-butyl group, an isobutyl group, a tert-butyl group, a pentyl group, an isopentyl group, a neopentyl group and a hexyl group. Among these examples, a methyl group or an ethyl group is preferable, and a methyl group is particularly desirable.

When the alkyl group is cyclic (i.e., a cycloalkyl group), the number of carbon atoms is preferably 3 to 30, more preferably 3 to 20, still more preferably 3 to 15, still more preferably 4 to 12, and most preferably 5 to 10. The alkyl group may be monocyclic or polycyclic. Examples thereof include groups in which one or more of the hydrogen atoms have been removed from a monocycloalkane; and groups in which one or more of the hydrogen atoms have been removed from a polycycloalkane such as a bicycloalkane, a tricycloalkane, or a tetracycloalkane. Specific examples of the monocycloalkane include cyclopentane and cyclohexane. Specific examples of the polycycloalkane include adamantane, norbornane, isobornane, tricyclodecane and tetracyclododecane.

The alkyl group may have a substituent. The expression "has a substituent" means that part or all of the hydrogen atoms within the alkyl group has been substituted with a substituent. Examples of the substituent include an aryl group, an oxygen atom (=O), an alkoxy group, a halogen atom, a hydroxyl group, an alkoxyalkyloxy group, —O—$R^{50}$—C(=O)—(O)$_n$—$R^{51}$ (in the formula, $R^{50}$ represents an alkylene group or a single bond, $R^{51}$ represents an acid dissociable group or an acid non-dissociable group, and n represents 0 or 1). As examples of the aryl group, the same aryl groups as those described above for $R^{1\prime\prime\prime}$ to $R^{3\prime\prime\prime}$ can be used. Further, as the alkoxy group, halogen atom, alkoxyalkyloxy group and —O—$R^{50}$—C(=O)—(O)$_n$—$R^{51}$, the same groups which the aforementioned aryl group may have as a substituent can be mentioned.

In formula (b-1), two of $R^{1\prime\prime\prime}$ to $R^{3\prime\prime\prime}$ may be mutually bonded to form a ring with the sulfur atom. The ring may be saturated or unsaturated. Further, the ring may be monocyclic or polycyclic. For example, when either one or both of the two of $R^{1\prime\prime\prime}$ to $R^{3\prime\prime\prime}$ represent a cyclic group (a cyclic alkyl group or an aryl group), a polycyclic ring (condensed ring) is formed when the two groups are bonded.

When two of $R^{1\prime\prime\prime}$ to $R^{3\prime\prime\prime}$ are mutually bonded to form a ring, the ring containing the sulfur atom in the skeleton thereof is preferably a 3 to 10-membered ring, and most preferably a 5 to 7-membered ring.

Specific examples of the ring formed by two of $R^{1\prime\prime\prime}$ to $R^{3\prime\prime\prime}$ mutually bonded include benzothiophene, dibenzothiophene, 9H-thioxanthene, thioxanthene, thianthrene, phenoxathiine, tetrahydrothiophenium and tetrahydrothiopyranium.

When two of $R^{1\prime\prime\prime}$ to $R^{3\prime\prime\prime}$ are bonded to each other to form a ring with the sulfur atom, the remaining one of $R^{1\prime\prime\prime}$ to $R^{3\prime\prime\prime}$ is preferably an aryl group.

In the compound represented by formula (b-1), preferable examples of the cation moiety in which all of $R^{1\prime\prime\prime}$ to $R^{3\prime\prime\prime}$ represents a phenyl group which may have a substituent, i.e., the cation moiety having a triphenylsulfonium skeleton, include cation moieties represented by formulas (I-1-1) to (I-1-14) shown below.

Further, a cation moiety in which part or all of the phenyl groups have been replaced with a naphthyl group which may have a substituent can also be given as a preferable example. It is preferable that 1 or 2 of the 3 phenyl groups are replaced with a naphthyl group.

[Chemical Formula 61]

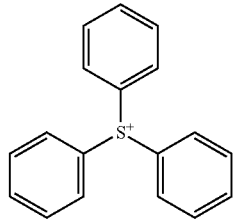

(I-1-1)

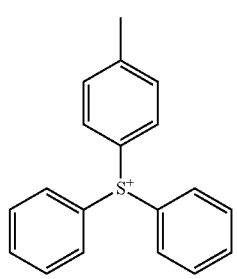

(I-1-2)

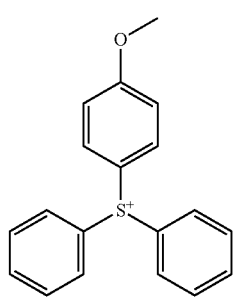

(I-1-3)

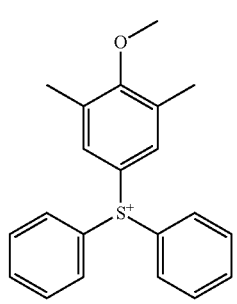

(I-1-4)

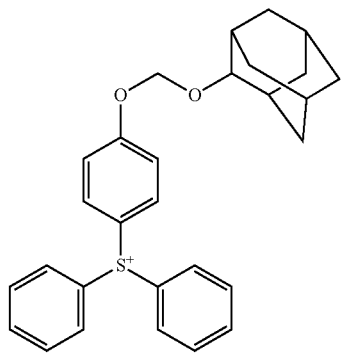

(I-1-5)

(I-1-6)
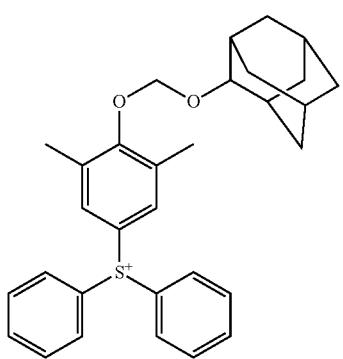
(I-1-7)
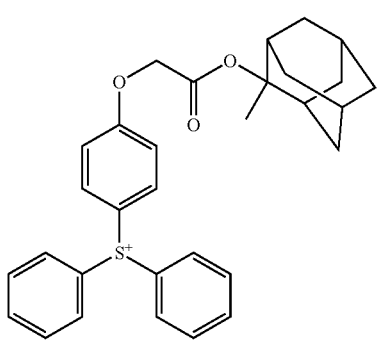
[Chemical Formula 62]
(I-1-8)
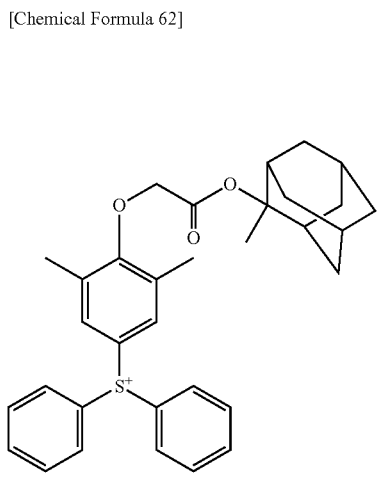
(I-1-9)
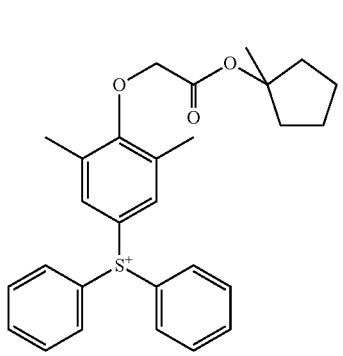
(I-1-10)
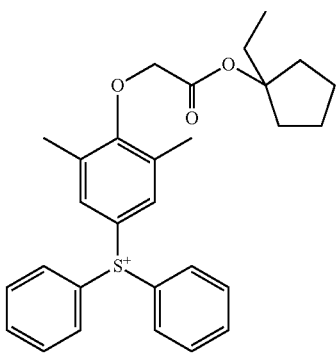
(I-1-11)
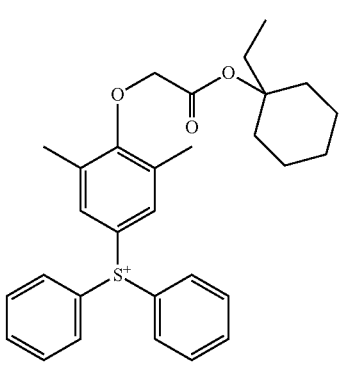
(I-1-12)
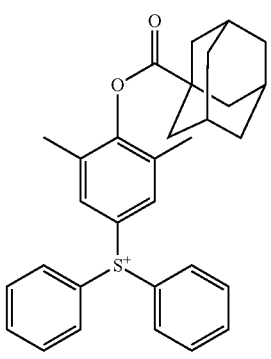
(I-1-13)
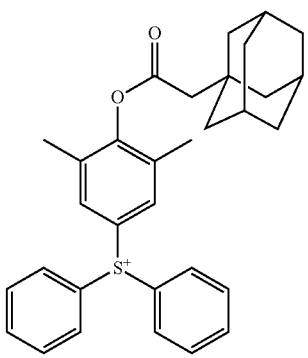

(I-1-14)

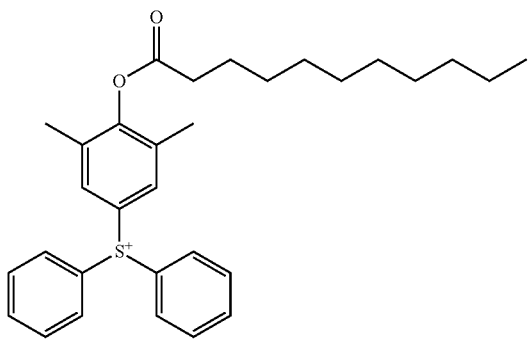

Furthermore, in the compound represented by formula (b-1), preferable examples of the cation moiety in which two of $R^{1\prime\prime\prime}$ to $R^{3\prime\prime\prime}$ are mutually bonded to form a ring with the sulfur atom include cation moieties represented by formulas (I-2-1) to (I-2-4) shown below.

[Chemical Formula 63]

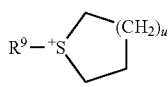 (I-2-1)

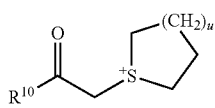 (I-2-2)

In the formulas, $R^9$ represents an aryl group which may have a substituent or an alkyl group which may have a substituent; $R^{10}$ represents an aryl group which may have a substituent, an alkyl group which may have a substituent, an alkoxy group which may have a substituent or a hydroxy group; and u represents an integer of 1 to 3.

[Chemical Formula 64]

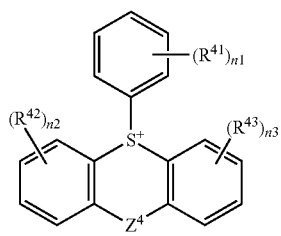 (I-2-3)

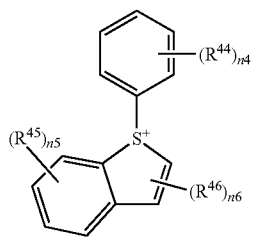 (I-2-4)

In the formulas, $Z^4$ represents a single bond, a methylene group, a sulfur atom, an oxygen atom, a nitrogen atom, a carbonyl group, —SO—, —SO$_2$—, —SO$_3$—, —COO—, —CONH— or —N(R$_N$)— (R$_N$ represents an alkyl group of 1 to 5 carbon atoms); each of $R^{41}$ to $R^{46}$ independently represents an alkyl group, an acetyl group, an alkoxy group, a carboxy group, a hydroxy group pr a hydroxyalkyl group; each of $n_1$ to $n_5$ independently represents an integer of 0 to 3; and $n_6$ represents an integer of 0 to 2.

In the formulas (I-2-1) and (I-2-2), as the aryl group for $R^9$ and $R^{10}$, the same the aryl groups as those described for $R^{1\prime\prime\prime}$ to $R^{3\prime\prime\prime}$ can be mentioned, and a phenyl group or a naphthyl group is preferable, and a naphthyl group is particularly desirable. Examples of substituents which the aryl group may have include the same substituents as those described above for substituting part or all of the hydrogen atoms within the aryl group for $R^{1\prime\prime\prime}$ to $R^{3\prime\prime\prime}$.

As the alkyl group for $R^9$ and $R^{10}$, the same alkyl groups as those described above for $R^{1\prime\prime\prime}$ to $R^{3\prime\prime\prime}$ can be used, and an alkyl group of 1 to 6 carbon atoms is preferable, and a methyl group is particularly desirable. Examples of substituents which the alkyl group may have include the same substituents as those described above for substituting part or all of the hydrogen atoms within the alkyl group for $R^{1\prime\prime\prime}$ to $R^{3\prime\prime\prime}$.

As examples of the alkoxy group for $R^9$ to $R^{10}$, groups in which the aforementioned alkyl groups for $R^9$ to $R^{10}$ have been bonded to an oxygen atom (—O—) can be given.

u is an integer of 1 to 3, and most preferably 1 or 2.

In general formulas (I-2-3) and (I-2-4), $Z^4$ is preferably a single bond.

With respect to $R^{44}$ to $R^{46}$, the alkyl group is preferably an alkyl group of 1 to 5 carbon atoms, more preferably a linear or branched alkyl group, and most preferably a methyl group, an ethyl group, a propyl group, an isopropyl group, an n-butyl group or a tert-butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably a group in which one or more hydrogen atoms in the aforementioned alkyl group have been substituted with hydroxy groups, and examples thereof include a hydroxymethyl group, a hydroxyethyl group and a hydroxypropyl group.

If there are two or more of an individual $R^{41}$ to $R^{46}$ group, as indicated by the corresponding value of $n_1$ to $n_6$, then the two or more of the individual $R^{41}$ to $R^{46}$ group may be the same or different from each other.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

In formulas (b-1) and (b-2), $R^{4\prime\prime\prime}$ represents an alkyl group, a halogenated alkyl group, an aryl group or an alkenyl group which may have a substituent.

The alkyl group for $R^{4\prime\prime\prime}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms.

As an example of the halogenated alkyl group for $R^{4\prime\prime\prime}$, a group in which part of or all of the hydrogen atoms of the aforementioned linear, branched or cyclic alkyl group have been substituted with halogen atoms can be given. Examples of the aforementioned halogen atom include a fluorine atom, a chlorine atom, a bromine atom and an iodine atom, and a fluorine atom is preferable.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratio is preferable because the acid strength increases.

The aryl group for $R^{4''}$ is preferably an aryl group of 6 to 20 carbon atoms.

The alkenyl group for $R^{4''}$ is preferably an alkenyl group of 2 to 10 carbon atoms.

With respect to $R^{4''}$, the expression "may have a substituent" means that part of or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4''}$ may have one substituent, or two or more substituents.

Examples of the substituent include a halogen atom, a hetero atom, an alkyl group, and a group represented by the formula $R^{5'}-L^{2'}-$ (in the formula, $R^{5'}$ represents a hydrocarbon group of 3 to 30 carbon atoms which may have a substituent; and $L^{2'}$ represents a single bond or a divalent linking group).

Examples of halogen atoms and alkyl groups include the same halogen atoms and alkyl groups as those described above with respect to the halogenated alkyl group for $R^{4''}$.

Examples of hetero atoms include an oxygen atom, a nitrogen atom, and a sulfur atom.

In the group represented by the formula $R^{5'}-L^{2'}$, the group for $-R^{5'}$ is the same as defined for $R^5$ in the general formula (1). As examples of $L^{2'}$, the same groups as those described above for $L^2$ in the general formula (1) can be given.

In the present invention, $R^{4''}$ preferably has a group represented by formula: $R^{5'}-L^{2'}-$ as a substituent. In this case, $R^{4''}$ is preferably a group represented by formula $R^{5'}-L^{2'}-R^{4'}-$ [wherein $R^{5'}$, and $L^{2'}$ are the same as defined above; and $R^{4'}$ represents an alkylene group of 1 to 4 carbon atoms which may have a substituent, or a fluorinated alkylene group of 1 to 4 carbon atoms which may have a substituent].

In the group represented by the formula $R^{5'}-L^{2'}-R^{4'}-$, the alkylene group for $R^{4'}$ is the same as defined for $R^4$ in the general formula (1).

In formula (b-2), $R^{5'''}$ and $R^{6'''}$ each independently represent an aryl group or alkyl group. At least one of $R^{5'''}$ and $R^{6'''}$ represents an aryl group. It is preferable that both of $R^{5'''}$ and $R^{6'''}$ represent an aryl group.

As the aryl group for $R^{5'''}$ and $R^{6'''}$, the same aryl groups as those described above for $R^{1'''}$ to $R^{3'''}$ can be used.

As the alkyl group for $R^{5'''}$ to $R^{6'''}$, the same alkyl groups as those described above for $R^{1'''}$ to $R^{3'''}$ can be used.

It is particularly desirable that both of $R^{5'''}$ and $R^{6'''}$ represents a phenyl group.

As $R^{4''}$ in formula (b-2), the same groups as those mentioned above for $R^{4''}$ in the formula (b-1) can be used.

For example, when $R^{4''}$ is an unsubstituted fluorinated alkyl group of 1 to 4 carbon atoms, that is, when the anion part ($R^{4''}-SO_3^-$) is a fluoroalkyl sulfonate, specific examples of suitable onium salt acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonae; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts are replaced by an anion moiety in which $R^{4''}$ represents an unsubstituted alkyl group, that is, replaced by an unsubstituted alkylsulfonate. As the alkylsulfonate, methanesulfonate, n-propanesulfonate, n-butanesulfonate, n-octanesulfonate, 1-adamantanesulfonate, or 2-norbornanesulfonate, d-camphor-10-sulfonate, benzenesulfonate, perfluorobenzenesulfonate and p-toluenesulfonate can be mentioned.

Furthermore, onium salts in which the anion moiety of these onium salts is replaced by an anion moiety in which $R^{4''}$ is a group represented by $R^{5'}-L^{2'}-R^{4'}-$, that is, an anion moiety represented by formula (1') shown below (hereafter, referred to as anion (1')) can be used.

[Chemical Formula 65]

$$R^{5'}-L^{2'}-R^{4'}-SO_3^- \qquad (1')$$

In the formula, $R^{4'}$ represents an alkylene group of 1 to 4 carbon atoms which may have a substituent or a fluorinated alkylene group of 1 to 4 carbon atoms which may have a substituent; $L^{2'}$ represents a single bond or a divalent linking group; and $R^{5'}$ represents a hydrocarbon group of 3 to 30 carbon atoms which may have a substituent.

In general formula (1'), as $R^{4'}$, $L^{2'}$ and $R^{5'}$, the same groups as those described above for $R^4$, $L^2$ and $R^5$ in the general formula (1) can be mentioned, respectively.

Specific examples of the anion (1') include the same anions as those described as specific examples of the anion (1) in the explanation of the structural unit (a0).

As examples of the onium salt acid generators other than those represented by formula (b-1) or (b-2), onium salt acid generators containing an anion represented by formula (2') shown below can be given.

[Chemical Formula 66]

$$R^{7'}\text{-}L^{3'}\text{-}Y^{10'}\text{---}N^{-}\text{---}SO_2\text{---}R^{6'} \quad (2')$$

In the formula, $R^{6'}$ represents an alky group which may have a substituent or a fluorinated alkyl group which may have a substituent; $L^{3'}$ represents a single bond or a divalent linking group; $Y^{10'}$ represents a —$SO_2$— or a —CO—; and $R^{7'}$ represents a hydrocarbon group which may have a substituent.

In general formula (2'), as $R^{6'}$, $L^{3'}$ and $R^{7'}$, the same groups as those described above for $R^6$, $L^3$ and R' in the general formula (1) can be mentioned, respectively.

Specific examples of the anion (2') include the same anions as those described as specific examples of the anion (2) in the explanation of the structural unit (a0).

Specific examples of the onium salt acid generator containing an anion (2') include an onium salt acid generator in which an anion moiety ($R^{4''}SO_3^-$) in the general formula (b-1) or (b-2) has been substituted with an anion (2').

Further, onium salt-based acid generators in which the anion moiety ($R^{4''}SO_3^-$) in general formula (b-1) or (b-2) is replaced by an anion moiety represented by general formula (b-3) or (b-4) shown below (the cation moiety is the same as (b-1) or (b-2)), provided that, the anion (2') is excluded, may be used.

[Chemical Formula 67]

In the formulas, X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and more preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved. The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

As examples of the onium salt acid generators other than those represented by formula (b-1) or (b-2), onium salt acid generators containing an anion represented by formula: $R^{75}$—$COO^-$ [in the formula, $R^{75}$ represents an alkyl group which may have a substituent, a halogenated alkyl group which may have a substituent, an aryl group which may have a substituent or an alkenyl group which may have a substituent] can be given.

As $R^{75}$, the same groups as those described above for $R^{4''}$ can be used.

Specific examples of the group represented by the formula "$R^{75}$—$COO^-$" include a trifluoroacetate ion, an acetate ion, and a 1-adamantanecarboxylic acid ion.

Specific examples of the onium salt acid generator containing $R^{75}$—$COO^-$ include an onium salt acid generator in which an anion moiety ($R^{4''}SO_3^-$) in the general formula (b-1) or (b-2) has been substituted with $R^{75}$—$COO^-$.

In the present description, an oximesulfonate-based acid generator is a compound having at least one group represented by general formula (B-1) shown below, and has a feature of generating acid by irradiation. Such oximesulfonate acid generators are widely used for a chemically amplified resist composition, and can be appropriately selected.

[Chemical Formula 68]

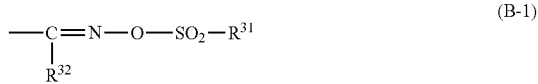

$$\begin{array}{c} \text{---C}\!=\!\text{N}\!-\!\text{O}\!-\!\text{SO}_2\!-\!\text{R}^{31} \\ | \\ \text{R}^{32} \end{array} \quad (B\text{-}1)$$

In the formula, each of $R^{31}$ and $R^{32}$ independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, particularly preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. As the alkyl group or aryl group for $R^{32}$, the same alkyl groups or aryl groups as those described above for $R^{31}$ can be used.

As $R^{32}$, a cyano group, an alkyl group of 1 to 8 carbon atoms having no substituent or a fluorinated alkyl group of 1 to 8 carbon atoms is particularly desirable.

Preferable examples of the oxime sulfonate-based acid generator include compounds represented by general formula (B-2) or (B-3) shown below.

[Chemical Formula 69]

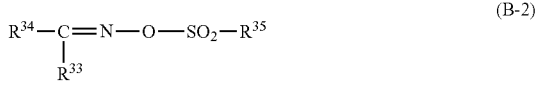

(B-2)

In the formula, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 70]

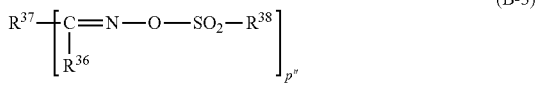

(B-3)

In the formula (B-3), $R^{36}$ represents a cyano group, an alkyl group having no substituent or a halogenated alkyl group; $R^{37}$ represents a divalent or trivalent aromatic hydrocarbon group; and $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclopentylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, (isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Furthermore, as preferable examples, the following can be used.

[Chemical Formula 71]

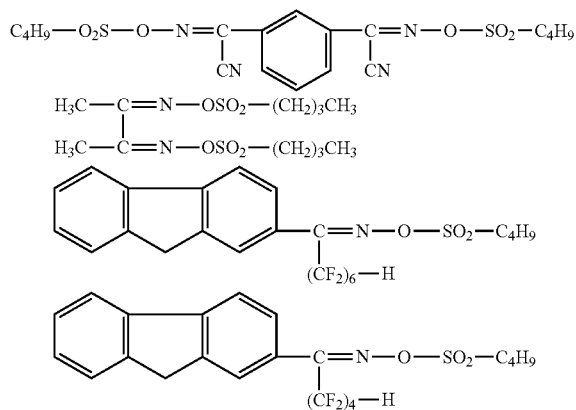

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be mentioned.

As the component (B), an onium salt acid generator having the anion (1') or (2') is preferable. By including the onium salt acid generator as a component (B), lithography properties such as resolution and LER can be improved.

The structure of anion (that is, anion represented by the formula (1') or (2')) within the onium salt acid generator may or may not be the same structure of anion (that is, anion (1) or (2)) within the structural unit (a0).

As the component (B), one type of acid generator may be used, or two or more types of acid generators may be used in combination.

When the resist composition contains the component (B), the amount of the component (B) relative to 100 parts by weight of the component (A) is preferably 1 to 70 parts by weight, and more preferably 5 to 50 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Other Optional Components>

The resist composition of the present invention may contain a base component which exhibits changed solubility in an alkali developing solution under action of acid other than the component (A) (hereafter, referred to as "component (C)"), as long as the effects of the present invention are not impaired.

As described above, the term "base component" refers to an organic compound capable of forming a film.

As the component (C), there is no particular limitation, and any of the known base components used in conventional chemically amplified resist compositions can be selected depending on whether a positive resist composition or a negative resist composition will be produced. The component (A) may be a resin, a low molecular weight compound, or a combination of these materials. As the component (C), one type of compound may be used, or two or more types may be used in combination.

When the resist composition of the present invention is a positive resist composition, as the component (C), a base component that exhibits increased solubility in an alkali developing solution under the action of acid is used. The base component is substantially insoluble in an alkali developing solution prior to exposure, but when acid is generated from the component (A) or (B) upon exposure, the action of this acid causes an increase in the solubility of the base component in an alkali developing solution. Therefore, in the formation of a resist pattern, by conducting selective exposure of a resist film formed by applying the positive resist composition onto a substrate, the exposed portions changes from an insoluble state to a soluble state in an alkali developing solution, whereas the unexposed portions remain insoluble in an alkali developing solution, and hence, a resist pattern can be formed by alkali developing.

As the base component, any of the multitude of conventional base components used within chemically amplified resist compositions (e.g., base resins used within chemically amplified resist compositions for ArF excimer lasers or KrF excimer lasers, preferably ArF excimer lasers) can be used. For example, as a base resin for ArF excimer laser, a base resin having the aforementioned structural unit (a1) as an essential component, and optionally the aforementioned structural units (a2) to (a4) can be used.

When the resist composition of the present invention is a negative resist composition, for example, as the component (C), a base component that is soluble in an alkali developing solution is used, and a cross-linking agent is blended in the negative resist composition. In the negative resist composition, when acid is generated from the component (A) or (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (C) for a negative resist composition, a resin that is soluble in an alkali developing solution (hereafter, referred to as "alkali-soluble resin") is used. Examples of the alkali soluble resin include a resin having a structural unit derived from at least one of α-(hydroxyalkyl) acrylic acid and an alkyl ester of α-(hydroxyalkyl)acrylic acid (preferably an alkyl ester having 1 to 5 carbon atoms), as disclosed in Japanese Unexamined Patent Application, First Publication No. 2000-206694; a (meth)acrylic resin or polycycloolefin resin having a sulfoneamide group, as disclosed in U.S. Pat. No. 6,949,325; a resin having a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycyclolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent blended with the base component that is soluble in an alkali developing solution, typically, an amino-based cross-linking agent such as a glycoluril having a methylol group or alkoxymethyl group, or a melamine-based cross-linking agent is preferable, as it enables formation of a resist pattern with minimal swelling.

The amount of the cross-linking agent added is preferably within the range from 1 to 50 parts by weight, relative to 100 parts by weight of the base component.

The resist composition of the present invention may further contain a nitrogen-containing organic compound (D) (hereafter referred to as the component (D)) which does not fall under the definition of the aforementioned components (A) to (C).

As the component (D), there is no particular limitation as long as it functions as an acid diffusion control agent, i.e., a quencher which traps the acid generated from the component (A) and the component (B) upon exposure. A multitude of these components (D) have already been proposed, and any of these known compounds may be used. Examples thereof include an aliphatic amine and an aromatic amine. Among these, an aliphatic amine is preferable, and a secondary aliphatic amine or tertiary aliphatic amine is particularly desirable.

An aliphatic amine is an amine having one or more aliphatic groups, and the aliphatic groups preferably have 1 to 20 carbon atoms.

Examples of these aliphatic amines include amines in which at least one hydrogen atom of ammonia ($NH_3$) has been substituted with an alkyl group or hydroxyalkyl group of 1 to 20 carbon atoms (i.e., alkylamines or alkylalcoholamines), and cyclic amines.

The alkyl group within the alkyl group and hydroxyalkyl group may be any of linear, branched or cyclic.

When the alkyl group is linear or branched, the number of carbon atoms thereof is preferably 2 to 20, and more preferably 2 to 8.

When the alkyl group is cyclic (i.e., a cycloalkyl group), the number of carbon atoms is preferably 3 to 30, more preferably 3 to 20, still more preferably 3 to 15, still more preferably 4 to 12, and most preferably 5 to 10. The alkyl group may be monocyclic or polycyclic. Examples thereof include groups in which one or more of the hydrogen atoms have been removed from a monocycloalkane; and groups in which one or more of the hydrogen atoms have been removed from a polycycloalkane such as a bicycloalkane, a tricycloalkane, or a tetracycloalkane. Specific examples of the monocycloalkane include cyclopentane and cyclohexane. Specific examples of the polycycloalkane include adamantane, norbornane, isobornane, tricyclodecane and tetracyclododecane.

Specific examples of the alkylamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine.

Specific examples of the alkylalcoholamines include diethanolamine, triethanolamine, diisopropanolamine, triisopropanolamine, di-n-octanolamine, tri-n-octanolamine, stearyldiethanolamine and lauryldiethanolamine.

The alkylamines and alkylalcoholamines may have a substituent other than alkyl groups or hydroxyalkyl groups, as a substituent with which a hydrogen atom of ammonia $NH_3$ is substituted. As an example of a substituent, an acyl group and a hydroxy group can be given. As the acyl group, a group represented by —C(=O)—$R^{111}$ [in the formula, $R^{111}$ represents an alkyl group of 1 to 12 carbon atoms] is particularly preferable. As $R^{111}$, a methyl group is particularly desirable.

In addition, the alkyl group or hydroxyalkyl group within the aforementioned alkylamine and alkylalcoholamine may have a substituent other than a hydroxy group. As an example of a substituent, an oxygen atom (=O) can be given.

Examples of alkylamines or alkylalcoholamines having such a substituent include an amine represented by formula: $R^{111}$—C(=O)—NH—$R^{112}$ can be mentioned. In the formula, $R^{111}$ is the same as defined above, $R^{112}$ represents an alkyl group which may have a substituent, a hydroxyalkyl group which may have a substituent and a hydroxy group. As the alkyl group and hydroxyalkyl group for $R^{112}$, the same alkyl group and hydroxyalkyl group as those defined above can be mentioned, and a cyclic alkyl group is preferable. As the substituent which the alkylene group or hydroxy alkylene group may have, an oxygen atom (=O) is preferable.

Specific examples of amines represented by formula $R^{111}$—C(=O)—NH—$R^{112}$ include acetamidocyclohexane, acetamidoadamantane, N-methylacetamide, N-ethylacetamide, 4-acetamidecyclohexanone, N-cyclohexylformamide, acetohydroxamic acid, N-acetylethanolamine, acetamidomethanol, N-acetylethanolamine, 4-acetamidocyclohexanol and the like.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine) can be used.

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris {2-(1-methoxyethoxy)ethyl}amine, tris{2-(1-ethoxyethoxy)ethyl}amine, tris {2-(1-ethoxypropoxy)ethyl}amine and tris[2-{2-(2-hydroxyethoxy)ethoxy}ethyl]amine.

Examples of aromatic amines include aniline, pyridine, 4-dimethylaminopyridine, pyrrole, indole, pyrazole, imidazole and derivatives thereof, as well as diphenylamine, triphenylamine and tribenzylamine.

These compounds can be used either alone, or in combinations of two or more different compounds.

The component (D) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

Furthermore, in the resist composition of the present invention, in order to prevent any deterioration in sensitivity, and improve the resist pattern shape and the post exposure stability of the latent image formed by the pattern-wise exposure of the resist layer, at least one compound (E) (hereafter referred to as "component (E)") selected from the group consisting of organic carboxylic acids and phosphorus oxo acids and derivatives thereof may also be added as an optional component.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of phosphorous oxo acid derivatives include esters in which a hydrogen atom within the above-mentioned phosphorous oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

As the component (E), one type may be used alone, or two or more types may be used in combination.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

The resist composition according to the present invention can be prepared by dissolving the materials for the resist composition in an organic solvent (hereafter, frequently referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone;

ketones such as acetone, methyl ethyl ketone, cyclohexanone, methyl-n-pentyl ketone, methyl isopentyl ketone, and 2-heptanone;

polyhydric alcohols, such as ethylene glycol, diethylene glycol, propylene glycol and dipropylene glycol;

compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable);

cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate;

and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2. For example, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3. Alternatively, when PGME and cyclohexanone is mixed as the polar solvent, the PGMEA:(PGME+cyclohexanone) weight ratio is preferably from 1:9 to 9:1, more preferably from 2:8 to 8:2, and still more preferably 3:7 to 7:3.

Further, as the component (S), a mixed solvent of PGMEA, EL, or PGMEA with a polar solvent and a mixed solvent of PGMEA, EL, or PGMEA with γ-butyrolactone are also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate, depending on the thickness of the coating film. In general, the organic solvent is used in an amount such that the solid content of the resist composition becomes within the range of 1 to 20% by weight, and preferably 2 to 15% by weight.

The resist composition of the present invention described above and the component (A) blended in the resist composition are novel, and are conventionally unknown in the art.

When the component (A) is subjected to exposure, acid (anion (1) or (2)) is generated from the structural unit (a0). Therefore, the component (A) can be used as an acid generator for a chemically amplified resist composition. In addition, the component (A) is a resin, and functions as a base component for a resist composition, and hence, the component (A) can form a film (resist film) alone.

In particular, when the component (A) has an acid dissociable, dissolution inhibiting group (for example, when the component (A) contains a structural unit (a1)), the component (A) can constitute a chemically amplified resist composition alone. That is, when the component (A) is subjected to exposure, acid generated from the structural unit (a0) dissociates the acid dissociable, dissolution inhibiting group in the component (A), thereby increasing the solubility of the entire the component (A) in an alkali developing solution. Therefore, even if the film consists of only the component (A), a resist pattern can be formed by conducting selective exposure and alkali development. Therefore, the component (A) is useful as a base component for a positive resist composition.

Further, according to the resist composition of the present invention, lithography properties such as resolution and exposure dose margin (EL) are excellent, and the shape of the formed resist pattern is excellent with reduced line width roughness (LWR). EL is the range of the exposure dose in which a resist pattern can be formed with a size within a predetermined range of variation from a target size, when exposure is conducted by changing the exposure dose, i.e., the range of the exposure dose in which a resist pattern faithful to the mask pattern can be formed. The larger the exposure margin, the smaller the variation in the pattern size depending on the change in the exposure dose, thereby resulting in favorable improvement in the process margin.

The reason why the lithography properties can be improved has not been elucidated yet, but is presumed that because a resin contains the structural unit (a0), the part generating acid can be uniformly distributed in the resist film, and furthermore, because the acid composed of an anion (1) or (2) generated from the structural unit (a0) has a bulky structure as compared to the perfluorialkylsulfonate having 4 or less carbon atoms which is conventionally used as an acid-generator, the diffusion length of acid in the resist film can be shorten when conducting exposure to the resist film formed by using the resist composition.

The aforementioned effect is particularly achieved in the case where the onium salt acid generator having the anion (1') or (2') is used as a component (B). It is presumed that because the anions (1') and (2') has a bulky structure as well as the anions (1) and (2), the diffusion length of the acid composed of these anions in the resist film when conducting exposure to the resist film formed by using the resist composition can be shorten.

<<Method of Forming a Resist Pattern>>

The method of forming a resist pattern according to the present invention includes: forming a resist film on a substrate using a resist composition of the present invention; conducting exposure of the resist film; and developing the resist film to form a resist pattern.

The method for forming a resist pattern according to the present invention can be performed, for example, as follows.

Firstly, a resist composition according to the present invention is applied onto a substrate using a spinner or the like, and a prebake (post applied bake (PAB)) is conducted at a temperature of 80 to 150° C. for 40 to 120 seconds, preferably 60 to 90 seconds, to form a resist film. Following selective exposure of the thus formed resist film, either by exposure through a mask pattern using an exposure apparatus such as an ArF exposure apparatus, an electron beam lithography apparatus or an EUV exposure apparatus, or by patterning via direct irradiation with an electron beam without using a mask pattern, PEB (post exposure baking) is conducted under temperature conditions of 80 to 150° C. for 40 to 120 seconds, and preferably 60 to 90 seconds. Subsequently, developing is conducted using an alkali developing solution such as a 0.1 to 10% by weight aqueous solution of tetramethylammonium hydroxide (TMAH), preferably followed by rinsing with pure water, and drying. If desired, bake treatment (post bake) can be conducted following the developing. In this manner, a resist pattern that is faithful to the mask pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) can be used.

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The positive resist composition of the present invention is effective to KrF excimer laser, ArF excimer laser, EB and EUV, and particularly effective to ArF excimer laser.

The exposure of the resist film can be either a general exposure (dry exposure) conducted in air or an inert gas such as nitrogen, or immersion exposure (liquid immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ and $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

compounds and perfluoroalkylamine compounds. Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

<<Polymeric Compound>>

The polymeric compound of the present invention is a polymeric compound including a structural unit (a0) represented by general formula (a0) shown below.

The explanation of the polymeric compound of the present invention is the same as the explanation of the component (A) of the resist composition according to the present invention described above.

[Chemical Formula 72]

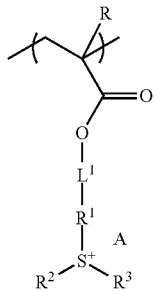

(a0)

In the formula, R represents a hydrogen atom, an alkyl group of 1 to 5 carbon atoms or a halogenated alkyl group of 1 to 5 carbon atoms; $R^1$ represents a divalent aromatic cyclic group; each of $R^2$ and $R^3$ independently represents an aryl group which may have a substituent, an alkyl group which may have a substituent or an alkenyl group which may have a substituent, wherein $R^2$ and $R^3$ may be mutually bonded to form a ring with the sulfur atom; $L^1$ represents a single bond or a divalent linking group; and A represents an anion represented by general formula (1) or (2) shown below.

[Chemical Formula 73]

$$R^5\text{-}L^2\text{-}R^4\text{—}SO_3^- \qquad (1)$$

$$R^7\text{-}L^3\text{-}Y^{10}\text{—}N^-\text{—}SO_2\text{—}R^6 \qquad (2)$$

In the formula (1), $R^4$ represents an alkylene group of 1 to 4 carbon atoms which may have a substituent or a fluorinated alkylene group of 1 to 4 carbon atoms which may have a substituent; $L^2$ represents a single bond or a divalent linking group; and $R^5$ represents a hydrocarbon group of 3 to 30 carbon atoms which may have a substituent; in the formula (2), $R^6$ represents an alky group which may have a substituent or a fluorinated alkyl group which may have a substituent; $L^3$ represents a single bond or a divalent linking group; $Y^{10}$ represents a —$SO_2$— or a —CO—; and $R^7$ represents a hydrocarbon group which may have a substituent.

<<Compound (I)>>

The compound (I) of the present invention is represented by general formula (I) shown below.

In general formula (I), R, $R^1$, $R^2$, $R^3$, $L^1$ and A are the same as defined for R, $R^1$, $R^2$, $R^3$, $L^1$ and A in the formula (a0).

The compound (I) is useful as a monomer used in the production of the component (A).

[Chemical Formula 74]

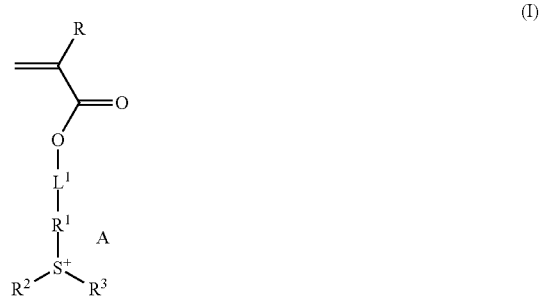

(I)

In the formula, R represents a hydrogen atom, an alkyl group of 1 to 5 carbon atoms or a halogenated alkyl group of 1 to 5 carbon atoms; $R^1$ represents a divalent aromatic cyclic group; each of $R^2$ and $R^3$ independently represents an aryl group which may have a substituent, an alkyl group which may have a substituent or an alkenyl group which may have a substituent, wherein $R^2$ and $R^3$ may be mutually bonded to form a ring with the sulfur atom; $L^1$ represents a single bond or a divalent linking group; and A represents an anion represented by general formula (1) or (2) shown below.

[Chemical Formula 75]

$$R^5\text{-}L^2\text{-}R^4\text{—}SO_3^- \qquad (1)$$

$$R^7\text{-}L^3\text{-}Y^{10}\text{—}N^-\text{—}SO_2\text{—}R^6 \qquad (2)$$

In the formula (1), $R^4$ represents an alkylene group of 1 to 4 carbon atoms which may have a substituent or a fluorinated alkylene group of 1 to 4 carbon atoms which may have a substituent; $L^2$ represents a single bond or a divalent linking group; and $R^5$ represents a hydrocarbon group of 3 to 30 carbon atoms which may have a substituent; in the formula (2), $R^6$ represents an alky group which may have a substituent or a fluorinated alkyl group which may have a substituent; $L^3$ represents a single bond or a divalent linking group; $Y^{10}$ represents a —$SO_2$— or a —CO—; and $R^7$ represents a hydrocarbon group which may have a substituent.

<Production Method of Compound (I)>

The method for producing the compound (I) is not particularly limited, and the compound (I) can be produced by a conventional method. For example, a production method including a step of reacting a compound represented by the general formula (II-1) shown below (hereafter, referred to as "compound (II-1)") with a compound represented by general formula (II-2) shown below (hereafter, referred to as "compound (II-12)"), thereby obtaining a compound represented by general formula (II-3) shown below (hereafter, referred to as "compound (II-3)"), and a step of reacting the compound (II-3) with a compound represented by general formula (II-4)

shown below (hereafter, referred to as "compound (II-4)"), thereby obtaining a compound represented by the general formula (I), can be given.

[Chemical Formula 76]

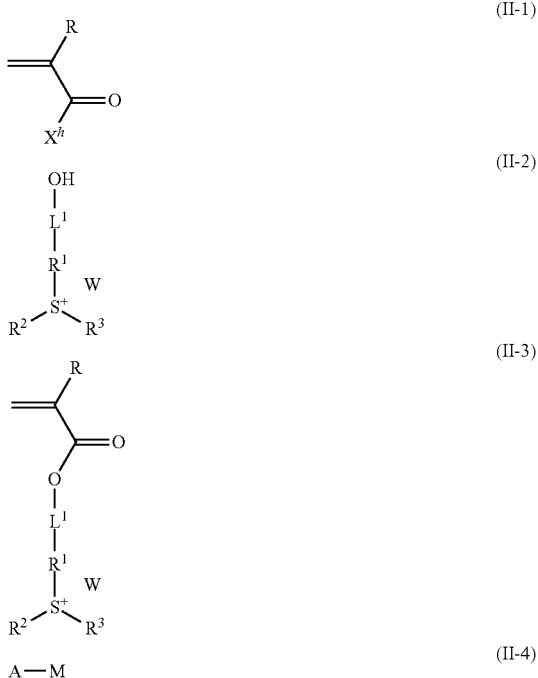

In the formulas, R, $L^1$, $R^1$, $R^2$, $R^3$ and A are the same as defined above; and $X^h$ represents a hydroxy group or a halogen atom; W represents a counteranion; and M represents a countercation.

Examples of halogen atoms for $X^h$ include a bromine atom, a chlorine atom, an iodine atom and a fluorine atom.

As $X^h$, in terms of reactivity, a hydroxy group, a bromine atom or a chlorine atom is preferable, and a hydroxy group is particularly desirable.

The counteranion for W is not particularly limited. Examples of counteranion include a halogen ion, a p-toluenesulfonate ion, an alkylsulfonate ion, an alkylsulfate ion and a benzenesulfonate ion. Of these, a halogen ion and an alkylsulfonic acid ion are preferable.

As the halogen ion, a bromine ion or a chlorine ion is preferable.

An example of such alkylsulfonic acid ion includes an ion represented by formula $R^{04}—SO_3^-$ [in the formula, $R^{04}$ represents an alkyl group of 1 to 5 carbon atoms]. The $R^{04}$ group is preferably an alkyl group of 1 to 3 carbon atoms, and a methyl group is particularly preferable.

The countercation for M is not particularly limited. Preferable examples of countercation include an alkali metal and an organic cation.

Examples of the alkali metal for M include sodium, potassium and lithium.

The organic cation for M is not particularly limited as long as it can form a salt with A or A'. Preferable examples of organic cation include an organic ammonium ion.

An organic ammonium ion is an ion in which 1 to 4 of the hydrogen atoms within the ammonium ion ($NH_4^+$) have been substituted with organic groups. Examples of the organic group include a hydrocarbon group which may have a substituent. The hydrocarbon group preferably has 1 to 30 carbon atoms. As the hydrocarbon group of 3 to 30 carbon atoms, the same groups as those described above for $R^5$ in the formula (1) can be given. Examples of the substituent which the hydrocarbon group may have include the same substituents as those which the hydrocarbon group represented by $R^5$ in the formula (1) may have.

Examples of the organic ammonium ion include those represented by general formula (0-1) shown below.

[Chemical Formula 77]

In the formula, each of $Y^3$ to $Y^6$ independently represents a hydrogen atom or a hydrocarbon group which may have a substituent, provided that at least one of $Y^3$ to $Y^6$ represents a hydrocarbon group; and at least two of $Y^3$ to $Y^6$ may be mutually bonded to form a ring.

In formula (0-1), each of $Y^3$ to $Y^6$ independently represents a hydrogen atom or a hydrocarbon group which may have a substituent, provided that at least one of $Y^3$ to $Y^6$ represents a hydrocarbon group.

As the hydrocarbon group for $Y^3$ to $Y^6$, the same hydrocarbon groups described as an organic group with which a hydrogen atom in the ammonium ion ($NH_4^+$) is substituted can be mentioned.

The hydrocarbon group may be either an aliphatic hydrocarbon group or an aromatic hydrocarbon group. When the hydrocarbon group is an aliphatic hydrocarbon group, it is particularly desirable that the hydrocarbon group is an alkyl group of 1 to 12 carbon atoms which may have a substituent.

At least one of $Y^3$ to $Y^6$ is a hydrocarbon group, and it is preferable that two or three groups are hydrocarbon groups.

At least two of $Y^3$ to $Y^6$ may be mutually bonded to form a ring. For example, two of $Y^3$ to $Y^6$ may be bonded to form a ring, three of $Y^3$ to $Y^6$ may be bonded to form a ring, or two of $Y^3$ to $Y^6$ may be bonded to form a ring, and the remaining two may be bonded to form another ring.

The ring which is formed by at least two of $Y^3$ to $Y^6$ bonded together with the nitrogen atom (i.e., the heterocycle containing nitrogen as a hetero atom) may be either an aliphatic heterocycle, or an aromatic heterocycle. Further, the heterocycle may be either a monocyclic group or a polycyclic group.

Specific examples of the ammonium ion represented by general formula (0-1) include ammonium ions (primary, secondary and tertiary ammonium ions) derived from an amine, and quaternary ammonium ion.

As the ammonium ion derived from the aforementioned amine, an ammonium ion in which 1 to 3 of $Y^3$ to $Y^6$ represents the aforementioned hydrocarbon group, and in which a hydrogen atom is bonded to the nitrogen atom in the amine thereof to form a cation, can be given. The amine may be either an aliphatic amine or an aromatic amine. Examples of the aliphatic amine or an aromatic amine include the aliphatic amine or an aromatic amine as those described in the explanation of the compound (D).

As the amine, an aliphatic amine is preferable, and an amine in which at least one hydrogen atom of ammonia ($NH_3$) has been substituted with an alkyl group or hydroxyalkyl group of no more than 12 carbon atoms (i.e., alkylamines or alkylalcoholamines), or a cyclic amine is particularly desirable.

The quaternary ammonium ion is an ion in which all of $Y^3$ to $Y^6$ represents hydrocarbon group, and the hydrocarbon group is preferably an alkyl group. Examples of the quaternary ammonium ion include a tetramethylammonium ion, a tetraethylammonium ion and a tetrabutylammonium ion.

As the ammonium ion represented by general formula (0-1), a group in which at least one of $Y^3$ to $Y^6$ is an alkyl group and at least one is a hydrogen atom is particularly desirable.

Especially, a group in which three of $Y^3$ to $Y^6$ are alkyl groups, and the remaining one is a hydrogen atom (i.e., a trialkylammonium ion), or a group in which two of $Y^3$ to $Y^6$ are alkyl groups, and the remaining two are hydrogen atoms (i.e., dialkylammonium ion) is preferable.

It is preferable that each of the alkyl groups within the trialkylammonium ion or the dialkylammonium ion independently has 1 to 10 carbon atoms, more preferably 1 to 8, and most preferably 1 to 5. Specific examples include a methyl group, an ethyl group, a propyl group, a butyl group, a pentyl group, a hexyl group, a heptyl group, an octyl group, a nonyl group and a decyl group. Among these, an ethyl group is particularly desirable.

As the compounds (II-1) to (II-3), commercially available compounds may be used, or the compounds may be synthesized by a conventional method.

The method of reacting the compound (II-1) and compound (II-2) is not particularly limited. For example, in the presence of a base and condensation agent, a compound (II-2) is added to a solution obtained by dissolving a compound (II-1) in a solvent, thereby obtaining the aforementioned compound (II-3).

Examples of the base include inorganic bases such as sodium hydride, $K_2CO_3$ and $Cs_2CO_3$, and organic bases such as triethylamine, 4-dimethylaminopyridine (DMAP) and pyridine.

Examples of condensation agents include carbodiimide reagents such as ethyldiisopropylaminocarbodiimide hydrochloride (EDCI), dicyclohexylcarboxylmide (DCC), diisopropylcarbodiimide and carbodiimidazole, as well as tetraethyl pyrophosphate and benzotriazole-N-hydroxytrisdimethylaminophosphonium hexafluorophosphate (Bop reagent).

If desired, an acid may be used. As the acid, any of those which are typically used in dehydration/condensation can be used. Specific examples of such acids include inorganic acids such as hydrochloric acid, sulfuric acid and phosphoric acid, and organic acids such as methanesulfonic acid, trifluoromethanesulfonic acid, benzenesulfonic acid and p-toluenesulfonic acid. These acids can be used individually, or in a combination of two or more.

The method of reacting the compound (II-3) and the compound (II-4) is not particularly limited, and can be conducted by a conventional salt substitution method. For example, the reaction may be conducted by dissolving the compound (II-4) and the compound (II-3) in a solvent such as water, dichloromethane, acetonitrile, methanol or chloroform, followed by stirring or the like.

The reaction temperature is preferably 0 to 150° C., and more preferably 0 to 100° C.

The reaction time depends on the reactivity of the compounds (II-3) and (II-4), the reaction temperature or the like. However, in general, the reaction time is preferably 0.5 to 10 hours, and more preferably 1 to 5 hours.

After the reaction, the compound (I) within the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

The structure of the compound (I) obtained in the above-described manner can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

EXAMPLES

As follows is a description of examples of the present invention, although the scope of the present invention is by no way limited by these examples.

In the following examples, a compound represented as "compound A" in a chemical formula is designated as "compound (A)", and the same applies for compounds represented by other formulas.

In the NMR analysis, the internal standard for $^1$H-NMR and $^{13}$C-NMR was tetramethylsilane (TMS). The internal standard for $^{19}$F-NMR was hexafluorobenzene (provided that the peak of hexafluorobenzene was regarded as −160 ppm).

Synthesis Example 1

Synthesis of Compound A 11.4 g of methacrylic acid and 500 g of dichloromethane were added to a three-necked flask under a nitrogen atmosphere, and cooled to 10° C. or lower. Then, 3.25 g of N,N-dimethylaminopyridine was added thereto, stirring was conducted at a temperature of 10° C. or lower for 5 minutes, and 63.6 g of ethyl-N,N-dimethylaminopropylcarbodiimide was added thereto. Thereafter, stirring was conducted for 10 minutes, and 42.8 g of a compound 1 was added thereto. Then, the temperature of the resultant was elevated to room temperature, and stirring was conducted at room temperature for 15 hours, followed by washing with a diluted hydrochloric acid and pure water. The resulting organic phase was dropwise added to 2,400 g of n-hexane and precipitated, thereby obtaining 43.1 g of a compound A.

The compound A was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, CH$_2$=C), 5.81(s, 1H, CH$_2$=C), 2.31 (s, 3H, CH$_3$SO$_3^-$), 2.20-2.41(m, 6H, CH$_3$), 2.06(s, 3H, CH$_3$)

From the results shown above, it was confirmed that the compound A had a structure shown below.

[Chemical Formula 78]

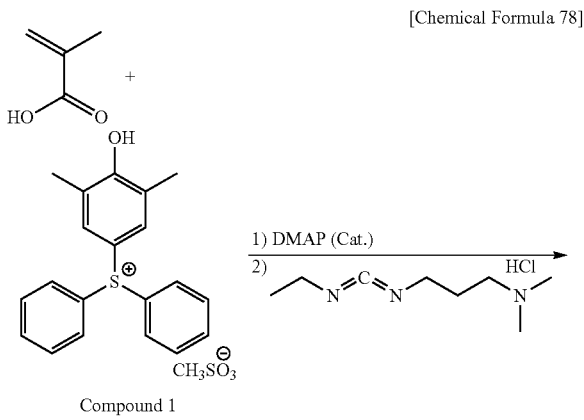

Compound 1

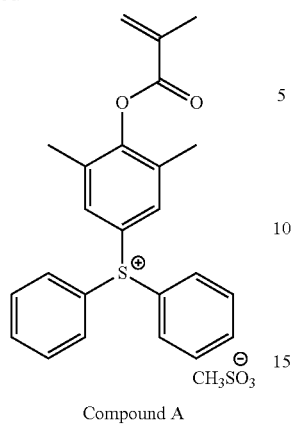

Compound A

Synthesis Example 2

Synthesis of Compound A-1

5 g of a compound A, 65 g of dichloromethane and 65 g of pure water were mixed together, and 2.85 g of an anion A-1 was added thereto, followed by stirring at room temperature for one night. Then, the organic phase was separated and washed with 65 g of pure water four times. Thereafter, dichloromethane was distilled off under reduced pressure, and the resultant was dried under reduced pressure, thereby obtaining 6.1 g of a compound A-1.

The compound A-1 was analyzed by NMR. The results are shown below.

$^{1}$H-NMR (DMSO-d6, 400 MHz):δ(ppm)=7.74-7.84(m, 10H, ArH), 7.61(s, 2H, ArH), 6.41(s, 1H, CH$_2$=C), 5.81-5.93(m, 2H, CH$_2$=C, anion CH), 5.41(dd, 1H, anion CH), 5.21(dd, 1H, anion CH), 4.45(s, 2H, anion CH$_2$), 2.20-2.41 (m, 6H, CH$_3$), 2.06(s, 3H, CH$_3$)

$^{19}$F-NMR (DMSO-d6, 376 MHz):δ(ppm)=−80.0, −113.0

From the results shown above, it was confirmed that the compound A-1 had a structure shown below.

[Chemical Formula 79]

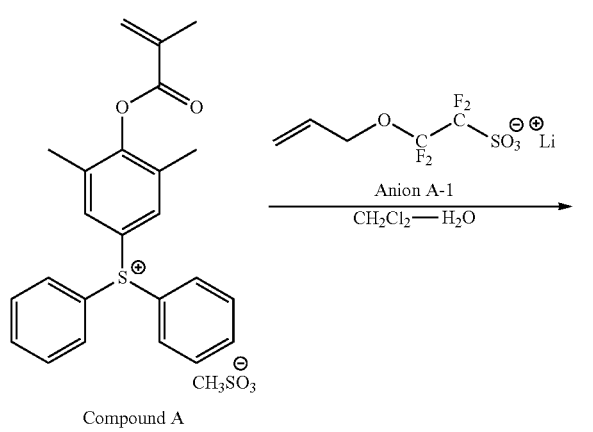

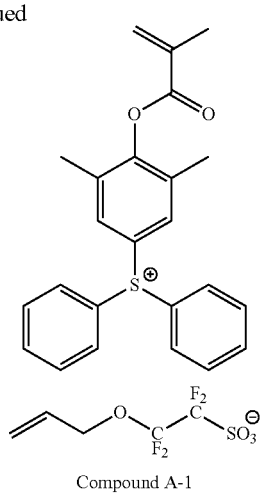

Compound A-1

Synthesis Example 3

Synthesis of Compound A-2

A compound A-2 was synthesized in the same manner as in Synthesis Example 2, except that the anion A-1 was changed to an anion A-2 indicated in Table 1. The obtained compound A-2 was analyzed by NMR. The results are shown below.

$^{1}$H-NMR (DMSO-d6, 400 MHz):δ(ppm)=7.51-7.96(m, 19H, ArH+Naph), 6.41(s, 1H, CH$_2$=C), 5.81(s, 1H, CH$_2$=C), 5.10(s, 2H, anion CH$_2$), 2.20-2.41(m, 6H, CH$_3$), 2.06(s, 3H, CH$_3$)

$^{19}$F-NMR (DMSO-d6, 376 MHz):δ(ppm)=−80.5, −113.7

From the results shown above, it was confirmed that the compound A-2 had a structure shown below.

[Chemical Formula 80]

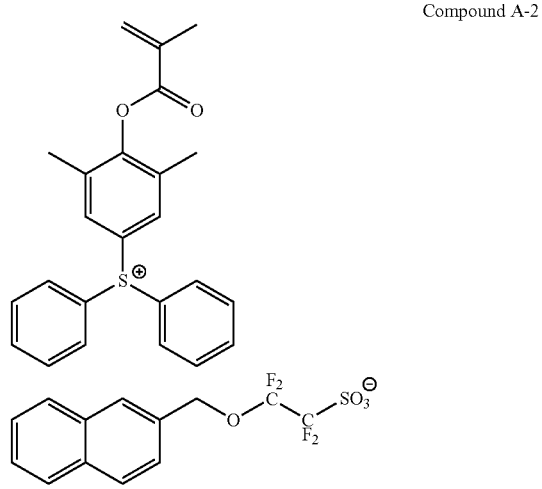

Compound A-2

Synthesis Example 4

Synthesis of Compound A-3

A compound A-3 was synthesized in the same manner as in Synthesis Example 2, except that the anion A-1 was changed to an anion A-3 indicated in Table 1. The obtained compound A-3 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, CH$_2$=C), 5.81(s, 1H, CH$_2$=C), 2.20-2.41(m, 6H, CH$_3$), 2.10(m, 6H, CH$_3$+Adamantane), 1.96(s, 6H, Adamantane), 1.56(s, 6H, Adamantane)

$^{19}$F-NMR (DMSO-d6, 376 MHz):δ(ppm)=−70.1, −113.4

From the results shown above, it was confirmed that the compound A-3 had a structure shown below.

[Chemical Formula 81]

Compound A-3

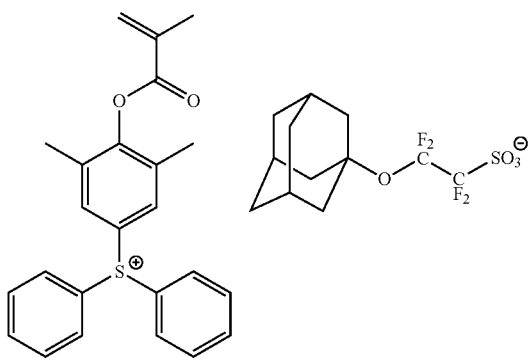

Synthesis Example 5

Synthesis of Compound A-4

A compound A-4 was synthesized in the same manner as in Synthesis Example 2, except that the anion A-1 was changed to an anion A-4 indicated in Table 1. The obtained compound A-4 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, CH$_2$=C), 5.81(s, 1H, CH$_2$=C), 2.20-2.41(m, 6H, CH$_3$), 2.06(s, 3H, CH$_3$), 1.55-1.88(m, 15H, Adamantane)

$^{19}$F-NMR (DMSO-d6, 376 MHz):δ(ppm)=−74.5

From the results shown above, it was confirmed that the compound A-4 had a structure shown below.

[Chemical Formula 82]

Compound A-4

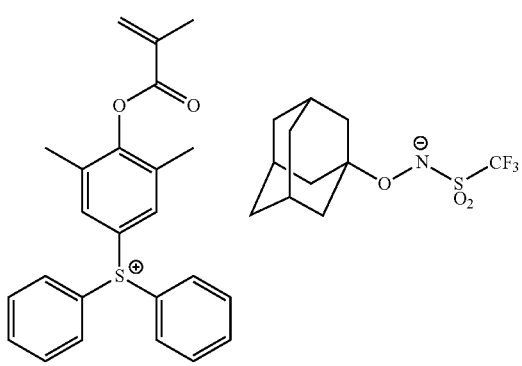

Synthesis Example 6

Synthesis of Compound A-5

A compound A-5 was synthesized in the same manner as in Synthesis Example 2, except that the anion A-1 was changed to an anion A-5 indicated in Table 1. The obtained compound A-5 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, CH$_2$=C), 5.81(s, 1H, CH$_2$=C), 4.19 (s, 2H, anion CH$_2$), 2.20-2.41(m, 6H, CH$_3$), 2.06(s, 3H, CH$_3$), 1.55-1.87(m, 15H, Adamantane)

$^{19}$F-NMR (DMSO-d6, 376 MHz):δ(ppm)=−77.7

From the results shown above, it was confirmed that the compound A-5 had a structure shown below.

[Chemical Formula 83]

Compound A-5

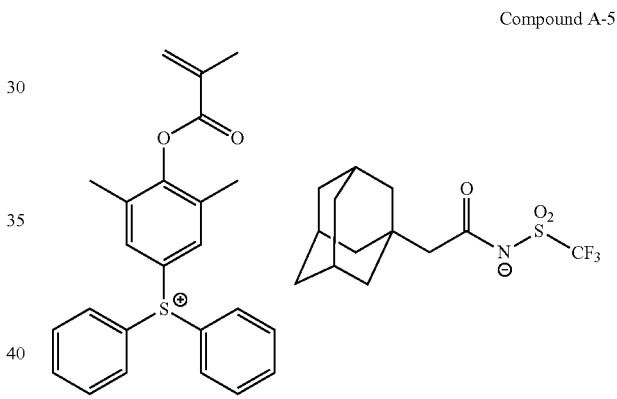

Synthesis Example 7

Synthesis of Compound A-6

A compound A-6 was synthesized in the same manner as in Synthesis Example 2, except that the anion A-1 was changed to an anion A-6 indicated in Table 1. The obtained compound A-6 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, CH$_2$=C), 5.81(s, 1H, CH$_2$=C), 2.77-2.81(m, 1H, Cyclohexyl), 2.20-2.41(m, 6H, CH$_3$), 2.04-2.08(m, 5H, CH$_3$+Cyclohexyl), 1.73-1.75(m, 2H, Cyclohexyl), 1.56-1.59(m, 1H, Cyclohexyl), 1.07-1.33 (m, 5H, Cyclohexyl)

$^{19}$F-NMR (DMSO-d6, 376 MHz):δ(ppm)=−74.7

From the results shown above, it was confirmed that the compound A-6 had a structure shown below.

[Chemical Formula 84]

Compound A-6

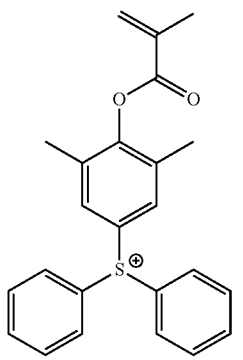

Synthesis Example 8

Synthesis of Compound A-7

A compound A-7 was synthesized in the same manner as in Synthesis Example 2, except that the anion A-1 was changed to an anion A-7 indicated in Table 1. The obtained compound A-7 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, CH$_2$=C), 5.81(s, 1H, CH$_2$=C), 2.20-2.41(m, 6H, CH$_3$), 2.13(m, 3H, Adamantane), 2.06(s, 3H, CH$_3$), 1.99(m, 6H, Adamantane), 1.59(s, 6H, Adamantane)

$^{19}$F-NMR (DMSO-d6, 376 MHz):δ(ppm)=−69.2, −76.0, −112.9

From the results shown above, it was confirmed that the compound A-7 had a structure shown below.

[Chemical Formula 85]

Compound A-7

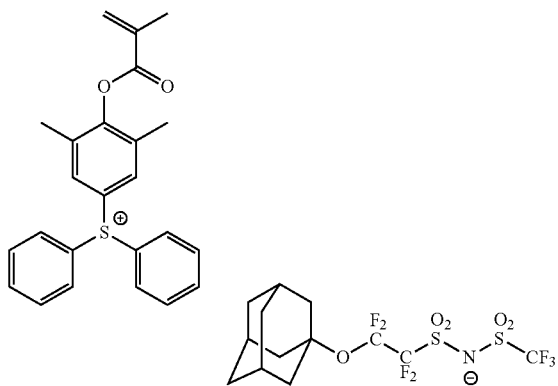

Synthesis Example 9

Synthesis of Compound (A-8)

A compound A-8 was synthesized in the same manner as in Synthesis Example 2, except that the anion A-1 was changed to an anion A-8 indicated in Table 1. The obtained compound A-8 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, CH$_2$=C), 5.81(s, 1H, CH$_2$=C), 4.40-4.50(m, 4H, anion CH$_2$), 2.20-2.41(m, 6H, CH$_3$), 2.06(s, 3H, CH$_3$)

$^{19}$F-NMR (DMSO-d6, 376 MHz):δ(ppm)=−106.7, −154.0, −160.0, −161.5

From the results shown above, it was confirmed that the compound A-8 had a structure shown below.

[Chemical Formula 86]

Compound A-8

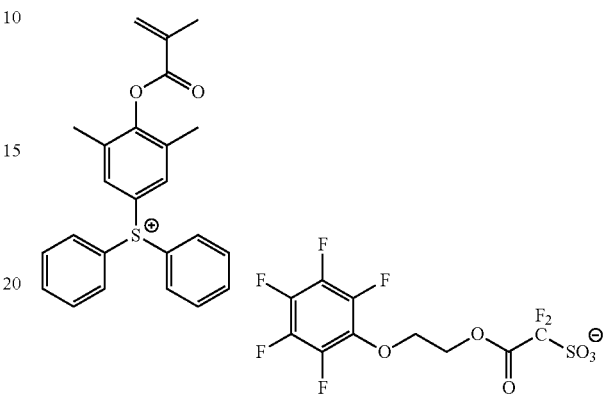

Synthesis Example 10

Synthesis of Compound A-9

A compound A-9 was synthesized in the same manner as in Synthesis Example 2, except that the anion A-1 was changed to an anion A-9 indicated in Table 1. The obtained compound A-9 was analyzed by NMR. The results are shown below.

$^1$H-NMR (DMSO-d6, 400 MHz):δ(ppm)=8.74-8.82(m, 2H, Py-H), 7.74-7.84(m, 12H, ArH+Py-H), 7.61(s, 2H, ArH), 6.41(s, 1H, CH$_2$=C), 5.81(s, 1H, CH$_2$=C), 4.54-4.61(m, 4H, anion CH$_2$CH$_2$), 2.20-2.41(m, 6H, CH$_3$), 2.06(s, 3H, CH$_3$)

$^{19}$F-NMR (DMSO-d6, 376 MHz):δ(ppm)=−106.5

From the results shown above, it was confirmed that the compound A-9 had a structure shown below.

[Chemical Formula 87]

Compound A-9

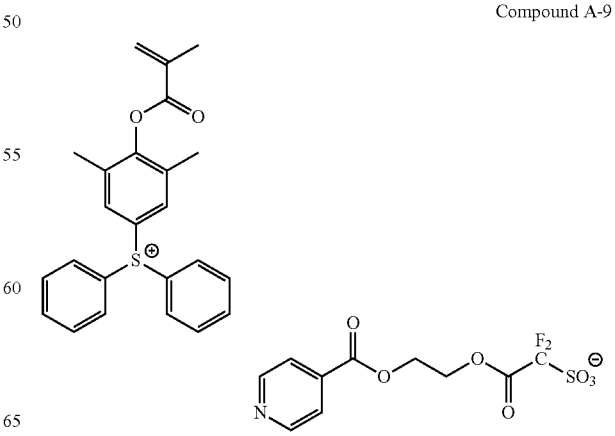

Synthesis Example 11

Synthesis of Compound A-10

A compound A-10 was synthesized in the same manner as in Synthesis Example 2, except that the anion A-1 was changed to an anion A-10 indicated in Table 2. The obtained compound A-10 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, CH$_2$=C), 5.81(s, 1H, CH$_2$=C), 5.46 (t, 1H, oxo-norbornane), 4.97(s, 1H, oxo-norbornane), 4.71(d, 1H, oxo-norbornane), 4.57(d, 1H, oxo-norbornane), 2.69-2.73(m, 1H, oxo-norbornane), 2.06-2.41 (m, 11H, CH$_3$+oxo-norbornane)

$^{19}$F-NMR (DMSO-d6, 376 MHz):δ(ppm)=−107.1

From the results shown above, it was confirmed that the compound A-10 had a structure shown below.

[Chemical Formula 88]

Compound A-10

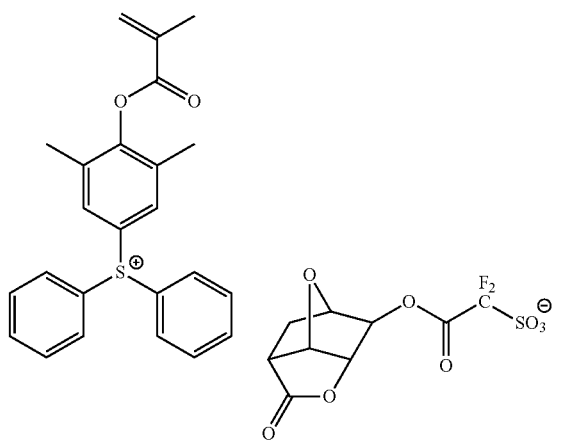

Synthesis Example 12

Synthesis of Compound A-11

A compound A-11 was synthesized in the same manner as in Synthesis Example 2, except that the anion A-1 was changed to an anion A-11 indicated in Table 2. The obtained compound A-11 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, CH$_2$=C), 5.81(s, 1H, CH$_2$=C), 4.41 (t, 2H, anion CH$_2$), 4.23(t, 2H, anion CH$_2$), 2.20-2.41(m, 6H, CH$_3$), 2.06(s, 3H, CH$_3$), 0.79-2.89 (m, 21H, Undecanoyl)

$^{19}$F-NMR (DMSO-d6, 376 MHz):δ(ppm)=−106.8

From the results shown above, it was confirmed that the compound A-11 had a structure shown below.

[Chemical Formula 89]

Compound A-11

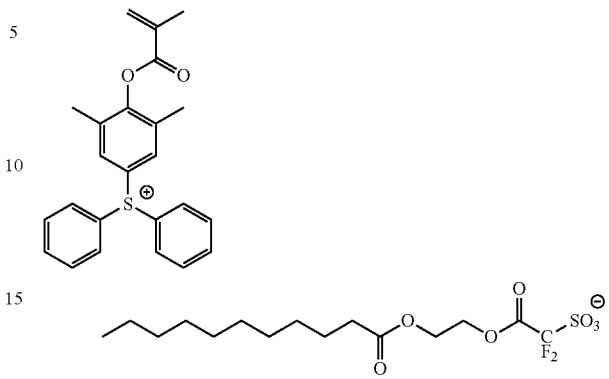

Synthesis Example 13

Synthesis of Compound A-12

A compound A-12 was synthesized in the same manner as in Synthesis Example 2, except that the anion A-1 was changed to an anion A-12 indicated in Table 2. The obtained compound A-12 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, CH$_2$=C), 5.81(s, 1H, CH$_2$=C), 4.49-4.51(m, 2H, anion O—CH$_2$), 4.30-4.32 (m, 2H, anion O—CH$_2$), 2.20-2.41(m, 8H, CH$_3$+anion CO—CH$_2$), 2.06(s, 3H, CH$_3$), 1.51-1.56(m, 2H, CH$_2$), 1.15-1.35(m, 6H, CH$_2$), 0.87(t, 3H, CH$_3$)

$^{19}$F-NMR (DMSO-d6, 376 MHz):δ(ppm)=−106.8

From the results shown above, it was confirmed that the compound A-12 had a structure shown below.

[Chemical Formula 90]

Compound A-12

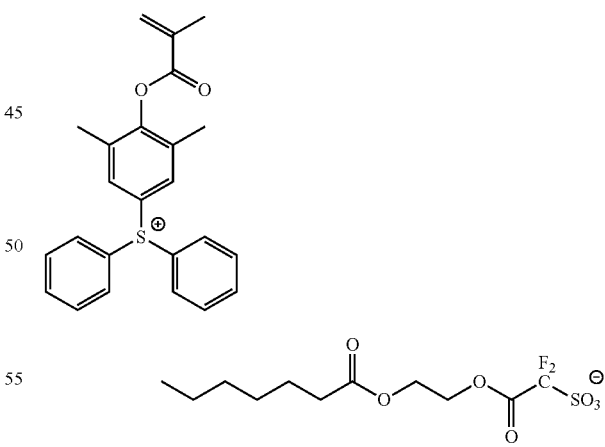

Synthesis Example 14

Synthesis of Compound A-13

A compound A-13 was synthesized in the same manner as in Synthesis Example 2, except that the anion A-1 was changed to an anion A-13 indicated in Table 2. The obtained compound A-13 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, $CH_2$=C), 5.81(s, 1H, $CH_2$=C), 4.40 (t, 2H, anion $CH_2$), 4.21(t, 2H, anion $CH_2$), 2.20-2.41(m, 6H, $CH_3$), 2.06(s, 3H, $CH_3$), 1.61-1.98 (m, 15H, Adamantane)

$^{19}$F-NMR (DMSO-d6, 376 MHz):δ(ppm)=−106.6

From the results shown above, it was confirmed that the compound A-13 had a structure shown below.

[Chemical Formula 91]

Compound A-13

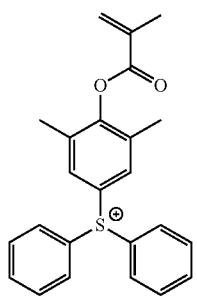
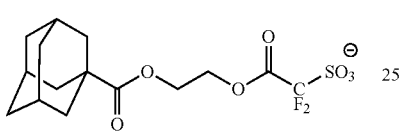

Synthesis Example 15

Synthesis of Compound A-14

A compound A-14 was synthesized in the same manner as in Synthesis Example 2, except that the anion A-1 was changed to an anion A-14 indicated in Table 2. The obtained compound A-14 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, $CH_2$=C), 5.81(s, 1H, $CH_2$=C), 4.40 (t, 2H, anion $CH_2$), 4.20(t, 2H, anion $CH_2$), 2.20-2.41(m, 6H, $CH_3$), 2.06(m, 5H, $CH_3$+anion $CH_2$), 1.53-1.95(m, 15H, Adamantane)

$^{19}$F-NMR (DMSO-d6, 376 MHz):δ(ppm)=−111.2

From the results shown above, it was confirmed that the compound A-14 had a structure shown below.

[Chemical Formula 92]

Compound A-14

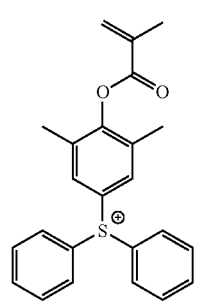
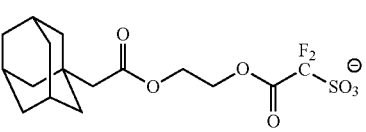

Synthesis Example 16

Synthesis of Compound A-15

A compound A-15 was synthesized in the same manner as in Synthesis Example 2, except that the anion A-1 was changed to an anion A-15 indicated in Table 2. The obtained compound A-15 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, $CH_2$=C), 5.81(s, 1H, $CH_2$=C), 4.55 (t, 2H, $CF_2CH_2$), 2.20-2.41(m, 6H, $CH_3$), 2.06(s, 3H, $CH_3$), 1.94(m, 3H, Adamantane), 1.82(m, 6H, Adamantane), 1.64(m, 6H, Ad)

$^{19}$F-NMR (DMSO-d6, 376 MHz):δ(ppm)=−111.2

From the results shown above, it was confirmed that the compound A-15 had a structure shown below.

[Chemical Formula 93]

Compound A-15

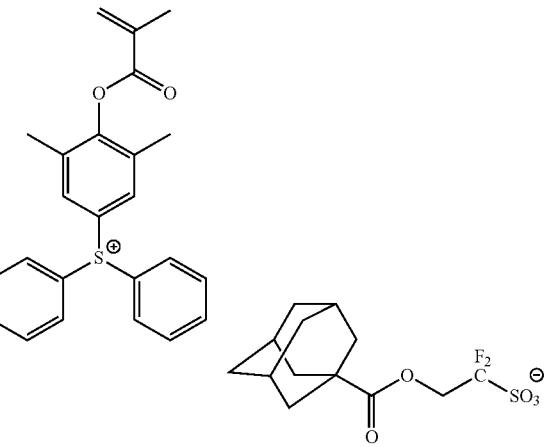

Synthesis Example 17

Synthesis of Compound A-16

A compound A-16 was synthesized in the same manner as in Synthesis Example 2, except that the anion A-1 was changed to an anion A-16 indicated in Table 2. The obtained compound A-16 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, $CH_2$=C), 5.81(s, 1H, $CH_2$=C), 4.78 (m, 1H, anion CH), 4.66(t, 1H, anion CH), 3.88(t, 1H, anion CH), 3.34(m, 1H, CH), 1.73-2.49(m, 14H, $CH_3$+anion CH+anion $CH_2$)

$^{19}$F-NMR (DMSO-d6, 376 MHz):δ(ppm)=−107.7

From the results shown above, it was confirmed that the compound A-16 had a structure shown below.

[Chemical Formula 94]

Compound A-16

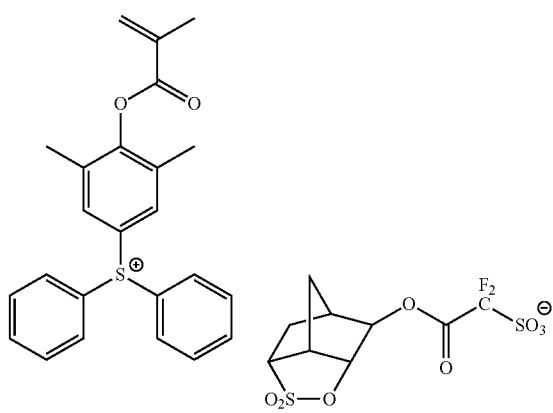

Synthesis Example 18

Synthesis of Compound A-17

A compound A-17 was synthesized in the same manner as in Synthesis Example 2, except that the anion A-1 was changed to an anion A-17 indicated in Table 2. The obtained compound A-17 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, CH$_2$=C), 5.81(s, 1H, CH$_2$=C), 4.50-4.54(m, 4H, anion OCH$_2$CH$_2$O), 3.57(d, 1H, anion CH$_2$SO$_2$), 3.36(sd, 1H, anion CH$_2$SO$_2$), 2.24-2.34 (m, 2H, anion CH$_2$), 2.20-2.41(m, 6H, CH$_3$), 2.07(m, 4H, CH$_3$+anion CH), 1.92-1.99(m, 2H, anion CH$_2$), 1.56-1.62(m, 1H, anion CH), 1.42-1.45(m, 1H, anion CH), 1.04(s, 3H, anion CH$_3$), 0.84(s, 3H, anion CH$_3$)

$^{19}$F-NMR (DMSO-d6, 376 MHz):δ(ppm)=−107.7

From the results shown above, it was confirmed that the compound A-17 had a structure shown below.

[Chemical Formula 95]

Compound A-17

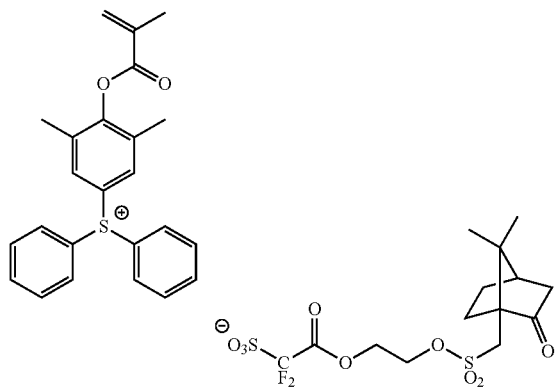

Synthesis Example 19

Synthesis of Compound A-18

A compound A-18 was synthesized in the same manner as in Synthesis Example 2, except that the anion A-1 was changed to an anion A-18 obtained in Anion Synthesis Example 1 described later. The obtained compound A-18 was analyzed by NMR. The results are shown below.

$^1$H-NMR (DMSO-d6, 400 MHz):δ(ppm)=7.74-7.84(m, 10H, ArH), 7.61(s, 2H, ArH), 6.41(s, 1H, CH$_2$=C), 5.81(s, 1H, CH$_2$=C), 4.22 (s, 2H, anion CH$_2$O), 4.05(t, 2H, anion CH$_2$CF$_2$), 3.13(q, 6H, anion CH$_2$CH$_3$), 2.20-2.41(m, 8H, CH$_3$+Adamantane), 2.06(s, 3H, CH$_3$), 1.53-1.99(m, 15H, Adamantane+CH$_3$), 1.20(t, 9H, CH$_2$CH$_3$)

$^{19}$F-NMR (DMSO-d6, 376 MHz):δ(ppm)=−107.7

From the results shown above, it was confirmed that the compound A-18 had a structure shown below.

[Chemical Formula 96]

Compound A-18

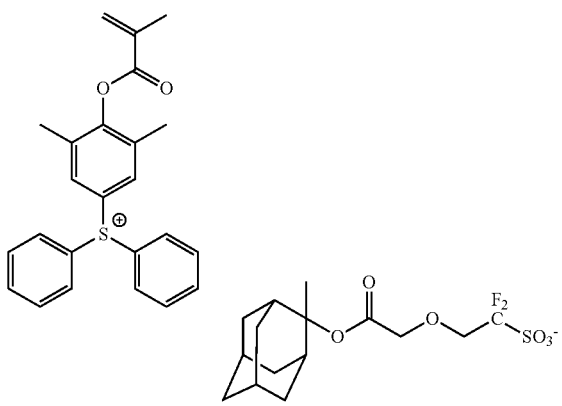

TABLE 1

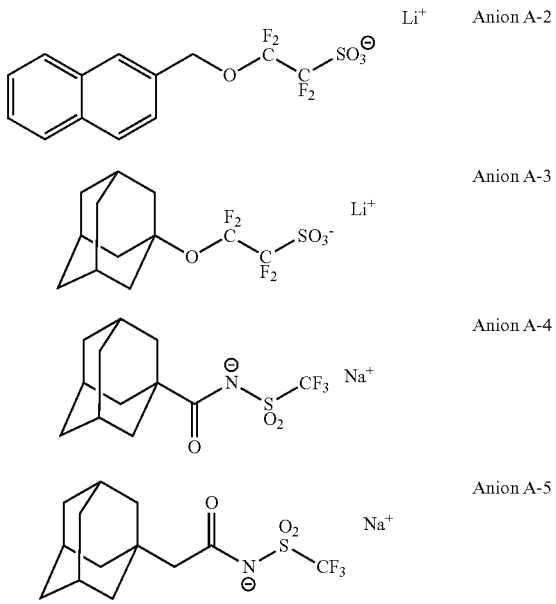

TABLE 1-continued
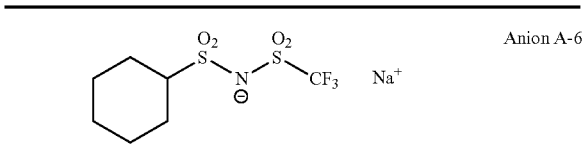
Anion A-6
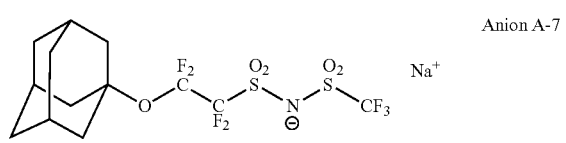
Anion A-7
TABLE 1-continued
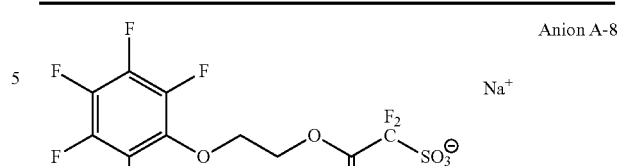
Anion A-8
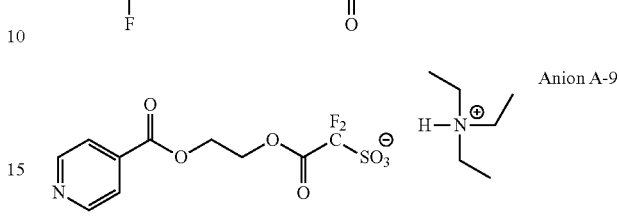
Anion A-9
TABLE 2
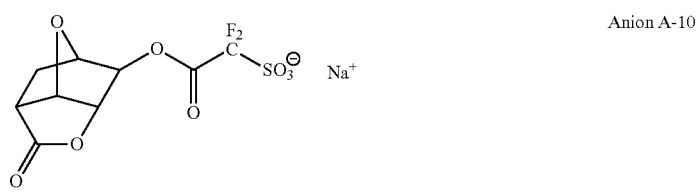
Anion A-10
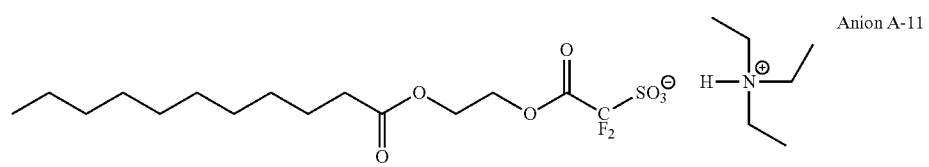
Anion A-11
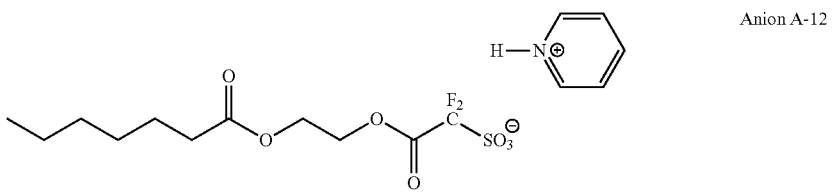
Anion A-12
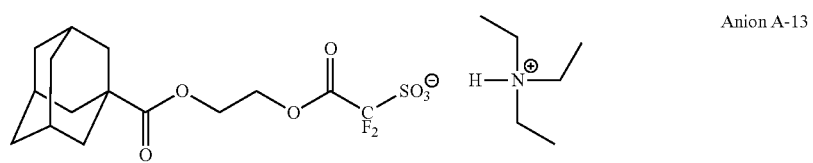
Anion A-13
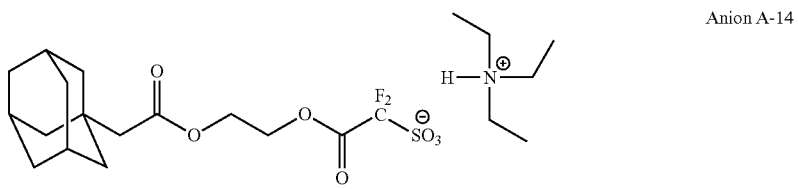
Anion A-14
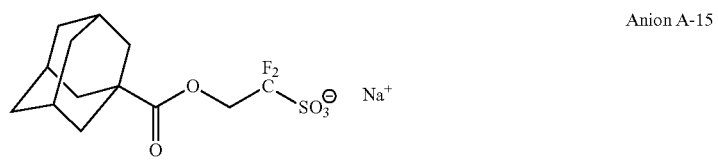
Anion A-15

TABLE 2-continued

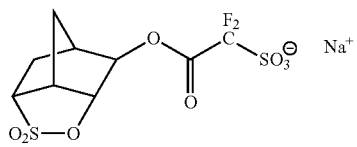

Anion A-16

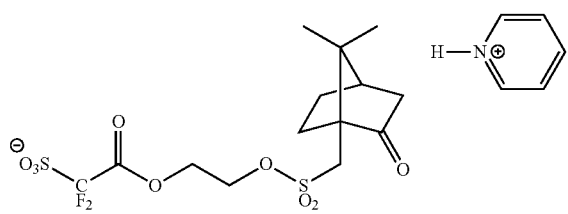

Anion A-17

Anion Synthesis Example 1

Synthesis of Anion A-18

7.2 g of the compound (18-1) and 72.4 g of THF were mixed under a nitrogen atmosphere, and cooled to 10° C. Then, 2.8 g of sodium hydride having a purity of 60% was slowly added thereto, and stirring was conducted at 10° C. for 5 minutes, followed by dropwise adding a THF solution of 16.9 g of the compound (18-2). The reaction solution was heated, and stirring was conducted under reflux for 4 hours. After the reaction was completed, 15.1 g of triethylamine hydrochloride was added thereto to inactivate the unreacted sodium hydride. 185 g of pure water was added to the reaction mixture, and 185 g t-butyl methyl ether was further added, and stirring was conducted for 5 minutes at room temperature. Then, the aqueous phase was separated, and washed repeatedly with t-butyl methyl ether. Thereafter, the aqueous phase was extracted with dichloromethane, and the organic phase was distilled under reduced pressure. The resulting oily material was dried under reduced pressure, thereby obtaining 9.7 g of an objective compound (Anion A-18).

The obtained compound was analyzed by NMR, and the structure thereof was identified by the following results.

$^1$H-NMR (400 MHz, DMSO-d$_6$):δ(ppm)=8.82(brs, 1H, NH), 4.22(s, 2H, CH$_2$O), 4.05(t, 2H, CH$_2$CF$_2$), 3.13(q, 6H, CH$_2$CH$_3$), 2.24(brs, 2H, Adamantane), 1.53-1.99(m, 15H, Adamantane+CH$_3$), 1.20(t, 9H, CH$_2$CH$_3$)

$^{19}$F-NMR (376 MHz, DMSO-d$_6$):δ(ppm)=−111.0

From the analysis results shown above, it was confirmed that the obtained compound had a structure shown below.

[Chemical Formula 97]

HO\_CF$_2$\_SO$_3^-$ Na$^+$ (18-1)

+

[structure with Br, adamantyl ester]

(18-2)

1) NaH/THF, reflux
2) H—N$^+$(Et)$_3$ Cl$^-$

-continued

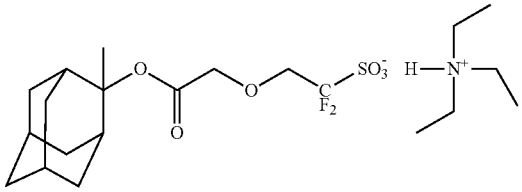

Anion A-18

Polymer Synthesis Example 1

Synthesis of Polymeric Compound 1

5.00 g (15.81 mmol) of the compound 1, 1.74 g (6.64 mmol) of the compound 2, 2.19 g (9.28 mmol) of the compound 3 and 3.98 g (5.70 mmol) of the compound A-15 were added to a separable flask equipped with a thermometer, a reflux tube and a nitrogen feeding pipe, and dissolved in a mixed solvent of 12.58 g of methyl ethyl ketone (MEK) and 12.58 g of cyclohexanone (CH) to obtain a solution. Then, 9.60 mmol of dimethyl 2,2'-azobis(isobutyrate) (product name: V-601, manufactured by Wako Pure Chemical Industries, Ltd.) as a polymerization initiator was added and dissolved in the obtained solution. The solution was added in a dropwise manner under a nitrogen atmosphere over 4 hours to a mixed solution prepared by dissolving 6.97 g (26.57 mmol) of the compound 2 in a mixed organic solvent of 6.93 g of MEK and 6.93 g of CH followed by heating to 80° C. Thereafter, the reaction solution was heated for 1 hour while stirring, and then cooled to room temperature. The obtained reaction polymer solution was dropwise added to an excess amount of n-heptane to deposit a polymer. Thereafter, the precipitated white powder was separated by filtration, followed by washing with methanol, and then drying, thereby obtaining 9.88 g of a polymeric compound 1 as an objective compound.

With respect to the polymeric compound, the weight average molecular weight (Mw) and the dispersity (Mw/Mn) were determined by the polystyrene equivalent value as measured by gel permeation chromatography (GPC). As a result, it was found that the weight average molecular weight was 1,400, and the dispersity was 7.72. Further, the polymeric compound was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m/n/o=34.5/39.8/17.1/8.6.

[Chemical Formula 98]

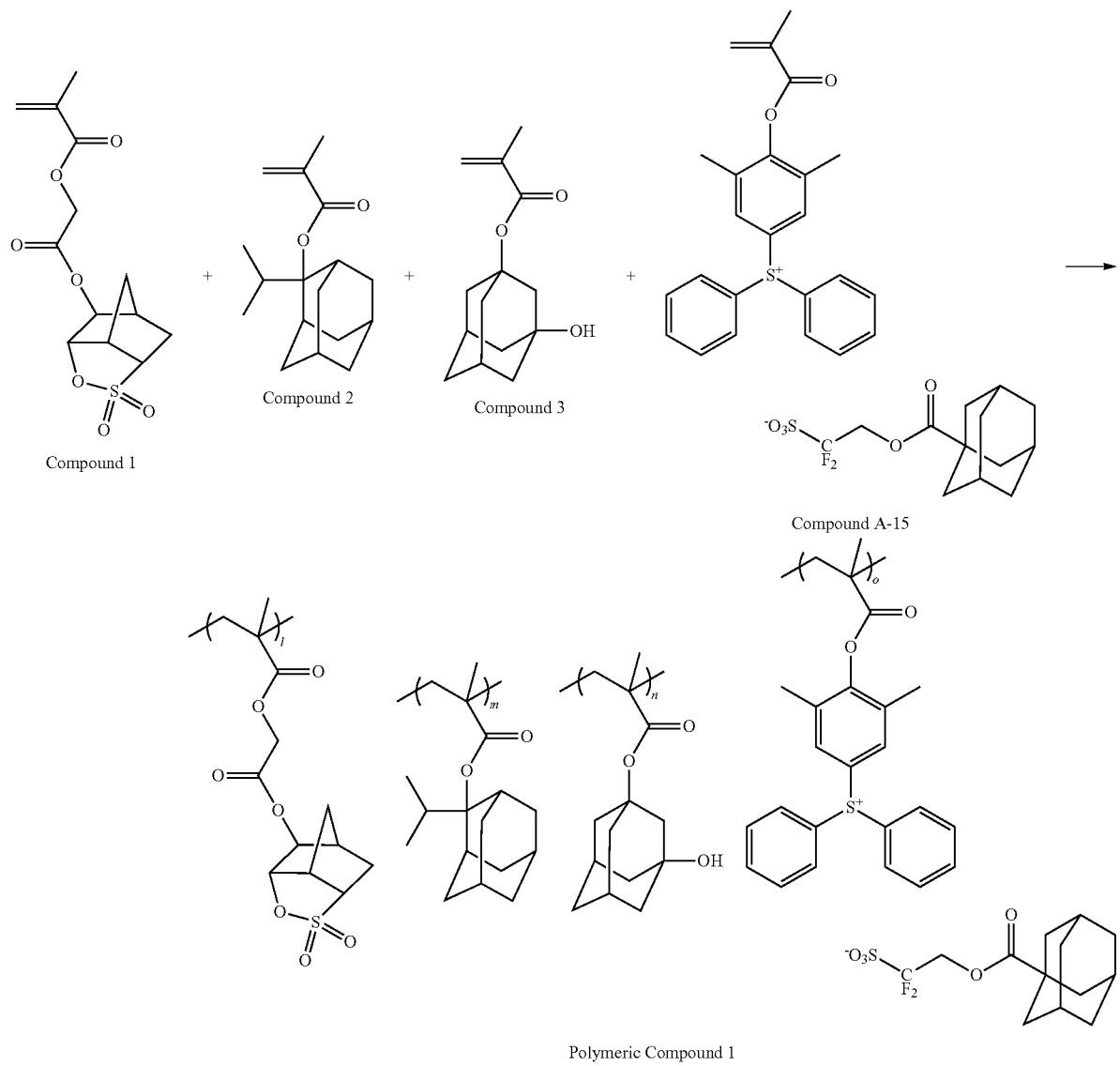

The compound 1 used in the aforementioned process can be synthesized by a method described in WO2010/001913.

Polymer Synthesis Example 2

The same procedure as in Polymer Synthesis Example 1 was performed, except that the compound A-16 was used instead of the compound A-15, thereby obtaining a polymeric compound 2.

With respect to the polymeric compound, the weight average molecular weight (Mw) and the dispersity (Mw/Mn) were determined by the polystyrene equivalent value as measured by gel permeation chromatography (GPC). As a result, it was found that the weight average molecular weight was 1,400, and the dispersity was 7.55. Further, the polymeric compound was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m/n/o=33.8/37.9/19.5/8.8.

[Chemical Formula 99]

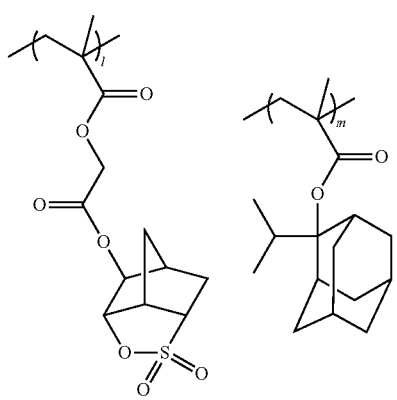

-continued

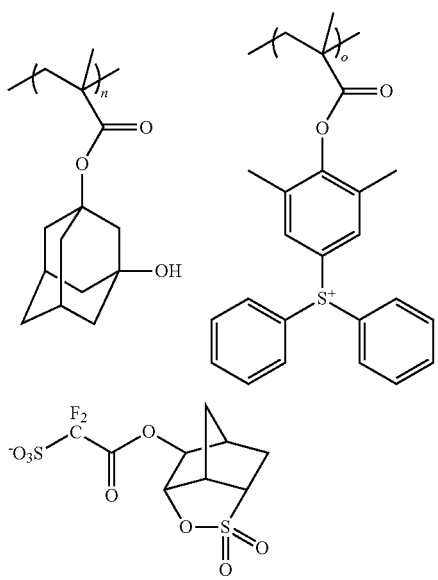

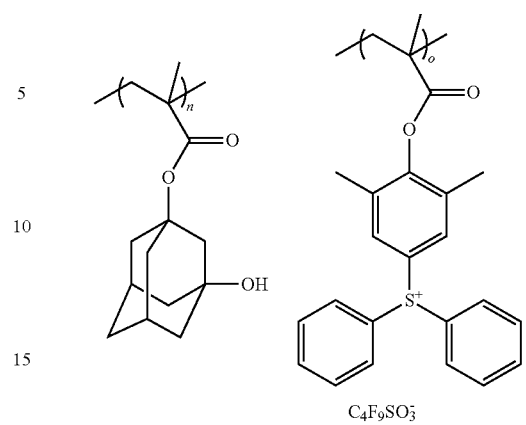

$C_4F_9SO_3^-$

Examples 1 to 6 and Comparative Examples 1 to 3

The components shown in Table 3 were mixed together and dissolved to obtain positive resist compositions.

Comparative Polymer Synthesis Example 1

The same procedure as in Polymer Synthesis Example 1 was performed, except that the monomer component (1) described in Examples of Japanese Unexamined Patent Application, First Publication No. 2006-45311 was used instead of the compound A-15, thereby obtaining a polymeric compound 1'.

With respect to the polymeric compound, the weight average molecular weight (Mw) and the dispersity (Mw/Mn) were determined by the polystyrene equivalent value as measured by gel permeation chromatography (GPC). As a result, it was found that the weight average molecular weight was 1,400, and the dispersity was 7.36. Further, the polymeric compound was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m/n/o=38.2/36.4/18.3/7.1.

[Chemical Formula 100]

Polymeric Compound 1'

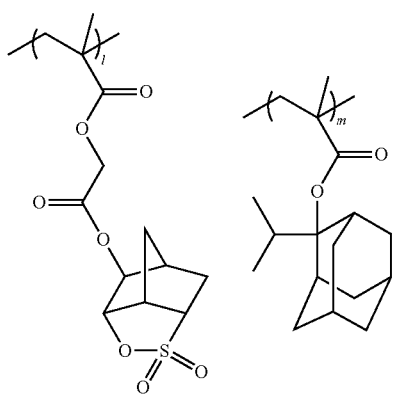

TABLE 3

| | Component (A) | Component (B) | Component (D) | Component (S) | |
|---|---|---|---|---|---|
| Example 1 | (A)-1 [100] | — | — | (S)-1 [5390] | — |
| Example 2 | (A)-2 [100] | — | — | (S)-1 [5390] | — |
| Comparative Example 1 | (A')-1 [100] | — | — | (S)-1 [5390] | — |
| Example 3 | (A)-1 [100] | (B)-1 [25.8] | (D)-1 [0.9] | (S)-1 [5390] | (S)-2 [200] |
| Example 4 | (A)-2 [100] | (B)-1 [25.8] | (D)-1 [0.9] | (S)-1 [5390] | (S)-2 [200] |
| Comparative Example 2 | (A')-1 [100] | (B)-1 [25.8] | (D)-1 [0.9] | (S)-1 [5390] | (S)-2 [200] |
| Example 5 | (A)-1 [100] | (B)-2 [28.0] | (D)-1 [0.9] | (S)-1 [5390] | (S)-2 [200] |
| Example 6 | (A)-2 [100] | (B)-2 [28.0] | (D)-1 [0.9] | (S)-1 [5390] | (S)-2 [200] |
| Comparative Example 3 | (A')-1 [100] | (B)-2 [28.0] | (D)-1 [0.9] | (S)-1 [5390] | (S)-2 [200] |

In Table 3, the reference characters indicate the following. Further, in Table 3, the values in brackets [ ] indicate the amount (in terms of parts by weight) of the component added.

(A)-1: the aforementioned polymeric compound 1

(A)-2: the aforementioned polymeric compound 2

(A')-1: the aforementioned polymeric compound 1'

(B)-1: a compound represented by chemical formula (B)-1 shown below (B)-2: a compound represented by chemical formula (B)-2 shown below (D)-1: a compound represented by formula (D)-1 shown below (i.e., acetamide-adamantine)

(S)-1: a mixed solvent of PGMEA/PGME/cyclohexanone=2205/1960/1225 (weight ratio)

(S)-2: γ-butyrolactone

[Chemical Formula 101]

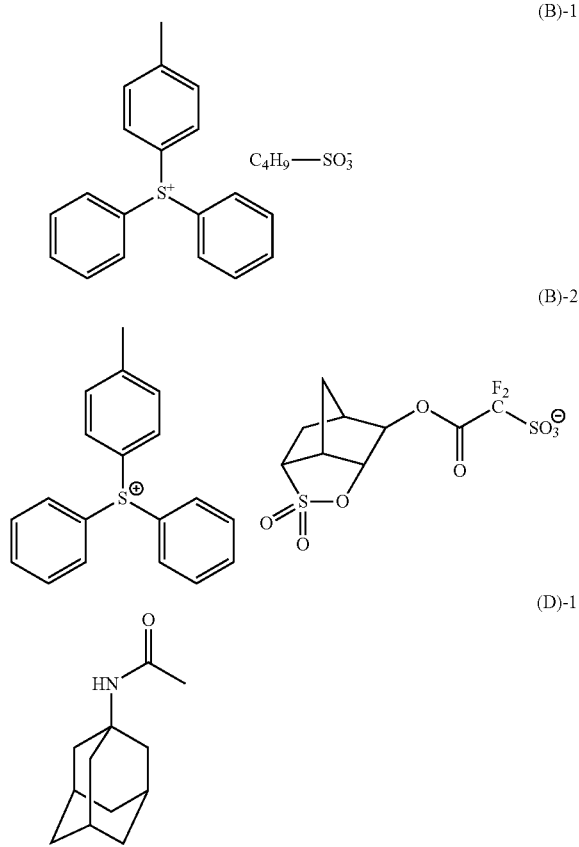

Using the obtained resist compositions, the following evaluations were conducted.

[Formation of Resist Pattern]

Using a spinner, the aforementioned resist composition was applied to an 8-inch silicon wafer that had been treated with hexamethyldisilazane (HMDS) at 90° C. for 36 seconds, and the solution was then subjected to a bake treatment (PAB) at a temperature indicated in Table 4 for 60 seconds, thereby forming a resist film (film thickness: 60 nm).

Subsequently, the resist film was subjected to drawing (exposure) with an acceleration voltage of 70 keV using an electron beam lithography apparatus HL-800D (VSB) (manufactured by Hitachi, Ltd.), followed by a bake treatment (PEB) at a temperature indicated in Table 4 for 60 seconds. Then, development was conducted with a 2.38 wt % aqueous TMAH solution (product name: NMD-3; manufactured by Tokyo Ohka Kogyo Co., Ltd.) at 23° C. for 60 seconds, followed by rinsing for 15 seconds with pure water and drying by shaking. As a result, in each of the examples, a line and space pattern (hereafter, referred to as "LS pattern") having a line width of 100 nm and a pitch of 200 nm was formed.

[Evaluation of Resolution]

The critical resolution (nm) with the above optimum exposure dose Eop ($\mu J/cm^2$) with which the LS pattern having a line width of 100 nm and a pitch of 200 nm could be formed in the above [formation of resist pattern] was determined using a measuring scanning electron microscope (product name: S-9220, manufactured by Hitachi, Ltd.). The results are indicated under "resolution" in Table 4.

[Evaluation of Line Edge Roughness (LER)]

An LS pattern having a line width of 100 nm and a pitch of 200 nm was formed with the above Eop in the same procedure as in the aforementioned [Formation of resist pattern].

With respect to the LS pattern having a line width of 100 nm and a pitch of 200 nm, $3\sigma$ was determined as a yardstick of LER. The "$3\sigma$" refers to a value of 3 times the standard deviation ($\sigma$) (unit: nm) calculated from a result in which the line width at 400 points in the lengthwise direction of the line were measured using a measuring scanning electron microscope (SEM) (product name: S-9220, manufactured by Hitachi, Ltd.; acceleration voltage: 800V). The smaller this 3s value is, the lower the level of roughness of the side walls of a line pattern, indicating that a LS pattern with a uniform width was obtained. The results are shown in Table 4.

[Evaluation of EL Margin]

An LS pattern having a line width of 100 nm and a pitch of 200 nm was formed in the same procedure as in the aforementioned [Formation of resist pattern], except that exposure was conducted while changing the exposure dose. The exposure dose with which a LS pattern having a dimension of the target dimension (line width: 100 nm) ±5% (i.e., 95 nm and 105 nm) was determined, and the EL margin (unit: %) was determined by the following formula. The results are shown in Table 4.

$$EL\ margin\ (\%) = (|E1 - E2|/Eop) \times 100$$

In the formula, E1 represents the exposure dose ($\mu J/cm^2$) for forming a L/S pattern having a line width of 95 nm, and E2 represents the exposure dose ($\mu J/cm^2$) for forming a US pattern having a line width of 105 nm.

TABLE 4

| | Component (A) | Component (B) | PAB/PEB [° C.] | Eop [$\mu C/cm^2$] | Resolution [nm] | LER [nm] | EL [%] |
|---|---|---|---|---|---|---|---|
| Example 1 | (A)-1 | — | 105/95 | 47.1 | 60 | 8.6 | 23.2 |
| Example 2 | (A)-2 | — | 105/95 | 50.0 | 50 | 8.1 | 25.1 |
| Comparative Example 1 | (A')-1 | — | 105/95 | 20.2 | 70 | 13.7 | 21.2 |
| Example 3 | (A)-1 | (B)-1 | 105/90 | 36.3 | 60 | 9.9 | 10.5 |
| Example 4 | (A)-2 | (B)-1 | 105/90 | 50.2 | 60 | 7.6 | 15.7 |
| Comparative Example 2 | (A')-1 | (B)-1 | 105/90 | 32.3 | 60 | 10.5 | 10.8 |
| Example 5 | (A)-1 | (B)-2 | 105/90 | 38.6 | 60 | 9.7 | 11.0 |
| Example 6 | (A)-2 | (B)-2 | 105/90 | 53.4 | 50 | 6.8 | 18.6 |
| Comparative Example 3 | (A')-1 | (B)-2 | 105/90 | 47.0 | 60 | 10.4 | 16.4 |

From a comparison between Examples 1 and 2, and Comparative Example 1 which had a same composition expect for the component (A), Example 1 in which (A)-1 was used and Example 2 in which (A)-2 was used exhibited improved LER, as compared to Comparative Example 1 in which (A')-1 was used. It is presumed that the acid containing an anion moiety of (A)-1 or (A)-2 has a short diffusion length in the resist film, as compared to the acid containing an anion ($C_4F_9SO_3^-$) of (A')-1.

In particular, Example 2 further exhibited improved resolution and EL. It is presumed that the anion moiety of (A)-2 has a —$SO_2$-containing cyclic group at the terminal thereof, due to its high polarity, the diffusion length of acid in the resist film is shorten as compared to the anion moiety containing a hydrocarbon group such as an adamantyl group.

In relation to Examples 3, 4 and Comparative Example 2, and in relation to Examples 5, 6, and Comparative Example 3, the same tendency was observed as in Examples 1, 2 and Comparative Example 1.

From a comparison between Examples 2, 4 and 6, it was confirmed that by using (B)-2, resolution was further improved. It is presumed that the acid composed of the anion moiety of (B)-2 has a short diffusion length in the resist film, as well as the acid composed of the anion moiety of (A)-2.

What is claimed is

1. A resist composition which exhibits changed solubility in an alkali developing solution upon exposure, comprising:

a polymeric compound (A) having a structural unit (a0) represented by general formula (a0) shown below:

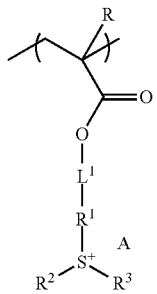
(a0)

wherein R represents a hydrogen atom, an alkyl group of 1 to 5 carbon atoms or a halogenated alkyl group of 1 to 5 carbon atoms; $R^1$ represents a divalent aromatic cyclic group; each of $R^2$ and $R^3$ independently represents an aryl group with or without a substituent, an alkyl group with or without a substituent or an alkenyl group with or without a substituent, wherein $R^2$ and $R^3$ may be mutually bonded to form a ring with the sulfur atom; $L^1$ represents a single bond or a divalent linking group; and A represents an anion represented by general formula (11a), (11b), (11c), (11e), (11f), (12a), (12b), (12c), (12d) or (2) shown below:

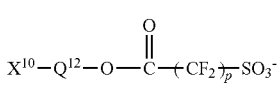
(11a)

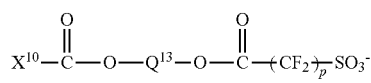
(11b)

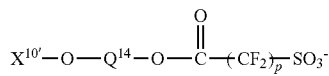
(11c)

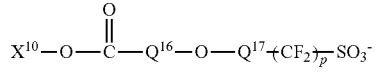
(11e)

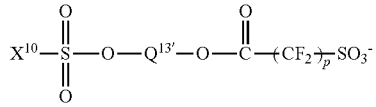
(11f)

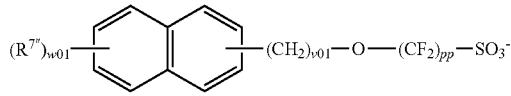
(12a)

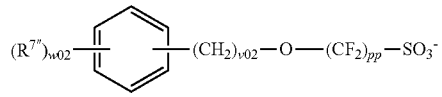
(12b)

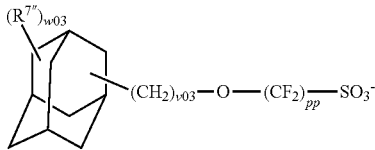
(12c)

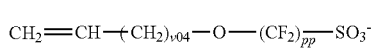
(12d)

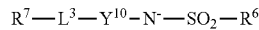
(2)

wherein in formula (11a), $X^{10}$ represents an —S(=O)$_2$— containing cyclic group, p represents an integer of 1 to 3, and $Q^{12}$ represents a single bond or an alkylene group;

in formula (11b), $X^{10}$ represents a hydrocarbon group of 3 to 30 carbon atoms with or without a substituent, p represents an integer of 1 to 3, and $Q^{13}$ represents an alkylene group;

in formula (11c), p represents an integer of 1 to 3, $X^{10'}$ represents a fluorinated aryl group with or without a substituent, and $Q^{14}$ represents a single bond or an alkylene group;

in formula 11e), $X^{10}$ represents a hydrocarbon group of 3 to 30 carbon atoms with or without a substituent, p represents an integer of 1 to 3, $Q^{16}$ represents an alkylene group, and $Q^{17}$ represents a methylene group;

in formula (11f), $X^{10}$ represents a hydrocarbon group of 3 to 30 carbon atoms with or without a substituent, p represents an integer of 1 to 3, and $Q^{13'}$ represents an alkylene group in the formulae (12a), (12b), (12c) and (12d), $R^{7''}$ represents a substituent, w01 represents an integer of 0 to 7, w02 represents an integer of 0 to 5, w03 represents an integer of 0 to 15, each of v01 to v04 independently represents an integer of 0 to 5, and pp represents an integer of 1 to 3; and in formula (2), $R^6$ represents an alkyl group with or without a substituent or a fluorinated alkyl group with or without a substituent; $L^3$ represents a single bond or a divalent linking group; $Y^{10}$ represents a —CO—; and $R^7$ represents a hydrocarbon group with or without a substituent.

2. The resist composition according to claim 1, wherein the polymeric compound (A) comprises an acid dissociable, dissolution inhibiting group, and exhibits increased solubility in an alkali developing solution by the action of acid.

3. The resist composition according to claim 1, wherein the polymeric compound (A) further comprises a structural unit (a1) derived from an acrylate ester containing an acid dissociable, dissolution inhibiting group.

4. The resist composition according to claim 3, wherein the polymeric compound (A) further comprises a structural unit (a2) which is at least one structural unit selected from the group consisting of a structural unit derived from an acrylate ester containing a —SO$_2$— containing cyclic group and a structural unit derived from an acrylate ester containing a lactone-containing cyclic group.

5. The resist composition according to claim 3, wherein the polymeric compound (A) further comprises a structural unit (a3) derived from an acrylate ester containing a polar group-containing aliphatic hydrocarbon group.

6. The resist composition according to claim 1, further comprising an acid-generator component (B) that generates acid upon exposure, exclusive of the polymeric compound (A).

7. The resist composition according to claim 6, wherein the acid-generator component (B) is an onium salt acid generator containing an anion moiety represented by general formula (1') or (2') shown below:

wherein in formula (1'), $R^{4\prime}$ represents an alkylene group of 1 to 4 carbon atoms with or without a substituent or a fluorinated alkylene group of 1 to 4 carbon atoms with or without a substituent; $L^{2\prime}$ represents a single bond or a divalent linking group; and $R^{5\prime}$ represents a hydrocarbon group of 3 to 30 carbon atoms with or without a substituent; and in formula (2'), $R^{6\prime}$ represents an alkyl group with or without a substituent or a fluorinated alkyl group with or without a substituent; $L^{3\prime}$ represents a single bond or a divalent linking group; $Y10'$ represents a $-SO_2-$ or a $-CO-$; and $R^{7\prime}$ represents a hydrocarbon group with or without a substituent.

8. A method of forming a resist pattern, comprising:
forming a resist film on a substrate using the resist composition of claim 1;
exposing the resist film; and
alkali-developing the resist film to form a resist pattern.

9. A polymeric compound comprising a structural unit (a0) represented by general formula (a0) shown below:

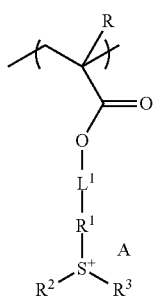

wherein R represents a hydrogen atom, an alkyl group of 1 to 5 carbon atoms or a halogenated alkyl group of 1 to 5 carbon atoms; $R^1$ represents a divalent aromatic cyclic group; each of $R^2$ and $R^3$ independently represents an aryl group with or without a substituent, an alkyl group with or without a substituent or an alkenyl group with or without a substituent, wherein $R^2$ and $R^3$ may be mutually bonded to form a ring with the sulfur atom; $L^1$ represents a single bond or a divalent linking group; and A represents an anion represented by general formula (11a), (11b), (11c), (11e), (11f), (12a), (12b), (12c), (12d) or (2) shown below:

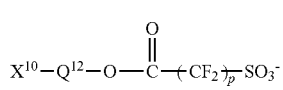

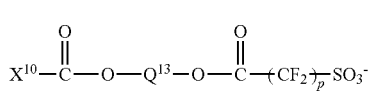

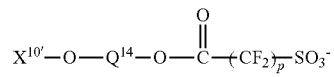

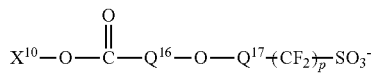

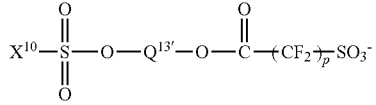

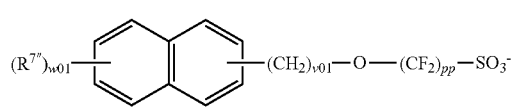

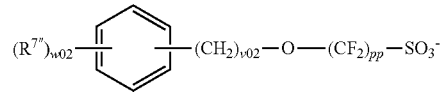

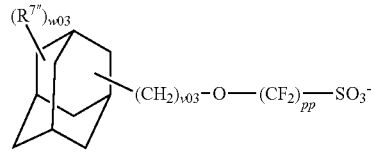

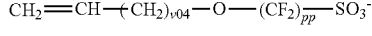

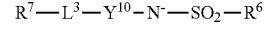

wherein in formula (11a), $X^{10}$ represents an $-S(=O)_2-$ containing cyclic group, p represents an integer of 1 to 3, and $Q^{12}$ represents a single bond or an alkylene group;

in formula (11b), represents a hydrocarbon group of 3 to 30 carbon atoms with or without a substituent, p represents an integer of 1 to 3, and $Q^{13}$ represents an alkylene group;

in formula (11c), p represents an integer of 1 to 3, $X^{10\prime}$ represents a fluorinated aryl group with or without a substituent, and $Q^{14}$ represents a single bond or an alkylene group;

in formula (11e), $X^{10}$ represents a hydrocarbon group of 3 to 30 carbon atoms with or without a substituent, p represents an integer of 1 to 3, $Q^{16}$ represents an alkylene group, and $Q^{17}$ represents a methylene group;

in formula (11f), X represents a hydrocarbon group of 3 to 30 carbon atoms with or without a substituent, p represents an integer of 1 to 3, and $Q^{13\prime}$ represents an alkylene group in the formulae (12a), (12b), (12c) and (12d), $R^{7\prime\prime}$ represents a substituent, w01 represents an integer of 0 to 7, w02 represents an integer of 0 to 5, w03 represents an integer of 0 to 15, each of v01 to v04 independently represents an integer of 0 to 5, and pp represents an integer of 1 to 3; and in formula (2), $R^6$ represents an alkyl group with or without a substituent or a fluorinated alkyl group with or without a substituent; $L^3$ represents a single bond or a divalent linking group; $Y^{10}$ represents a $-CO-$; and $R^7$ represents a hydrocarbon group with or without a substituent.

10. The polymeric compound according to claim 9, which comprises an acid dissociable, dissolution inhibiting group, and exhibits increased solubility in an alkali developing solution by the action of acid.

11. The polymeric compound according to claim 10, which further comprises a structural unit (a1) derived from an acrylate ester containing an acid dissociable, dissolution inhibiting group.

12. The polymeric compound according to claim 11, which further comprises a structural unit (a2) which is at least one structural unit selected from the group consisting of a structural unit derived from an acrylate ester containing a —SO$_2$— containing cyclic group and a structural unit derived from an acrylate ester containing a lactone-containing cyclic group.

13. The polymeric compound according to claim 11, which further comprises a structural unit (a3) derived from an acrylate ester containing a polar group-containing aliphatic hydrocarbon group.

14. A compound represented by general formula (I) shown below:

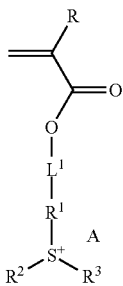
(I)

wherein R represents a hydrogen atom, an alkyl group of 1 to 5 carbon atoms or a halogenated alkyl group of 1 to 5 carbon atoms; $R^1$ represents a divalent aromatic cyclic group; each of $R^2$ and $R^3$ independently represents an aryl group with or without a substituent, an alkyl group with or without a substituent or an alkenyl group with or without a substituent, wherein $R^2$ and $R^3$ may be mutually bonded to form a ring with the sulfur atom; $L^1$ represents a single bond or a divalent linking group; and A represents an anion represented by general formula (11a), (11b), (11c), (11e), (11f), (12a), (12b), (12c), (12d) or (2) shown below:

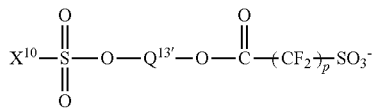
(11a)

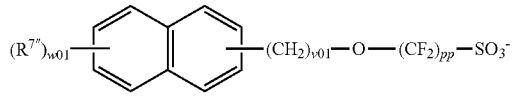
(11b)

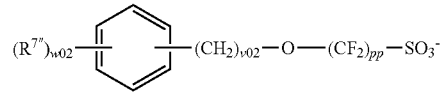
(11c)

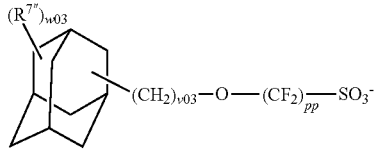
(11e)

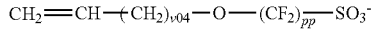
(11f)

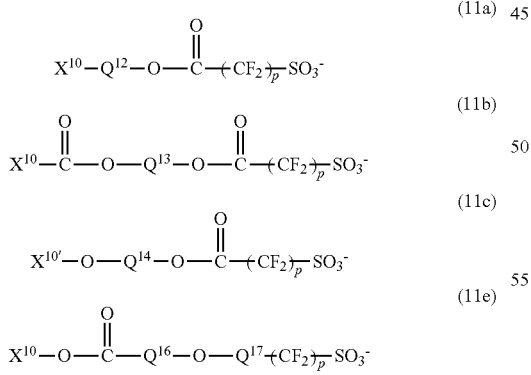

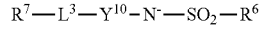
(2)

wherein in formula (11a), $X^{10}$ represents an —S(=O)$_2$— containing cyclic group, p represents an integer of 1 to 3, and $Q^{12}$ represents a single bond or an alkylene group;

in formula (11b), $X^{10}$ represents a hydrocarbon group of 3 to 30 carbon atoms with or without a substituent, p represents an integer of 1 to 3, and $Q^{13}$ represents an alkylene group;

in formula (11c), p represents an integer of 1 to 3, $X^{10\prime}$ represents a fluorinated aryl group with or without a substituent, and $Q^{14}$ represents a single bond or an alkylene group;

in formula (11e), $X^{10}$ represents a hydrocarbon group of 3 to 30 carbon atoms with or without a substituent, p represents an integer of 1 to 3, $Q^{16}$ represents an alkylene group, and $Q^{17}$ represents a methylene group;

in formula (11f), $X^{10}$ represents a hydrocarbon group of 3 to 30 carbon atoms with or without a substituent, p represents an integer of 1 to 3, and $Q^{13\prime}$ represents an alkylene group in the formulae (12a), (12b), (12c) and (12d), $R^{7\prime\prime}$ represents a substituent, w01 represents an integer of 0 to 7, w02 represents an integer of 0 to 5, w03 represents an integer of 0 to 15, each of v01 to v04 independently represents an integer of 0 to 5, and pp represents an integer of 1 to 3; and in formula (2), $R^6$ represents an alkyl group with or without a substituent or a fluorinated alkyl group with or without a substituent; $L^3$ represents a single bond or a divalent linking group; $Y^{10}$ represents a —CO—; and $R^7$ represents a hydrocarbon group with or without a substituent.

* * * * *

UNITED STATES PATENT AND TRADEMARK OFFICE
CERTIFICATE OF CORRECTION

PATENT NO. : 9,023,581 B2
APPLICATION NO. : 13/703865
DATED : May 5, 2015
INVENTOR(S) : Akiya Kawaue et al.

It is certified that error appears in the above-identified patent and that said Letters Patent is hereby corrected as shown below:

Title Page
Page 1 (item 74), line 1, "Olsen" should be --Olson--.
Specification
Col. 2, line 52, "example." should be --example,--.
Col. 3, line 36, "contains" should be --contains.--.
Col. 5, line 60, "R'" should be --$R^1$--.
Col. 13, line 46, "$P]_m$" should be --$O]_m$--.
Col. 15, line 28, "β" should be --O--.
Col. 20, line 3, "β-propionolatone," should be --β-propiolactone,--.
Col. 20, line 25, "sultone" should be --sulfone--.
Col. 24, line 55, "preferable" should be --preferable.--.
Col. 38, line 17, "(a1))" should be --(a1)--.
Col. 76, line 22, "(I-1)" should be --(1-1)--.
Col. 76, line 67, "(I" should be --(1--.
Col. 77, line 45, "sultone" should be --sulfone--.
Col. 85, line 1, "$L^4$epresents" should be --$L^4$ represents--.
Col. 87, line 51, "β-propionolatone," should be --β-propiolactone,--.
Col. 88, line 11, "COOK'" should be --COOR"--.
Col. 104, line 36, "2-norbonyl" should be --2-norbornyl--.
Col. 104, line 36, "3-norbonyl" should be --3-norbornyl--.
Col. 107, line 48, "A"," should be --A',--.
Col. 108, line 14, "sulfoneamide" should be --sulfonamide--.
Col. 108, line 26, "(AlBN)." should be --(AIBN).--.
Col. 108, line 40, "(1)" should be --(I)--.
Col. 110, line 6, "atoms)" should be --atoms--.
Col. 118, line 36, "nonafluorobutanesulfonae;" should be --nonafluorobutanesulfonate;--.
Col. 118, lines 36-37, "tetrahydrothopyranium" should be --tetrahydrothiopyranium--.
Col. 119, line 21, "R'" should be --$R^7$--.
Col. 125, line 22, "sulfoneamide" should be --sulfonamide--.

Signed and Sealed this
Sixteenth Day of August, 2016

Michelle K. Lee
*Director of the United States Patent and Trademark Office*

CERTIFICATE OF CORRECTION (continued)
U.S. Pat. No. 9,023,581 B2

Col. 125, line 27, "polycyclolefin" should be --polycycloolefin--.
Col. 126, line 64, "4-acetamidecyclohexanone," should be --4-acetamidocyclohexanone,--.
Col. 129, line 52, "perfluorialkylsulfonate" should be --perfluoroalkylsulfonate--.
Col. 130, line 64, "at" should be --as--.
Col. 135, line 33, "dicyclohexylcarboxylmide" should be --dicyclohexylcarbodiimide--.
Col. 156, line 63, "adamantine)" should be --adamantane)--.
Claims
Col. 160, line 30 (claim 1), "11e)," should be --(11e),--.
Col. 161, line 21 (claim 7), "Y10'" should be --$Y^{10'}$--.
Col. 161, line 22 (claim 7), "—$SO_2$—or" should be -- —$SO_2$— or--.
Col. 161, line 55 (claim 9), "(11b )," should be --(11b),--.
Col. 162, line 38 (claim 9), after "(11b)," insert --$X^{10}$--.
Col. 162, line 48 (claim 9), "3,$Q^{16}$" should be --3, $Q^{16}$--.
Col. 162, line 50 (claim 9), "X" should be --$X^{10}$--.
Col. 162, line 52 (claim 9), "3,and" should be --3, and--.
Col. 163, line 2 (claim 11), "(al)" should be --(a1)--.
Col. 164, line 29 (claim 14), "3,and" should be --3, and--.
Col. 164, line 33 (claim 14), "3,and" should be --3, and--.
Col. 164, line 46 (claim 14), "3,and" should be --3, and--.